United States Patent

Ikeda et al.

[11] Patent Number: 6,156,752
[45] Date of Patent: *Dec. 5, 2000

[54] OPTICALLY ACTIVE 1,4-DIHYDROPYRIDINE COMPOUNDS AS BRADYKININ ANTAGONISTS

[75] Inventors: Takafumi Ikeda, Handa; Mitsuhiro Kawamura, Chita-gun; Yu-Ting Ge, Handa, all of Japan

[73] Assignee: Pfizer Inc, New York, N.Y.

[*] Notice: This patent is subject to a terminal disclaimer.

[21] Appl. No.: 09/133,580

[22] Filed: Aug. 13, 1998

[30] Foreign Application Priority Data

Aug. 18, 1997 [WO] WIPO ............ PCT/IB97/01000

[51] Int. Cl.[7] ............ C07D 401/06; A61K 31/497
[52] U.S. Cl. ............ 514/252; 514/255; 514/256; 514/305; 514/318; 544/362; 544/365; 544/364; 544/333; 546/133; 546/194
[58] Field of Search ............ 544/365, 362, 544/333, 364; 514/252, 255, 256, 318, 305; 546/133, 194

[56] References Cited

U.S. PATENT DOCUMENTS

| | | | |
|---|---|---|---|
| 4,510,310 | 4/1985 | Wehinger et al. | 546/321 |
| 4,578,467 | 3/1986 | Bonacchi et al. | 544/360 |
| 4,786,641 | 11/1988 | Goldmann et al. | 514/302 |

FOREIGN PATENT DOCUMENTS

| | | |
|---|---|---|
| WO9606082 | 2/1996 | WIPO . |
| WO9606083 | 2/1996 | WIPO . |
| WO9730048 | 8/1997 | WIPO . |

*Primary Examiner*—Jane Fan
*Attorney, Agent, or Firm*—Peter C. Richardson; Paul H. Ginsburg; Roy F. Waldron

[57] ABSTRACT

This invention provides a compound of the formula (I):

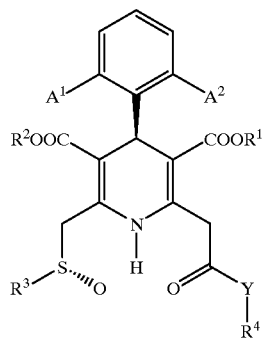

(I)

and its pharmaceutically acceptable salts, wherein $A^1$ and $A^2$ are each halo; $R^1$ and $R^2$ are independently $C_{1-4}$ alkyl; $R^3$ is substituted or unsubstituted, phenyl or naphthyl; Y is heterocyclic group selected from $C_{5-10}$ azacycloalkyl, $C_{6-10}$ diazacycloalkyl, $C_{7-10}$ azabicycloalkyl and the like; and $R^4$ is selected from (a) substituted or unsubstituted $C_{1-8}$ alkyll; (b) substituted or unsubstituted amino; (c) substituted or unsubstituted $C_{2-6}$ alkanoyl; (d) substituted or unsubstituted $C_{3-8}$ cycloalkyl or $C_{7-14}$ bicycloalkyl; (e) substituted or unsubstituted $C_{5-10}$ azacycloalkyl or $C_{6-10}$ diazacycloalkyl, and (f) substituted or unsubstituted $C_{7-14}$ mono- or di-azabicycloalkyl. These compounds are useful for the treatment of medical conditions caused by bradykinin such as inflammation, cardiovascular disease, pain, etc. This invention also provides a pharmaceutical composition comprising the above compound, and intermediates of the above compounds.

8 Claims, No Drawings

OPTICALLY ACTIVE 1,4-DIHYDROPYRIDINE COMPOUNDS AS BRADYKININ ANTAGONISTS

TECHNICAL FIELD

This invention relates to novel optically active 1,4-dihydropyridine compounds, and more particularly to optically active 1,4-dihydropyridine compounds having a substituted or unsubstituted-sulfinylmethyl group attached to the 2-position of the dihydropyridine ring. These compounds are useful as antagonists of bradykinin, and are thus useful in the treatment of inflammation, cardiovascular disease or the like in mammalian, especially humans. The present invention also relates to a pharmaceutical composition comprising the above compounds.

BACKGROUND ART

Bradykinin ("BK") is generated under normal conditions in mammalia by the action of various plasma enzymes such as kallikrein on high molecular weight kininogens. It is widely distributed in mammals, as are its two receptor subtypes, $B_1$ and $B_2$. The actions of BK at the $B_1$ receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and the common cold. Hence antagonists at the $B_2$ receptor should find considerable therapeutic applications. Most of the efforts in this area thus far have been directed at peptidic analogues of the BK structure, some of which have been studied as analgesics and antiinflammatory agents.

International Publication Number WO 96/06082 discloses a variety of 1,4-dihydropyridine compounds having a piperazinylcarbonylmethy group at the 2-position, as antagonists of bradykinin.

It would be desirable if there were provided a non-peptide antagonist of the $B_2$ receptor, having an improved $B_2$ antagonistic activity and a good metabolic stability.

BRIEF DISCLOSURE OF THE INVENTION

The present invention provides compound of the formula (I):

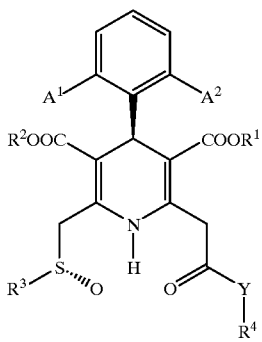

(I)

and its pharmaceutically acceptable salts, wherein
A$^1$ and A$^2$ are each halo;

R$^1$ and R$^2$ are independently $C_{1-4}$ alkyl;
R$^3$ is phenyl or naphthyl, optionally substituted with up to three substituents independently selected from halo, hydroxy, $C_{1-4}$ alkyl, halo $C_{1-4}$ alkyl and $C_{1-4}$ alkoxy;
Y is heterocyclic group selected from $C_{5-10}$ azacycloalkyl, $C_{6-10}$ diazacycloalkyl or $C_{7-10}$ azabicycloalkyl, the heterocyclic group being optionally substituted with up to two substituents independently selected from $C_{1-4}$ alkyl, halo $C_{1-4}$ allyl and $C_{1-14}$ alkoxy; and
R$^4$ is selected from the following:

(a) $C_{1-8}$ alkyl optionally substituted with up to five substituents independently selected from halo, hydroxy, amino, mono- or di-$C_{1-4}$ alkylamino, carbamoyl, carboxy, oxo, $C_{1-8}$ alkyl, $C_{1-4}$ alkoxy, $C_{2-6}$ alkanoylamino, $C_{1-4}$ alkoxycarbonyl, $C_{3-8}$ cycloalkyl, $C_{5-10}$ azacycloalkyl, $C_{7-10}$ azabicycloalkyl and $C_{6-10}$ diazacycloalkyl, wherein the azacycloalkyl, azabicycloalkyl and diazacycloalkyl are optionally substituted with up to two substituents independently selected from halo, hydroxy, $C_{1-4}$ alkyl, amino, oxo and $C_{2-6}$ alkanoyl;

(b) amino optionally substituted with up to two substituents independently selected from $C_{1-4}$ alkyl, halo $C_{1-4}$ alkyl, amino-$C_{2-4}$ alkanoyl optionally substituted with $C_{1-3}$ alkyl, $C_{3-8}$ cycloalkyl-$C_{1-4}$ alkyl and $C_{5-14}$ azabicycloalkyl optionally substituted with up to two substituents independently selected from $C_{1-4}$ alkyl, $C_{2-6}$ alkanoyl and phenyl-$C_{1-4}$ alkyl and benzoyl;

(c) $C_{2-6}$ alkanoyl optionally substituted with up to two substituents independently selected from halo, hydroxy, amino, $C_{1-4}$ alkyl, halo $C_{1-4}$ alkyl, acetylamino, carbamoylamino, $C_{1-4}$ alkoxy, $C_{1-4}$ alkoxycarbony-$C_{1-4}$ alkyl, $C_{5-10}$ azacycloalkyl, $C_{6-10}$ diazacycloalkyl and $C_{3-8}$ cycloalkyl optionally substituted with $C_{1-4}$ alkoxycarbony-$C_{1-4}$ alkyl;

(d) $C_{3-8}$ cycloalkyl or $C_{7-14}$ bicycloalkyl, wherein the cycloalkyl and bicycloalkyl are optionally substituted with up to two substituents independently selected from halo, hydroxy, amino, oxo, $C_{1-4}$ alkyl, halo $C_{1-4}$ alkyl and $C_{1-4}$ alkoxy;

(e) $C_{5-10}$ azacycloalkyl or $C_{6-10}$ diazacycloalkyl, wherein the azacycloalkyl and the diazacycloalkyl are optionally substituted with up to two substituents independently selected from halo, hydroxy, amino, $C_{1-4}$ alkyl, $C_{2-6}$ alkanoyl, halo $C_{1-4}$ alkyl, $C_{1-4}$ alkylamino-$C_{1-4}$ alkyl and phenyl-$C_{1-4}$ alkyl wherein the phenyl moiety is optionally substituted with up to two substituents independently selected from halo, hydroxy and $C_{1-4}$ alkyl; and (f) $C_{7-14}$ mono- or di-azabicycloalkyl optionally substituted with up to two substituents independently selected from halo, hydroxy, amino, oxo, $C_{1-4}$ alkyl, halo $C_{1-4}$ alkyl, $C_{2-6}$ alkanoyl, phenyl-$C_{1-4}$ alkyl wherein the phenyl moiety is optionally substituted with up to two substituents independently selected from halo, hydroxy and $C_{1-4}$ alkyl, and phenylcarbonyl wherein the phenyl moiety is optionally substituted with up to two substituents independently selected from halo, hydroxy and $C_{1-4}$ alkyl.

Since phenylsulfinyl-1,4-dihydropyridine compounds possess at least two asymmetric centers, they create various stereoisomeric forms or absolute configurations. In the present invention, (4S), [6-(S)-phenylsulfinyl]-1,4-dihydropyridine compounds are specifically selected as those having the most appropriate configuration to show good bradykinin antagonistic activities.

These optically active compounds of this invention can be prepared by several methods. For example, these optically active compounds of this invention may be obtained by chromatographic separation from the final compounds in the forms of at least four possible enantiomers and diastereomers thereof. Alternatively, these optically active compounds may be prepared by optically selective reaction, microbial oxidation, enzymatic hydrolysis, fractional crystallization or reactions using optically active intermediates.

The dihydropyridine compounds of this invention have excellent bradykinin antagonistic activity and are thus useful for the treatment of medical conditions caused by bradykinin such as inflammation, cardiovascular disease, pain, common cold, allergies, asthma, pancreatitis, burns, virus infection, head injury, multiple trauma or the like in mammalian, especially humans.

Thus, the present invention also provides a pharmaceutical composition for the treatment of inflammation, cardiovascular disease, pain, common cold, allergies, asthma, pancreatitis, burns, virus infection, head injury, multiple trauma or the like, which comprises a therapeutically effective amount of the dihydropyridine compound of formula (I) or its pharmaceutically acceptable salt together with a pharmaceutically acceptable carrier.

Further, the present invention provides a method for the treatment of disease conditions caused, by bradykinin, in a mammalian subject, which comprises administering to said subject a therapeutically effective amount of a compound of formula (I).

The present invention also provides an intermediate compound of the formula (II-c):

(II-c)

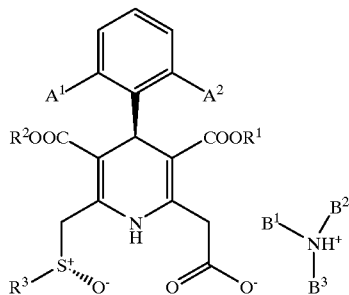

wherein $A^1$ and $A^2$ are each halo; $R^1$ and $R^2$ are independently $C_{1-4}$ alkyl; $R^3$ is phenyl or naphthyl, optionally substituted with up to three substituents independently selected from halo, hydroxy, $C_{1-4}$ alkyl, halo $C_{1-4}$ alkyl and $C_{1-4}$ alkoxy; and $[B^1B^2B^3]NH^+$ is a chiral amine residue such as cinchonine.

The present invention also provides a process for preparing the compounds of the formula (II-c), which process comprises reaction steps of:

(a) oxidizing a compound of the formula (II-a):

(II-a)

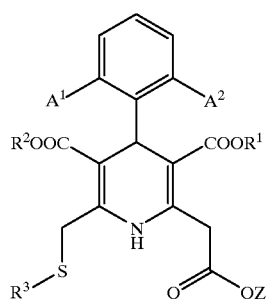

with an oxidative agent to form a compound of the formula (II-b):

(II-b)

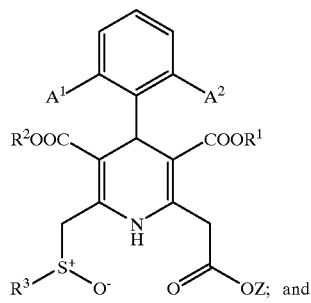

(b) subjecting the compound of the formula (II-b) to a fractional crystallization with a chiral amine, to obtain a compound of the formula (II-c).

Further, the present invention provides a process for preparing a compound of formula (II):

(II)

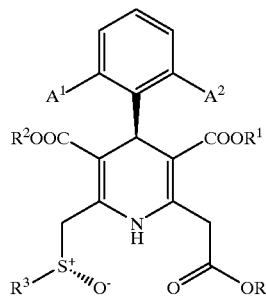

wherein $A^1$ and $A^2$ are each halo; $R^1$ and $R^2$ are independently $C_{1-4}$ alkyl; $R^3$ is phenyl or naphthyl, optionally substituted with up to three substituents independently selected from halo, hydroxy, $C_{1-4}$ alkyl, halo $C_{1-4}$ alkyl and $C_{1-4}$ alkoxy; and R is $C_{1-4}$ alkyl, which process comprises subjecting a compound of formula (II-a);

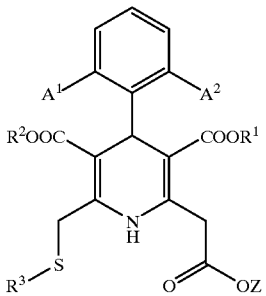

(wherein Z is hydrogen or $C_{1-6}$ alkyl) to chiral oxidation or Kagan's oxidation in the presence of an oxidative agent.

DETAILED DESCRIPTION OF THE INVENTION

As used herein, "halo" is fluoro, chloro, bromo or iodo.

As used herein, the term "alkyl" means straight or branched chain saturated radicals of 1 to 8 carbon atoms, including, but not limited to methyl, ethyl, n-propyl, isopropyl, n-butyl, iso-butyl, secondary-butyl, tertiary-butyl, pentyl, hexyl, and the like.

As used herein, the term "halo alkyl" refers to an alkyl radical as described above substituted with one or more halogens included, but not limited to, chloromethyl, fluoromethyl, difluoromethyl, trifluoromethyl, 2,2,2-trichloroethyl, and the like.

As used herein, the term "$C_{2-6}$ alkanoyl" means $C_{1-5}$ alkyl-C(O)—, including, but not limited to acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, and the like.

As used herein, the term "$C_{1-4}$ alkylamino" and "di-($C_{1-4}$ alkyl)amino" mean N(R')R", wherein R' is hydrogen or $C_{1-4}$ alkyl and R" is $C_{1-4}$ alkyl, such as methylamino, ethylamino, n-propylamino, isopropylamino, n-butylamino, t-butylamino, dimethylamino, diethylamino and ethylmethylamino;

the term "$C_{3-8}$ cycloalkyl" means monocyclic alkyl having 3 to 8 carbon atoms, such as cyclopropyl, cyclobutyl, cyclopentyl, cycloheptyl, cyclohexyl, and the like; and the term "$C_{5-10}$ azacycloalkyl, $C_{6-10}$ diazacycloalkyl, $C_{7-10}$ azabicycloalkyl or $C_{7-10}$ diazabicycloalkyl" means one or two carbons of mono- or bicyclic alkyl ring components are substituted by nitrogen atoms, included, but not limited to, piperazinyl, piperidino, piperidinyl, pyrrolidinyl, 2,3,4,5,6,7-hexahydro-1H-1,4-diazepinyl or azabicyclo[3.3.0]octyl, quinuclidinyl, azabicyclo[3.2.1]octyl, azabicyclo[3.3.1]nonyl.

Preferred compounds of this invention are those of the formula (I) wherein $A^1$ and $A^2$ are each chloro or bromo;

$R^1$ and $R^2$ are independently $C_{1-3}$ alkyl;

$R^3$ is phenyl optionally substituted with up to three substituents independently selected from halo, hydroxy, $C_{1-4}$ alkyl, halo $C_{1-4}$ alkyl and $C_{1-4}$ alkoxy;

Y is heterocyclic group selected from piperazinyl, piperidinyl, pyrrolidinyl, 2,3,4,5,6,7-hexahydro-1H-1,4-diazepinyl, azabicyclo[3.3.0]octyl, quinuclidinyl, azabicyclo[3.2.1]octyl and azabicyclo[3.3.1]nonyl, the heterocyclic group being optionally substituted with, on the carbon atom, up to two substituents independently selected from $C_{1-4}$ alkyl, halo $C_{1-4}$ alkyl and $C_{1-4}$ alkoxy; and $R^4$ is selected from the following:

(a) $C_{1-8}$ alkyl optionally substituted with up to three substituents independently selected from halo, hydroxy, amino, mono- or di-$C_{1-3}$ alkylamino, carbamoyl, carboxy, oxo, $C_{1-3}$ alkyl, $C_{1-3}$ alkoxy, $C_{2-4}$ alkanoylamino, $C_{1-3}$ alkoxycarbonyl, $C_{5-7}$ cycloalkyl, $C_{5-10}$ azacycloalkyl, $C_{7-10}$ azabicycloalkyl and $C_{6-10}$ diazacycloalkyl, wherein the azacycloalkyl, azabicycloalkyl and diazacycloalkyl are optionally substituted with up to two substituents independently selected from halo, hydroxy, $C_{1-4}$ alkyl, amino, oxo and $C_{2-6}$ alkanoyl;

(b) amino optionally substituted with up to two substituents independently selected from $C_{1-3}$ alkyl, halo-$C_{1-3}$ alkyl, amino-$C_{2-4}$ alkanoyl optionally substituted with $C_{1-3}$ alkyl, $C_{5-7}$ cycloalkyl-$C_{1-3}$ alkyl and $C_{5-10}$ azabicycloalkyl optionally substituted with $C_{1-3}$ alkyl;

(c) $C_{2-4}$ alkanoyl optionally substituted with up to two substituents independently selected from halo, hydroxy, amino, $C_{1-3}$ alkyl, halo-$C_{1-3}$ alkyl, amino, acetylamino, carbamoylamino, $C_{1-3}$ alkoxy, $C_{5-7}$ azacycloalkyl, $C_{1-3}$ alkoxycarbonyl-$C_{1-4}$ alkyl and $C_{5-7}$ cycloalkyl;

(d) $C_{5-7}$ cycloalkyl optionally substituted with up to two substituents selected from halo, hydroxy, amino, $C_{1-3}$ alkyl and halo-$C_{1-3}$ alkyl;

(e) $C_{5-7}$ azacycloalkyl optionally substituted with up to two substituents independently selected from halo, hydroxy, amino, $C_{1-3}$ alkyl, halo-$C_{1-3}$ alkyl, $C_{1-3}$ alkylamino-$C_{1-3}$ alkyl or benzyl; and (f) $C_{7-14}$ azabicycloalkyl optionally substituted with up to two substituents independently selected from halo, hydroxy, amino, oxo, $C_{1-3}$ alkyl, halo-$C_{1-3}$ alkyl, $C_{2-4}$ alkanoyl, benzyl and benzoyl.

Further preferred compounds of this invention are those of the formula (I) wherein $A^1$ and $A^2$ are each chloro;

$R^1$ and $R^2$ are independently methyl or ethyl;

$R^3$ is phenyl optionally substituted with up to two substituents independently selected from halo, hydroxy, $C_{1-3}$ alkyl, $C_{1-4}$ alkoxy and halo $C_{1-3}$ alkyl;

Y is heterocyclic group selected from piperazinyl, piperidinyl, pyrrolidinyl, 2,3,4,5,6,7-hexahydro-1H-1,4-diazepinyl and azabicyclo[3.3.0]octyl, the heterocyclic group being optionally substituted with, on the carbon atom, up to two substituents independently selected from $C_{1-3}$ alkyl, halo $C_{1-3}$ alkyl and $C_{1-3}$ alkoxy; and $R^4$ is selected from the following:

(a) $C_{1-6}$ alkyl optionally substituted with up to two substituents independently selected from hydroxy, amino, carbamoyl, carboxy, oxo, $C_{1-3}$ alkyl, $C_{2-4}$ alkanoylamino, $C_{1-3}$ alkoxycarbonyl, $C_{5-7}$ cycloalkyl, $C_{5-10}$ azacycloalkyl and $C_{6-10}$ diazacycloalkyl, wherein the azacycloalkyl and diazacycloalkyl are optionally substituted with up to two substituents independently selected from $C_{1-3}$ alkyl, amino, oxo and $C_{2-6}$ alkanoyl;

(b) amino optionally substituted with up to two substituents independently selected from $C_{1-3}$ alkyl, amino-$C_{2-4}$ alkanoyl optionally substituted with $C_{1-3}$ alkyl, $C_{5-7}$ cycloalkyl-$C_{1-3}$ alkyl and $C_{5-7}$ azabicycloalkyl optionally substituted with $C_{1-3}$ alkyl;

(c) $C_{2-4}$ alkanoyl optionally substituted with up to two substituents selected from $C_{1-3}$ alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-7}$ cycloalkyl optionally substituted with up to two substituents selected from halo, hydroxy and amino;

(e) $C_{5-7}$ azacycloalkyl optionally substituted with $C_{1-3}$ alkylamino-$C_{1-3}$ alkyl or benzyl; and (f) $C_{7-14}$ azabicycloalkyl optionally substituted with oxo, $C_{1-3}$ alkyl, $C_{2-4}$ alkanoyl, benzyl or benzoyl.

Further preferred compounds of this invention are those of the formula (I) wherein $R^1$ and $R^2$ are independently methyl;

$R^3$ is phenyl optionally substituted with halo, hydroxy, methyl, methoxy or trifluoromethyl;

Y is piperazinyl, piperidinyl, pyrrolidinyl, 2,3,4,5,6,7-hexahydro-1H-1,4-diazepinyl or azabicyclo[3.3.0]octyl;

$R^4$ is selected from the following:

(a) $C_{1-5}$ alkyl optionally substituted with up to two substituents independently selected from hydroxy, amino, carbamoyl, carboxy, oxo, $C_{1-3}$ alkyl, $C_{2-4}$ alkanoylamino, $C_{1-3}$ alkoxycarbonyl, $C_{5-7}$ cycloalkyl, $C_{5-10}$ azacycloalkyl and $C_{6-10}$ diazacycloalkyl, wherein the azacycloalkyl and diazacycloalkyl are optionally substituted with methyl, amino, oxo or acetyl;

(b) amino optionally substituted with up to two substituents independently selected from $C_{1-3}$ alkyl, amino-$C_{2-4}$ alkanoyl substituted with methyl, $C_{5-7}$ cycloalkyl-$C_{1-3}$ allyl and $C_{5-7}$ azabicycloalkyl optionally substituted with methyl;

(c) $C_{2-4}$ alkanoyl optionally substituted with up to two substituents selected from $C_{1-3}$ alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-7}$ cycloalkyl optionally substituted with up to two substituents selected from halo, hydroxy and amino;

(e) $C_{5-7}$ azacycloalkyl optionally substituted with $C_{1-3}$ alkylamino-$C_{1-3}$ alkyl or benzyl; and (f) $C_{7-10}$ azabicycloalkyl optionally substituted with oxo, $C_{1-3}$ alkyl, $C_{2-4}$ alkanoyl, benzyl or benzoyl.

Much further preferred compounds of this invention are those of the formula (I) wherein $R^3$ is phenyl optionally substituted with halo, hydroxy, methyl, methoxy or trifluoromethyl;

Y is piperazinyl, piperidinyl, pyrrolidinyl, 2,3,4,5,6,7-hexahydro-1H-1,4-diazepinyl or azabicyclo[3.3.0]octyl;

$R^4$ is selected from the following:

(a) $C_{1-3}$ alkyl optionally substituted with up to two substituents independently selected from hydroxy, amino, carbamoyl, carboxy, oxo, methyl, ethyl, acetylamino, methoxycarbonyl, $C_{5-6}$ cycloalkyl, $C_{5-10}$ azacycloalkyl and $C_{6-10}$ diazacycloalkyl, wherein the azacycloalkyl and diazacycloalkyl are optionally substituted with methyl, amino, oxo or acetyl;

(b) amino-optionally substituted with up to two substituents independently selected from methyl, ethyl, 2-amino-2-methylpropionyl, $C_{5-6}$ cycloalkylmethyl and $C_{5-7}$ azabicycloalkyl optionally substituted with methyl;

(c) $C_{2-3}$ alkanoyl optionally substituted with up to two substituents selected from C1–3 alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-6}$ cycloalkyl optionally substituted with up to two substituents selected from halo, hydroxy and amino;

(e) $C_{5-6}$ azacycloalkyl optionally substituted with $C_{1-3}$ alkylamino-$C_{1-3}$ alkyl or benzyl; and (f) $C_{7-10}$ azabicycloalkyl optionally substituted with oxo, $C_{1-3}$ alkyl, $C_{2-4}$ alkanoyl, benzyl or benzoyl.

Among these, further preferred compounds of this invention are those of the formula (I) wherein $R^3$ is phenyl; and $R^4$ is selected from the following:

(a) methyl, carbamoylmethyl, carboxymethyl, ethoxycarbonylmethyl, 2-(methoxycarbonyl)-2-methylpropyl, cyclohexylmethyl, 1-pyrrolidinoethyl, pyrrolidinopropyl, [(2R,S)-1-methyl-2-pyrrolidinyl]methyl, [(2S)-1-methyl-2-pyrrolidinyl]methyl, [(2R)-1-methyl-2-pyrrolidinyl]methyl, [(2R,S)-1-methyl-2-piperidinyl]methyl, 3-(4-acetylpiperazinyl)-1-propyl, 3-(2-oxopyrrolidino)-1-propyl, 3-(4-methylpiperazinyl)propyl, (2-amino-2-methyl)propyl, (2-acetylamino-2-methyl)propyl, (2,2-dimethyl-3-hydroxy)propyl, (3-hydroxy-3-methyl)butyl, (3-(4-methylpiperazinyl)-3-oxopropyl, 3-(4-methylpiperazinyl)-1-oxopropyl, 3-(4-acetylpiperazinyl)-1, 3-dioxopropyl and 3-pyrrolidino-3-oxo-1-propyl;

(b) dimethylamino, 2-amino-2-methylpropionylamino, cyclohexylmethylamino and 8-methyl-8-azabicyclo[3.2.1] oct-7-ylamino;

(c) (2-amino-2-methyl)propinoyl, (2-acetylamino-2-methyl)propionyl, (2,2-dimethyl-3-hydroxy)propionyl, [2-(N-carbamoyl)amino-2-methyl]propionyl, (2,2-dimethyl) propionyl, 3-(ethoxycarbonyl)propionyl, 2-(1-pyrrolidino) acetyl and 1-(methoxycarbonylmethyl)cyclopent-1-yl-acetyl (d) cyclopentyl and 4-aminocyclohexyl;

(e) piperidino, (R,S)-2-(dimethylamino) methylpyrrolidino and 4-benzylpiperazinyl; and (f) 8-methyl-8-azabicyclo[3.2.1]oct-3-yl, 8-acetyl-8-azabicyclo[3.2.1]oct-3-yl, 8-ethyl-8-azabicyclo[3.2.1]oct-3-yl, 8-isopropyl-8-azabicyclo[3.2.1]oct-3-yl, 8-benzyl-8-azabicyclo[3.2.1]oct-3-yl, 3-acetyl-3-azabicyclo[3.3.0]oct-7-yl, 4-(3-benzoyl3-azabicyclo[3.3.0]oct-7-yl and 3-oxo-bicyclo[3.3.0]oct-7-yl.

Most preferred individual compounds of this invention are:

(−)-(4S)-dimethyl 4-(2,6-dichlorophenyl)-2-[4-(8-methyl-8-azabicyclo[3.2.1]oct-3-yl)-1-piperazinyl] carbonylmethyl-6-(S)-phenylsulfinylmethyl-1,4-dihydropyridine-3,5-dicarboxylate dicitrate;

(−)-(4S)-dimethyl 4-(2,6-dichlorophenyl)-2-[4-(8-acetyl-8-azabicyclo[3.2.1]oct-3-yl)1-piperazinylcarbonylmethyl]-6-(S)-phenylsulfinylmethyl-1,4-dihydropyridine-3,5-dicarboxylate monohydrochloride;

(−)-(4S)-dimethyl 4-(2,6-dichlorophenyl)-2-[4-(8-ethyl-8-azabicyclo[3.2.1]oct-3-yl)-1-piperazinylcarbonylmethyl]-6-(S)-phenylsulfinylmethyl-1,4-dihydropyridine-3,5-dicarboxylate dihydrochloride;

(−)-(4S)-dimethyl 4-(2,6-dichlorophenyl)-2-[(3S)-3-(N-methyl-8-azabicyclo[3,2,1]oct-7-yl)amino-1-pyrrolidino] carbonylmethyl-6-[(S)-phenylsulfinylmethyl]-1, 4dihydropyridine-3,5-dicarboxylate, dihydrochloride;

(−)-(4S)-dimethyl 4-(2,6-dichlorophenyl)-2-[4-(3-oxo-bicyclo[3,3,0]oct-7-yl)-1-piperazinyl]carbonylmethyl-6-[(S)-phenylsulfinylmethyl]-1,4-dihydropyridine-3,5-dicarboxylate, monocitrate;

(−)-(4S)-dimethyl 4-(2,6-dichlorophenyl)-2-{4-(3-pyrrolidino-3-oxo-1-propyl)-1-piperazinyl] carbonylmethyl-6-(S)-phenylsulfinylmethyl-1,4-dihydropyridine-3,5-dicarboxylate monohydrochloride;

(−)-(4S)-dimethyl 4-(2,6-dichlorophenyl)-2-[4-[3-(2-oxopyrrolidino)prop-1-yl]piperazinyl]carbonylmethyl-6-(S)-phenylsulfinylmethyl-1,4-dihydropyridine-3,5-dicarboxylate monohydrochloride; and (−)-(4S)-dimethyl 4-(2,6-dichlorophenyl)-2-[4-(3-acetyl-3-azabicyclo[3.3.0]oct-7-yl) piperazinylcarbonylmethyl]-6-

(S)-phenylsulfinylmethyl-1,4-dihydropyridine-3,5-dicarboxylate monohydrochloride.

General Synthesis

The dihydropyridine compounds of formula (I) of this invention may be prepared by a variety of synthetic methods. For example, the dihydropyridine compounds of formula (I) may be prepared by reaction of compound (II) with compound (III), followed, if desired, by conversion of a compound in which $R^4$ is H into a compound in which $R^4$ is other than H, as indicated in the following Preparation Method A.

Preparation Method A:

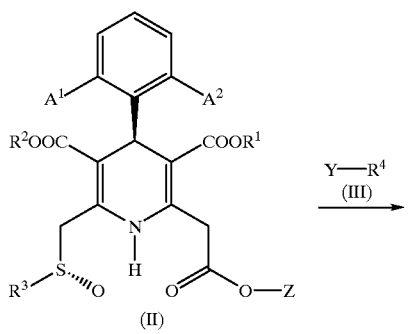

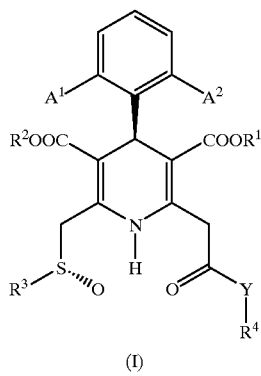

(wherein Z is hydrogen or lower alkyl (e.g., $C_{1-4}$ alkyl) such as methyl and ethyl; and the other symbols are as already defined)

In Preparation Method A, when Z is lower alkyl, the compound (II) may be first subjected to selective saponification of the ester residue at the 2-position of the compound (II), followed by acidification to afford a free acid, which is coupled with the compound (III) to give the dihydropyridine compounds (I). When Z is H, the compound (II) may be directly coupled with the compound (III) to obtain the dihydropyridine compounds (I).

The selective saponification and the acidification may be carried out by conventional procedures. In a typical procedure, the selective saponification is carried out by treatment with sodium hydroxide in aqueous methanol at a temperature in the range from −20 to 40° C., usually from 10° C. to 30° C. for 3 minutes to 4 hours, usually 15 minutes to 1 hour. In a typical procedure, the acidification is carried out by treatment with diluted hydrochloric acid in a suitable reaction-inert solvent such as water at a temperature in the range of 0 to 30° C., usually from 5° C. to 25° C. for 1 minute to 1 hour, usually 5 minutes to 15 minutes.

A compound (I) can be obtained from the corresponding compound (I) wherein $R^4$ is H by a coupling reaction between the obtained acid and 4-N-substituted piperazine. The condensation may be carried out in a reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane) using a coupling agent such as dicyclohexylcarbodiimide (DCC), water soluble carbodiimide (WSCD), 2-ethoxy-N-ethoxycarbonyl-1,2-dihydroquinoline, Bop agent (Benzotriazol-1-yloxytris (dimethylamino)phosphonium hexafluorophosphate), diethyl azodicarboxylatetriphenylphosphine, diethylcyanophosphonic acid and diphenylphosphorylazide. This reaction may be carried out at a temperature in the range from −30 to 40° C., usually from 0° C. to 25° C. for 10 minutes to 96 hours, usually 30 minutes to 24 hours.

In addition, when $R^4$ is substituted-alkyl, the 4-N-substituted piperazines (III) as used herein may be either known or may be prepared by known methods. For example, the 4-N-substituted piperazines may be prepared by means of (1) N alkylation of 4-N-protected piperazine with appropriate alkyl halide, $R^4$-halo, (2) reductive amination of 4-N-protected piperazine with appropriate aldehyde or ketone in the presence of a reducing agent, followed by deprotection of the amino-protecting group, or (3) Michael addition of 4-N-protected piperazine with appropriate conjugated ketone, ester or amide. Suitable amino-protecting groups include, for example, benzyl, benzyloxycarbonyl and t-butoxycarbonyl group.

The reductive alkylation may be carried out with appropriate aldehyde or ketone in a suitable reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane), in the presence of a suitable reducing agent such as $NaBH_4$, $NaBH_3CN$ or $NaBH(OAc)_3$ at a temperature in the range from −20 to 120° C., usually 0 to 80° C. for 10 minutes to 1 week, usually 30 minutes to 96 hours, optionally in the presence of molecular sieves. Alternatively, alkylation can be made by two step synthesis. A keton may be treated with an amine in an inert solvent such as toluene or xylene, at a temperature in the range from 80 to 130° C., usually 100 to 120° C. for 10 hours to 2 week, usually 1 days to 1 week, preferably 3 to 5 days. The product may be reduced by hydrogenation in the presence of appropriate catalyst such as Pd on carbon and $PtO_2$, usually $PtO_2$ in an inert solvent such as ethanol and ethyl acetate, usually ethyl acetate, at a temperature in the range from 10 to 60° C., usually 20 to 30° C. for 1 hour to 3 days, usually 3 hours to 10 hours.

Typical Micheal addition reaction may be carried out at a temperature in the range from 30° C. to 120° C., usually from 60° C. to 100° C. for 5 hours to a week, usually 10 hours to 4 days.

The optically active intermediates of formula (II) can be prepared by the following methods.

Preparation Method B-I (Chiral Oxidation):

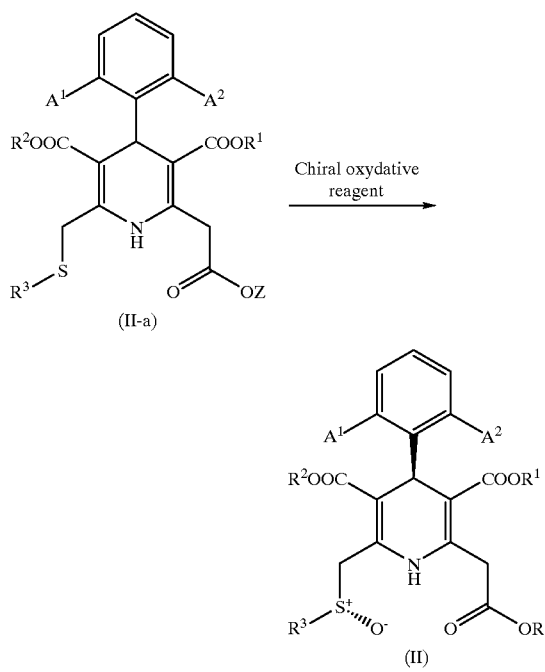

(wherein Z is hydrogen or $C_{1-6}$ alkyl; and the other symbols are already defined.)

In this method, an ester compound (II-a) may be subjected to chiral oxidation and/or diastereoselective oxidation in the presence of an oxidative agent such as Davis' oxazilidines (eg., (+)-[(8,8-dichlorocamphoryl)-sulfonyl]oxaziridine); (J. Am. Chem. Soc. 111, 5964 (1989)), or Kagan's oxidation (eg.,Ti(OiPr)4, t-BuOOH) (Tetrahedron letters 25, 1049 (1984)). These oxidation can be conducted in an organic inert solvent such as halogenated hydrocarbons (e.g., methylene chloride, chloroform and dichloroethane). These oxidation can be carried out at a temperature of −100° C. to 20° C., preferably from −50° C. to −20° C. for 10 minutes to 4 hours, preferably 30 minutes to 2 hours.

Alternatively, microbial oxidation, *Mortierella isabellina* (ATCC 42613) (H. L. Holland, et.al. Can. J. Chem., 69 1989 (1991)), and Corynebacterium equi IFO 3730 (H. Ohta, et.al., Chemistry letters 205 (1984), can be applied.

Preparation Method B-II (Fractional Crystallization):

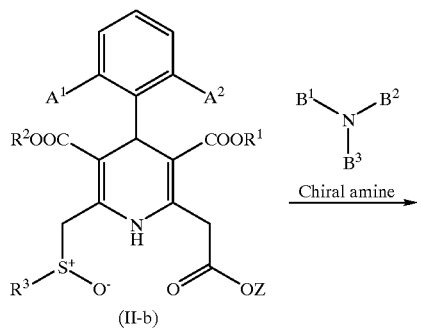

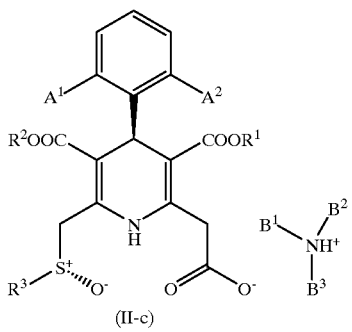

(wherein $[B^1B^2B^3]NH^+$ is a chiral amine residue; Z is hydrogen; and the other symbols are already defined.)

In this method, an acid compound (II-b) may be subjected to a fractional crystallization with a chiral amine such as cinchonidine or cinchonine, to obtain an amine salt (II-c). This reaction may be conducted in an organic solvent, preferably a pure or mixed alcoholic solvent selected from methanol, ethanol, isopropanol and a mixture thereof. The resulted salt may be further purified by several times recrystallization. The pure salt thus obtained may be converted to the corresponding carboxylic acid (Compound (II) wherein Z is H) by a partition between organic solvent such as ethyl acetate, and acid solution such as diluted hydrochloride.

In addition, the compound of formula (II-c) can be prepared by oxidising compound (II-b) with a suitable oxidative agent such as magnesium monoperoxyphthalate, hydrogen peroxide or m-chloroperbenzoic acid, preferably m-chloroperbenzoic acid. This reaction may be carried out in an inert solvent such as $CH_2Cl_2$, ethanol, acetone or a mixture thereof at a temperature in the range from −100° C. to room temperature, usually −78° C. to 0° C. for 10 minutes to 5 hours, usually 20 minutes to 3 hours, preferably 30 minutes to 1 hour.

Preparation Method B-III (Enzymatic Hydrolysis):

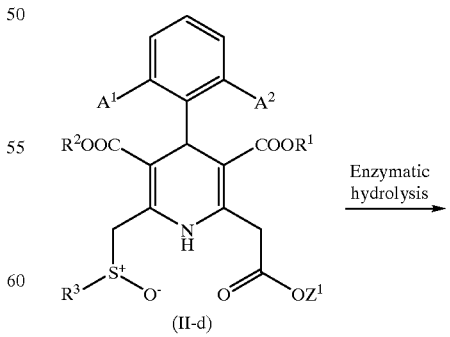

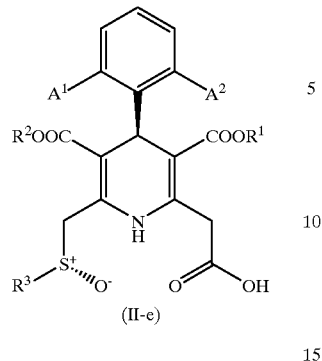

(II-e)

(wherein Z¹ is, for example, an acyloxymethyl group; and the other symbols are already defined.)

In this method, an ester compound (II-d) is subjected to enzymatic hydrolysis to obtain an optically active carboxylic acid (II-e) (Compound (II) wherein Z is H). Application of Lipase in dihydropyridine for enantioselective hydrolysis is known in literatures such as H. Ebiike, et. al., Tetrahedron Letters, 32, 5805 (1991). Suitable Z¹ groups may include acyloxymethyl groups such as pivaloyl methyl and propionylmethyl. The enzymatic hydrolysis may be carried out in an organic solvent, preferably a water saturated ethereal solution such as isopropyl ether, t-butyl methyl ether or diethyl ether. This reaction may be carried out at a temperature of 0° C. to 60° C., preferably from 30° C. to 45° C. for 10 minutes to 4 weeks, preferably 1 days to 2 weeks.

Preparation Method B-IV (enantioselective Hantzsch cyclization)

The compound (II) may be obtained using enantioselective Hantzsch cyclization. This cyclization may be made by a condensation with either enone or enamine attached chiral auxiliaries. The main literature (Tet.Letts,(1988),6437) precedent for this process involves the Enders SAMP/RAMP-methodology (chiral hydrazone tautomer of enamine). Other varients exists in the patent literature (Bayer's DE 87/3714438 and DE 84/3423105) involving a chiral enamine formed from t-butylvaline.

Further, the compounds (II-a) may be prepared by several methods as indicated in the following Preparation Methods C-I to C-III.

Preparation Method C-I:

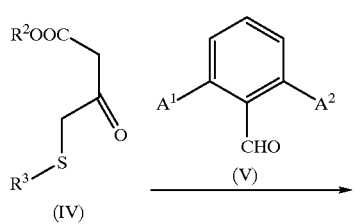

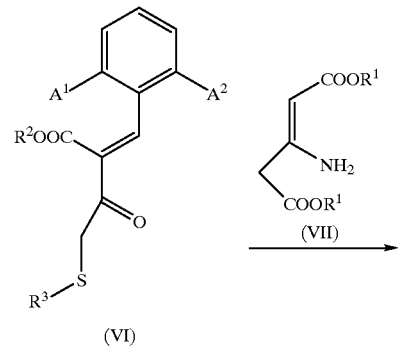

(VI)  (VII)

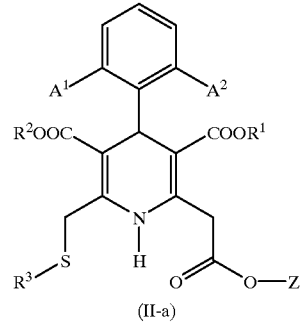

(II-a)

(wherein all the symbols are already defined)

This method utilizes the modified Hantzsch synthesis as described in A. Sausins and G. Duburs, *Heterocycles*, 1988, 27, 269. In this method, beta-keto ester (IV) is first reacted with substituted benzaldehyde (V) to obtain compound (VI). This reaction may be carried out in a suitable reaction-inert solvent. Suitable solvents include, for example, aqueous or non-aqueous organic solvents (e.g., tetrahydrofuran, dioxane, acetone, dimethoxyethane and acetonitrile); halogenated hydrocarbons such as chloroform, dichloroethane. This reaction may be carried out at a temperature of 0° C. to 150° C., preferably from 40° C. to 80° C. for 10 min. to 24 hours, preferably 30 min. to 3 hours.

Thereafter, compound (VI) as obtained above is reacted with compound (VII) in the presence of, or absence of a suitable condensing agent such as Lewis acids, to obtain the 1,4-dihydropyridine compound of the formula (II-a). This reaction may be carried out in the presence of, or absence of the reaction-inert solvent. Suitable solvents include, for example, aqueous or non-aqueous organic solvents (e.g., tetrahydrofuran, dioxane, acetone, dimethoxyethane and acetonitrile); halogenated hydrocarbons such as chloroform, dichloroethane. However, this reaction may be preferably carried out in the absence of a solvent. This reaction may be carried out at a temperature of 0° C. to 200° C., preferably, from 60° C. to 150° C. for 30 minutes to 48 hours, preferably 10 hours to 20 hours.

In addition, the beta-keto esters (IV) and the substituted benzaldehydes (V) which can be used herein may be either already known or may be prepared by known methods. For example, the beta-keto esters (IV) may be prepared according to the reported methods as shown in, for example, (1) D. Scherling, *J. Labelled Compds. Radiopharm.*, 1989, 27, 599; (2) C. R. Holmquist and E. J. Roskamp, *J. Org. Chem.*, 1989, 54, 3258; (3) S. N. Huckin and L. Weiler, *J. Am. Chem. Soc.*, 1974, 96, 1082; (4) *J. C. S. Perkin I*, 1979, 529; and (5) *Synthesis* 1986, 37; *J. C. S. Chem. Commun.*, 1977, 932).

Preparation Method C-II:

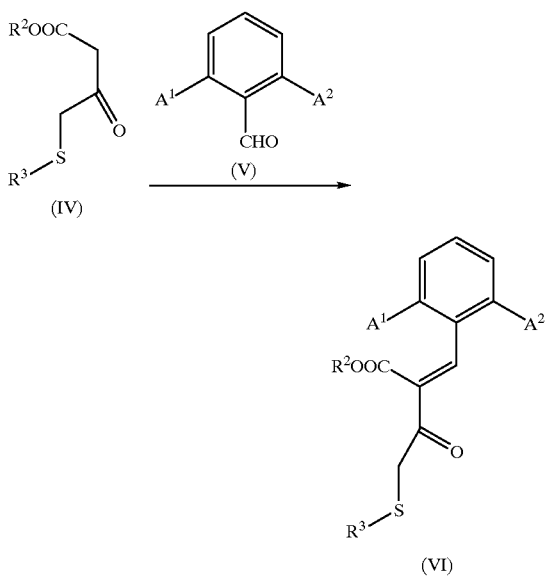

(wherein all the symbols are as already defined)

This method utilizes the three components Hantzsch reaction. In a typical procedure, the beta-keto ester (IV), the substituted benzaldehyde (V) and compound (VII) may be heated together in a suitable reaction-inert solvent. Suitable solvents include, for example, aqueous or non-aqueous organic solvents (e.g., tetrahydrofuran, dioxane, acetone, dimethoxyethane and acetonitrile); halogenated hydrocarbons such as chloroform, dichloroethane; and lower alkanols such as methanol and ethanol (preferably lower alkanols such as methanol and ethanol). Preferably, a small amount of a lower alkanoic acid such as acetic acid is added as catalyst. The reaction mixture may be heated at 50° C. to 200° C., preferably from 70° C. to reflux temperature for 30 minutes to 1 week.

Preparation Method C-III:

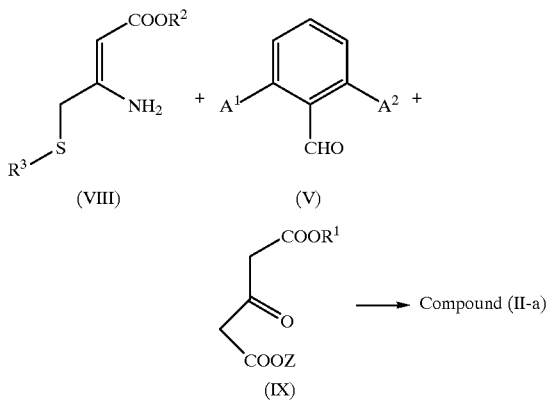

(wherein all the symbols are as already defined)

This method also utilizes three components Hantzsch reaction as mentioned above. The reaction conditions similar to the above can be also used in this method.

Compound (VIII), enamine may either be known compounds or may be prepared by known methods. For example, the enamine compounds (VIII) may be prepared by reacting the beta-keto ester (IV) with ammonia or ammonium salt. More specifically, the beta-keto ester (IV) may be dissolved in a suitable solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane. Excess amount of ammonia gas is introduced into the solution at a temperature of 0 to 60° C. Alternatively, a solution containing ammonia dissolved in the above solvent is added to the solution containing the beta-keto ester (IV), and the resultant mixture is reacted at a temperature of 0 to 60° C., to obtain compound (VIII).

Alternatively, compound VIII may be prepared by a treatment with ammonium salt, preferably ammonium acetate in reaction inert solvet such as DMF or DMSO, preferably DMF at room temperature to 100° C., preferably 50° C. to 70° C. for 30 minutes to 6 hours, preferably 1 to 3 hours.

The present invention includes salt forms of the compounds (I) as obtained above.

Insofar as the dihydropyridine compounds of this invention are basic compounds, they are capable of forming a wide variety of different salts with various inorganic and organic acids.

The acids which are used to prepare the pharmaceutically acceptable acid addition salts of the aforementioned dihydropyridine base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts. The acid addition salts can be prepared by conventional procedures.

The dihydropyridine compounds of the present invention of formula (I) exhibit significant bradykinin receptor-binding activity and therefore, are of value in the treatment of a wide variety of clinical conditions in mammals, especially man. Such conditions include inflammation, cardiovascular disease, pain, common cold, allergies, asthma, pancreatitis, burns, virus infection, head injury, multiple trauma and the like.

Therefore, these compounds are readily adapted to therapeutic use as bradykinin antagonists for the control and/or treatment of any of the aforesaid clinical conditions in mammals, including humans.

The activity of the dihydropyridine compounds of the present invention, as bradykinin antagonists, is determined by their ability to inhibit the binding of bradykinin at its receptor sites in IMR90 cells which express B2 receptor employing radioactive ligands.

The bradykinin antagonist activity of the dihydropyridine compounds is evaluated by using the standard assay procedure described in, for example, Baenziger N. L., Jong Y-J. I., Yocum S. A., Dalemar L. R., Wilhelm B., Vaurek R., Stewart J. M., Eur. J. Cell Biol., 1992, 58, 71–80. This method essentially involves determining the concentration of the individual compound required to reduce the amount of radiolabelled bradykinin ligands by 50% at their receptor sites in rat, guinea pig or monkey tissues, or A431 or IMR90 cells, thereby affording characteristic $IC_{50}$ values for each compound tested.

More specifically, the assay is carried out as follows. First, rat, guinea pig or monkey ileum tissues are minced and suspended in 25 mM piperazine-N,N'-bis (2-ethanesulfonic acid (PIPES) buffer (pH 6.8) containing 0.1 mg/ml of soybean trypsin inhibitor. Then, the tissues are homogenized using a Polytron homogenizer at setting #6 for 30 seconds, and centrifuged at 30,000×g for 20 minutes. The pellets are homogenized with the same buffer, and recentrifuged. The tissue pellets, IMR90 cells are suspended in 25 mM PIPES buffer (pH6.8) containing 1.25 mM dithiothreitol, 1.75 µg/ml bacitracin, 125 µM o-phenanthroline, 6.25 µM captopril, 1.25 mg/ml bovine serum albumin (BSA), to prepare tissue/cell suspensions. Then, 10 µl of test compound solution dissolved in phosphate buffered saline (PBS, pH 7.5) containing 2% DMSO (final) and 0.1% BSA (w/v) or 10 ml of 12.5 mM bradykinin in PBS (pH 7.5) containing 0.1% BSA(w/v) are placed in a reaction 96-well plate. 15 µl of 8.3 nM [3H]bradykinin are added to the compound solution or bradykinin solution in the 96-well plate. Finally 100 µl of the tissue or cell suspension are added to the mixture in the plate, and incubated at 25° C. for 1 hour. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$Bound = Bmax/(1+[I]/IC_{50})$$

wherein [I] means the concentration of the test compound.

All compounds prepared in the working examples as described below were tested by this method, and showed an $IC_{50}$ value of 0.3 nM to 50 nM in IMR-90 cell line with respect to inhibition of binding at its receptor.

The bradykinin antagonist activity of the dihydropyridine compounds in vivo is evaluated by a plasma leakage test. This test essentially involve determining the concentration of the individual compound required to reduce by 50% the amount of bradykinin-induced plasma leakage in rat urinary bladder, thereby affording characteristic $ED_{50}$ values for each compounds tested.

More specifically, the assay is carried out as follows. 3.5-week old male Sprague-Dawlew rats are purchased from Charles River Japan Inc. The rats are fed on stock diet (CRF from Charles River Japan, Inc.) and maintained under the standard conditions (temperature, 23±1° C. and humidity 55±5%) for at least 3 days. The rats are fasted overnight prior to the experiments. Each test group consists of 5 rats.

Bradykinin, purchased from Peptide Ins., is dissolved in the physiological saline (0.9% sodium chloride) at a concentration of 10 nmol/ml. The test dihydropyridine compounds are dissolved or suspended at different concentrations in the physiological saline solution containing 10 mg/ml Evans blue (Wako Pure Chemical, Japan).

Captopril (5 mg/kg of body weight) is intraperitoneally (i.p.) injected to the rats, and 20 min later the rats are anesthetized by an administration of Nembutal (Abbott) (2.5 mg/kg of body weight). 5 min later, the test compound solution containing Evans blue is intravenously (i.v.) injected to the rats at a dose of 3 ml/kg of body weight. Another 5 min later, bradykinin is i.v. injected at a dose of 10 nmol/kg body weight. Thereafter, the rats are killed by dislocation of the neck and the urinary bladders are obtained. The urinary bladders are individually treated with 1 ml of formamide at 60° C. for at least 16 hours to extract Evans blue from the tissue. The absorbance of the extract is measured spectrophotometrically at 605 nm to determined the dye concentration. The effect of the individual test compound is calculated as a percentage of the amount of Evans blue leaked into the urinary bladder as compared to the control (saline for the test compounds). Some compounds prepared in the working examples as described below exhibited a remarkable activity at a concentration of 0.2 mg/kg in the inhibition of urinary bladder leakage in this test system, whereas the corresponging enantiomer (such as (4S), [6-(S)-phenylsulfinyl]-1,4-dihydropyridine compounds) did not show significant in vivo activity at a concentration of 10 mg/kg.

The dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intraarticular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane or from t-butanol (1.28 ppm in $D_2O$). The peak shapes are denoted as follows: s, singlet; d, doublet; t, triplet; m, multiplet; br, broad.

Example 1

(−)-(4S)-Dimethyl 4-(2,6-Dichlorophenyl)-2-[4-(8-methyl-8-azibicyclo[3.2.1]oct-3-yl)-1-piperazinyl]carbonylmethyl-6-(S)-phenylsulfinylmethyl-1,4-dihydropyridine-3,5-dicarboxylate dicitrate A. Methyl 2-(2,6-Dichlorophenylmethylidene)-3-oxo-4-phenylthiobutanoate (1)

Sodium hydride (17.32 g, 0.433 mol) was washed with hexane (100 ml×2) then was suspended in dimethylformamide (300 ml). To the mixture was dropwise added thiophenol (44.5 ml, 0.433 mol) in DMF (50 ml ) under ice-methanol bath cooling with controlling the inner temperature of 5–10° C. under nitrogen atmosphere. After 1.5 h stirring at −5° C., methyl 4-chloroacetoacetate (50 ml, 0.433 mol) was dropwise added to the reaction mixture under ice-methanol bath cooling with controlling the inner temperature of 5–10° C. under nitrogen atmosphere and the reaction mixture was stirred at room temperature overnight. The mixture was acidified with 1N HCl to pH 2 under ice bath cooling then partitioned between EtOAc (500 ml) and $H_2O$ (100 ml). The aqueous phase was extracted with EtOAc (250 ml×2). The combined extracts were concentrated to about 500 ml and then washed with aq. $NaHCO_3$ solution (150 ml) and brine (100 ml×3). The organic solution was dried over $MgSO_4$ and concentrated to afford 100.88 g of methyl 4-phenylthioacetoacetate as an orange color oil. (104% yield).(contained ⅙ eq of DMF)

$^1$H NMR ($CDCl_3$) δ7.42–7.18 (m, 5H), 3.80 (s 2H), 3.71 (s, 3H), 3.65 (s, 2H).

To the oil was added 2,6-dichlorobenzaldehyde (75.9 g, 0.433 mol), acetic acid (5.5 ml g, 96 mmol), piperidine (5.5 ml, 55.6 mmol) and benzene (300 ml). This mixture was distilled for removal of the initial distillate (about 50 ml) then replaced the distillation apparatus to Dean Stark trap and refluxed with azeotropic removal of water for 2 h. The mixture was diluted with EtOAc (500 ml) and washed with 1N HCl (100 ml), sat. $NaHCO_3$ (100 ml) solution and then brine (100 ml×3) The organic solution was dried over $MgSO_4$ and concentrated in vacuo to give a yellow oil which was purified by a silica gel column chromatography (2 Kg, hexane/ethyl acetate: 50/1, 10/1, then 5/1 as eluent) to give 136.63 g (82.8%) of a benzylidene derivative. This is a 3:1 mixture of the double bond isomers.

$^1$H NMR ($CDCl_3$) δ7.72 (s, 0.25H), 7.66 (s, 0.75H), 7.17–7.40 (m, 8H), 4.12 (s, 1.5H), 4.02 (s, 0.5H), 3.82 (s, 0.75H), 3.64 (s, 2.25H). IR(neat): 1720, 1690 $cm^{-1}$.

B. Dimethyl 4-(2,6-Dichlorophenyl)-2-methoxycarbonylmethyl-6-phenylthiomethyl-1,4-dihydropyridine-3,5-dicarboxylate A mixture of methyl 2-(2,6-dichlorophenylmethylidene)-3-oxo-4-phenylthiobutanoate (2) (136.57 g, 358 mmol) and dimethyl 3-aminoglutaconate (61.94 g, 358 mmol) was placed in a 500 ml three necked flask equipped with mechanical stirrer, Dean Stark trap and a thermometer. The mixture was heated at 120° C. (bath temp) for 22.5 h (inner temp was 110–116° C.). After cooling down to room temperature, the reaction mixture was purified by column chromatography on silica gel (500 g, hexane/ethyl acetate: 10/1, 4/1, 2/1 then 1/1 as eluent) to afford 110 g of a brown oil. This oil was purified by a silica gel column (550 g, hexane/EtOAc: 50/1 to 2/1 as eluent) to give 76.24 g (39.7%) of a wine red color viscous oil.

$^1$H NMR ($CDCl_3$) δ7.69 (br. s, 1H), 7.21–7.41 (m, 7H), 6.99 (dd, J=7.7, 8.4 Hz, 1H), 5.98 (s, 1H), 4.52 (d, J=16.5 Hz, 1H), 4.23 (d, J=16.5 Hz, 1H), 3.86 (d, J=16.5 Hz, 1H), 3.66 (s, 3H), 3.61 (d, J=16.5 Hz, 1H), 3.53 (s, 3H), 3.52 (s, 3H), IR(neat): 3350, 1740, 1700, 1650, 1625 $cm^{-1}$.

C. Dimethyl 4-(2,6-Dichlorophenyl)-2-methoxycarbonylmethyl-6-phenylsulfinylmethyl-1,4-dihydropyridine-3,5-dicarboxylate To a stirred solution of dimethyl 4-(2,6-dichlorophenyl)-2-methoxycarbonylmethyl-6-phenylthiomethyl-2(226.09 g, 422 mmol) and $K_2CO_3$ (58.30 g, 422 mmol) in acetone (1000 ml) and water (100 ml) was portionwise added 80% 3-chloroperoxybenzoic acid (90.23 g, 418 mmol) at inner temperature of −68—−65° C. during a period of 50 minutes. After 1 h stirring at −68—−65° C., the reaction mixture was diluted with AcOEt (10 l) and water (1.0 l) and the organic layer was washed with aqueous saturated $NaHCO_3$ solution (1.0 l), and brine (1.0 l×3). After the solution was dried over $MgSO_4$, the solvent was evaporated to give a yellow amorphous solid (228.00 g) as a diastereomeric mixture (1.0:8.0 of undesired/desired isomers). Crystallization of the crude product from IPE and toluene gave a yellow crystalline solid (140.31 g, 60%, 1.0:14.1 of undesired/desired product). The mother liquid was concentrated in vacuo (87 g) and purified by a silica gel column chromatography (500 g) eluted with EtOAc/hexane: 1/9 to 2/1) to give a yellow oil. Crystallization of the oil from EtOAc and IPE gave a yellow crystalline solid (23.67 g, 10%, 1.0:5.1 of undesired/desired isomers). These two crops were used in the subsequent reaction without further purification.

$^1$H NMR ($CDCl_3$) δ7.76–7.64 (m, 3H), 7.60–7.49 (m, 3H), 7.26 (d, J=8.1 Hz, 2H), 7.01 (t, J=8.1 Hz, 1H), 5.90(s, 1H), 4.57 (d, J=13.5 Hz, 1H), 4.06 (d, J=13.5 Hz, 1H), 3.95 (d, J=16.8 Hz, 1H), 3.75 (s, 3H), 3.53 (s, 3H), 3.50 (d, J=16.8 Hz, 1H), 3.47 (s, 3H).

D. [3,5-Dimethoxycarbonyl-4-(2,6-dichlorophenyl)-6-phenylsulfinylmethyl-1,4-dihydropyridin-2-yl]acetic acid To a stirred solution of the ester (14.4 g, 26.09 mmol) in dioxane (190 ml) 2N NaOH (26 ml, 52.18 mmol) was added at room temperature and stirred for 30 min. The mixture was washed with a mixed solvent of AcOEt (200 ml) and hexane (50 ml), then acidified with 2N HCl-ice and extracted with $CH_2Cl_2$ (200 ml), the $CH_2Cl_2$ layer was washed with brine, dried over $MgSO_4$ then evaporated to give a yellow solid (14 g, 100%).

$^1$H NMR ($CDCl_3$) δ8.37 (br.s, 1H), 7.74–7.80 (m, 2H), 7.49–7.57 (m, 3H), 7.27 (d, J=8.1 Hz, 2H), 7.03 (t, J=7.9 Hz,

1H), 6.02 (s, 1H), 4.74 (d, J=12.8 Hz, 1H), 3.98 (d, J=16.1 Hz, 1H), 3.91 (d, J=12.8 Hz, 1H), 3.73 (d, J=12.8 Hz, 1H), 3.59 (s, 3H), 3.53 (s, 3H).

To a suspension of the acid (14 g, 26.09 mmol) in IPA (400 ml) and ethanol (100 ml) was added (+)-cinchonine (7.67 g, 26.09 mmol). The mixture was filtrated and the filtrate was allowed to stand in a refrigerator for 2 days. The yellow precipitate was collected by suction filtration to give a yellow solid (4.3 g, 20% yield). The filtrate was concentrated to about one third of the volume. During the concentration of the filtrate by a rotary evaporator, a large amount of the cinchonine salt was formed. The mixture was allowed to stand in a refrigerator overnight and collected by suction filtration to give the second crop. (4.26 g, 19.7%). Both salts were mostly a single enantiomer (>98%ee). The first crop, second crop and a product from the corresponding pilot experiment were combined (9.59 g, 11.5 mmol) and recrystallized from IPA to give the pure product (6.56 g)

The corresponding enantiomer was also obtained by a following procedure. The filtrate, after the second crystallization above, was concentrated in vacuo. The residue was partitioned between 2N HCl (10 ml) and EtOAc (200 ml). The organic layer was washed with $H_2O$ (50 ml), dried ($MgSO_4$) and concentrated in vacuo to give a yellow amorphous solid. This was dissolved in IPA and then cinchonidine (4.602 g, 15.65 mmol) was added. The mixture was allowed to stand in a refrigerator overnight to give a yellow solid (7.5 g, 34.6%). This salt was mostly pure enantiomer with ee of >98%. Recrystallization of the salt (7.5 g, 9.0 mmol) from methanol followed by washed with IPA gave the pure product (4.17 g). Second crop was also obtained from the mother liquid. (781 mg)

(+)cinchonine salt
$[\alpha]_D^{24}$=−103.9 (c=1.02, MeOH)
(−)-cinchonidine salt
$[\alpha]_D^{24}$=+109.68 (c=0.992, MeOH)

The cinchonine salt (83.2 mg, 0.1 mmol) was partitioned between EtOAc (15 ml) and 2N HCl (2 ml). The organic layer was washed with brine (2 ml×2), dried ($MgSO_4$) and concentrated in vacuo to give a yellow amorphous solid (53.8 mg).
$[\alpha]_D^{24}$=136.8 (c=1.076, MeOH)

Similarly, cinchonidine salt (83.2 mg, 0.1 mmol) was partitioned between EtOAc and 1N HCl. The organic layer was washed with brine, dried and concentrated in vacuo to give a yellow amorphous solid (46.9 mg).
$[\alpha]_D^{27}$=+133.5 (c=0.938, MeOH)

E. (−)-(4S)-Dimethyl 4-(2,6-Dichlorophenyl)-2-[4-(8-methyl-8-azabicyclo[3.2.1]oct-3-yl)-1-piperazinyl]carbonylmethyl-6-(S)-phenylsulfinylmethyl-1,4-dihydropyridine-3,5-dicarboxylate dicitrate To a solution of the (−)-acid (2.53 g, 5.32 mmol) in dry $CH_2Cl_2$ (10 ml) was added N-1-ethyl-3-(3-dimethylaminopropyl)carbodiimide hydrochloride (1.53 g, 7.98 mmol) at 0° C. and stirred at 0° C. for 30 min under nitrogen atmosphere. To a suspension of 1-(8-methyl-8-azabicyclo[3.2.1]oct-3-yl)piperazine trihydrochloride (2.53 g, 7.98 mmol) in $CH_2Cl_2$ (20 ml) was added triethylamine (3.4 ml, 23.9 mmol). The mixture was turned to a clear solution, then this solution was added to the activated ester solution above.

The mixture was stirred at ambient temperature under nitrogen atmosphere overnight. The mixture was partitioned between $H_2O$ (10 ml) and $CH_2Cl_2$ (40 ml). The organic layer was washed with brine (10 ml), dried ($MgSO_4$) and concentrated in vacuo to give a yellow oil. Crystallization from EtOAc gave a yellow solid. Chromatography on $NH_2$-propyl gel (120 g) eluted with $CH_2Cl_2$/methanol (100/1 to 30/1) gave a yellow oil (3.2 mg).

$^1$H-NMP (CDCl$_3$) δ8.28 (br.s, 1H), 7.82–7.70 (m, 2H), 7.58–7.33 (m, 3H), 7.26 (d, J=8.1 Hz, 2H), 7.02 (dd, J=8.4, 7.3 Hz, 1H), 5.98 (s, 1H), 4.54 (d, J=12.8 Hz, 1H), 4.10–3.70 (m, 3H), 3.52 (s, 6H), 3.25–3.10 (m, 2H), 2.75–2.35 (m, 6H), 2.27 (s, 3H), 2.09–1.85 (m, 2H), 1.75–1.40 (m, 6H).

The oil (1.13 g, 1.55 mmol) and citric acid (300.5 mg, 1.43 mmol) were dissolved in methanol (9 ml), then filtered. The filtrate was evaporated and resulting residue was crystallized from EtOH-Et$_2$O to give the corresponding salt (618 mg, 43%).

$[\alpha]_D^{26}$−127 (c=0.90, MeOH) mp 152.5–155.0° C. (decomposed). IR(KBr)3455, 3405, 3345, 3315, 1726, 1693, 1645, 1630, 1615, 1601, 1595 cm$^{-1}$ $^1$H-NMR (DMSO-d6) δ9.25 (s, 1H), 7.82–7.52 (m, 5H), 7.37 (d, J=8.1 Hz, 2H), 7.19 (t, J=7.8 Hz, 1H), 5.92 (s, 1H), 4.42 (d, J=12.1 Hz, 1H), 4.00 (d, J=16.1 Hz, 1H), 3.85 (br.s, 2H), 3.70 (d, J=12.1 Hz, 1H), 3.46 (s, 3H), 3.39 (s, 3H), 3.68–1.68 (m).

Example 2

(−)-(4S)-Dimethyl 4-(2,6-Dichlorophenyl)-2-[4-(2-(1-pyrrolidinoethyl)-1-piperazinylcarbonylmethyl)]-6-(S)-phenylsulfinylmethyl-1,4-dihydropyridine-3,5-dicarboxylate Dihydrochloride This was prepared by a procedure similar to that described in Example 1-E, as a pale yellow solid.

mp 180.0–181.9° C. (decomposed) $[\alpha]_D^{27}$−150 (c=0.87, MeOH) IR(KBr) 3430, 3370, 3265, 2995, 1691, 1667, 1659, 1650, 1644, 1634, 1507, 1194 cm$^{-1}$ $^1$H-NMR (DMSO-d6) δ9.61–9.26 (m, 1H), 7.82–7.69 (m, 2H), 7.69–7.50 (m, 3H), 7.38 (d, J=8.1 Hz, 2H), 7.19 (t, J=8.1 Hz, 1H), 5.94 (s, 1H), 4.60–2.72 (m, 20H), 3.46 (s, 3H), 3.41 (s, 3H), 2.20–1.70 (m, 4H).

free base $^1$H-NMR (CDCl$_3$) δ8.20 (br.s, 1H), 7.79–7.72 (m, 2H), 7.58–7.47 (m, 3H), 7.27 (d, J=7.7 Hz, 2H), 7.02 (t, J=7.7 Hz, 1H), 5.97 (s, 1H), 4.56 (d, J=12.8 Hz, 1H), 4.02–3.74 (m, 3H), 3.72–3.56 (m, 4H), 3.53 (s, 6H), 2.68–2.35 (m, 12H), 1.85–1.66 (m, 4H).

Example 3

(−)-(4S)-Dimethyl 4-(2,6-Dichlorophenyl)-2-[4-(8-acetyl-8-azabicyclo[3.2.1]oct-3-yl)-1-piperazinylcarbonylmethyl]-6(S)-phenylsulfinylmethyl-1,4-dihydropyridine-3,5-dicarboxylate monohydrochloride This was prepared by a procedure similar to that described in Example 1-E, as a pale yellow solid.

mp 188–189° C. (decomposed) $[\alpha]_D^{26}$−137.7 (c=0.70, MeOH) IR(KBr) 3420, 3380, 1690, 1659, 1641, 1631, 1622, 1290 cm$^{-1}$ $^1$H-NMR (DMSO-d6) δ11.28–10.88 (m), 9.57–9.28 (m, 1H), 7.88–7.70 (m, 2H), 7.70–7.52 (m, 3H), 7.48–7.29 (m, 2H), 7.19 (t, J=7.7 Hz, 1H), 5.93 (s, 1H), 4.65–2.65 (m), 3.47 (s, 3H), 3.41 (s, 3H), 1.99 (s, 3H), 2.21–1.50 (m).

free base $^1$H-NMR (CDCl$_3$) δ8.25 (br.s, 0.5H), 8.19 (s, 0.5H), 7.83–7.66 (m, 2H), 7.60–7.40 (m, 3H), 7.32–7.15 (m, 2H), 7.09–6.91 (m, 1H), 5.99 (s, 1H), 4.80–4.62 (m, 1H), 4.58 (d, J=12.5 Hz, 0.5H), 4.57 (d, J=12.8 Hz, 0.5H), 4.24–3.72 (m, 4H), 3.53 (s, 6H), 2.89–1.31 (m), 2.04 (s, 3H).

Example 4

(−)(4S)-Dimethyl 4-(2,6-Dichlorophenyl)-2-[4-(8-ethyl-8-azabicyclo[3.2.1]oct-3-yl)-1-piperazinylcarbonylmethyl]-6-(S)-phenylsulfinylmethyl-1,4-dihydropyridine-3,5-dicarboxylate Dihydrochloride This was prepared by a procedure similar to that described in Example 1-E, as a pale yellow solid.

mp 210–213° C. (decomposed) $[\alpha]_D^{26}$–145.1 (c=0.74, MeOH) IR(KBr) 3415, 3380, 1688, 1658, 1644, 1631, 1623, 1291 cm$^{-1}$ $^1$H-NMR (DMSO-d6) δ10.78–10.40 (m), 9.60–9.24 (m, 1H), 7.82–7.68 (m, 2H), 7.68–7.51 (m, 3H), 7.38 (d, J=8.0 Hz, 2H), 7.19 (t, J=8.0 Hz, 1H), 5.93 (s, 1H), 3.46 (s, 3H), 3.41 (s, 3H), 1.27 (t, J=7.0 Hz, 3H), 4.60–1.70 (m).

free base $^1$H-NMR (CDCl$_3$) δ8.20 (br.s, 1H), 7.82–7.69 (m, 2H), 7.62–7.43 (m, 3H), 7.26 (d, J=7.7 Hz, 2H), 7.02 (t, J=7.7 Hz, 1H), 5.98 (s, 1H), 4.55 (d, J=12.8 Hz, 1H), 4.03–3.74 (m, 3H), 3.53 (s, 6H), 3.72–3.46 (m), 3.39–3.28 (m, 2H), 2.68–2.28 (m), 2.00–1.82 (m), 1.75–1.40 (m).

Example 5

(−)-(4S)-Dimethyl 4-(2,6-Dichlorophenyl)-2-[4-(8-isopropyl-8-azabicyclo[3.2.1]-oct-3-yl)-1-piperazinylcarbonylmethyl]-6-(S)-phenylsulfinylmethyl-1,4-dihydropyridine-3,5-dicarboxylate Dihydrochloride This was prepared by a procedure similar to that described in Example 1-E, as a pale yellow solid.

mp 210–212° C. (decomposed) $[\alpha]_D^{26}$–150.4 (c=1.15, MeOH) IR(KBr) 3410, 1691, 1660, 1645, 1631, 1103 cm$^{-1}$ $^1$H-NMR (DMSO-d6) δ12.36–11.40 (m), 10.85–10.31 (m), 9.60–9.19 (m), 7.82–7.68 (m, 2H), 7.68–7.50 (m, 3H), 7.37 (d, J=8.1 Hz, 2H), 7.19 (t, J=8.1 Hz, 1H), 5.93 (s, 1H), 4.60–1.70 (m), 3.46 (s, 3H), 3.41 (s, 3H), 1.46–1.21 (m).

free base $^1$H-NMR (CDCl$_3$) δ8.22 (br.s, 1H), 7.83–7.70 (m, 2H), 7.60–7.42 (m, 3H), 7.26 (d, J=8.1 Hz, 2H), 7.02 (t, J=8.4 Hz, 1H), 5.99 (s, 1H), 4.55 (d, J=12.8 Hz, 1H), 4.03–3.40 (m), 3.53 (s, 6H), 2.94–2.75 (m, 1H), 2.66–2.37 (m, 5H), 2.14–1.31 (m), 1.07 (d, J=6.2 Hz, 6H).

Example 6

(−)-(4S)-Dimethyl 4-(2,6-Dichlorophenyl)-2-[4-(3-(1-pyrrolidinopropyl)-1-piperazinylcarbonylmethyl)]-6-(S)-phenylsulfinylmethyl-1,4-dihydropyridine-3,5-dicarboxylate Dihydrochloride This was prepared by a procedure similar to that described in Example 1-E, as a pale yellow solid.

mp 189–192° C. (decomposed) $[\alpha]_D^{27}$–160.7 (c=1.04, MeOH) IR(KBr) 3430, 3305, 3095, 1691, 1660, 1645, 1633, 1622, 1513, 1196, 1154 cm$^{-1}$ $^1$H-N(DMSO-d6) δ11.68–11.30 (m), 11.08–10.71 (m), 9.65–9.25 (m), 7.85–7.70 (m, 2H), 7.70–7.50 (m, 3H), 7.38 (d, J=7.7 Hz, 2H), 7.19 (t, J=7.7 Hz, 1H), 5.94 (s, 1H), 4.55–2.65 (m, 20H), 3.46 (s, 3H), 3.40 (s, 3H), 2.31–1.55 (m, 6H).

free base $^1$H-NMR (CDCl$_3$) δ8.23 (br.s, 1H), 7.88–7.65 (m, 2H), 7.60–7.40 (m, 3H), 7.26 (d, J=7.7 Hz, 2H), 7.01 (t, J=7.7 Hz, 1H), 5.99 (s, 1H), 4.53 (d, J=12.8 Hz, 1H), 4.08–3.31 (m, 7H), 3.53 (s, 6H), 2.60–2.21 (m, 12H), 1.85–1.50 (m, 6H).

Example 7

(−)-(4S)-Dimethyl 4-(2,6-Dichlorophenyl)-2-[4-(8-benzyl-8-azabicyclo[3.2.1]oct-3-yl)-1-piperazinylcarbonylmethyl]-6-(S)-phenylsulfinylmethyl-1,4-dihydropyridine-3,5-dicarboxylate Dihydrochloride This was prepared by a procedure similar to that described in Example 1-E, as a pale yellow solid.

mp 210–213° C. (decomposed) $[\alpha]_D^{25}$–138.0 (c=0.91, MeOH) IR(KBr) 3390, 3360, 1691, 1660, 1645, 1632, 1623, 1197, 1191, 1179 cm$^{-1}$ $^1$H-NMR (DMSO-d6) δ12.50–12.30 (m), 1.80–11.40 (m), 11.30–10.80 (m), 9.60–9.21 (m), 8.00–7.88 (m, 1H), 7.82–7.68 (m, 2H), 7.68–7.52 (m, 3H), 7.38 (d, J=8.1 Hz, 2H), 7.19 (t, J=7.3 Hz, 1H), 5.92 (s, 1H), 4.88–4.06 (m), 3.46 (s, 3H), 3.38 (s, 3H), 4.00–1.70 (m).

free base $^1$H-NMR (CDCl$_3$) δ8.23–8.20 (m, 1H), 7.80–7.71 (m, 2H), 7.59–7.45 (m, 3H), 7.42–7.17 (m, 7H), 7.02 (dd, J=8.4, 7.9 Hz, 1H), 5.98 (s, 1H), 4.54 (d, J=12.8 Hz, 1H), 4.00–3.78 (m, 3H), 3.76–3.42 (m, 2H), 3.54 (s, 3H), 3.53 (s, 3H), 3.32–3.11 (m, 2H), 2.64–2.37 (m, 6H), 2.32–1.84 (m, 5H), 1.78–1.40 (m, 6H).

Example 8

(−)-(4S)-Dimethyl 4-(2,6-Dichlorophenyl)-2-[4-ethoxycarbonyl piperazinylcarbonylmethyl]-6-(S)-phenylsulfinylmethyl-1,4-dihydropyridine-3,5-dicarboxylate Dihydrochloride This was prepared by a procedure similar to that described in Example 1-E, as a pale yellow solid.

mp 172–174° C. (decomposed) $[\alpha]_D^{25}$–180° (c=0.93, MeOH) IR(KBr) 3410, 3385, 3285, 1743, 1691, 1643, 1577, 1155 cm$^{-1}$ $^1$H-NMR (DMSO-d6) δ9.45 (br.s, 1H), 7.82–7.69 (m, 2H), 7.69–7.52 (m, 3H), 7.37 (d, J=7.7 Hz, 2H), 7.19 (dd, J=8.4, 7.3 Hz, 1H), 5.93 (s, 1H), 4.41 (d, J=12.1 Hz, 1H), 3.46 (s, 3H), 3.41 (s, 3H), 4.60–2.60 (m, 15H), 1.25 (t, J=7.0 Hz, 3H).

free base $^1$H-NMR (CDCl$_3$) δ8.17 (br.s, 1H), 7.82–7.70 (m, 2H), 7.60–7.48 (m, 3H), 7.27 (d, J=8.0 Hz, 2H), 7.01 (dd J=8.4, 7.3 Hz, 1H), 5.97 (s, 1H), 4.54 (d, J=12.8 Hz, 1H), 4.19 (q, J=7.3 Hz, 2H), 3.98 (d, J=15.8 Hz, 1H), 3.87 (d, J=12.8 Hz, 1H), 3.83 (d, J=15.8 Hz, 1H), 3.53 (s, 3H), 3.52 (s, 3H), 3.22 (s, 2H), 2.70–2.48 (m, 4H), 1.27 (t, J=7.0 Hz, 3H).

Example 9

(4S)-Dimethyl 4-(2,6-Dichlorophenyl)-2-(4-cyclohexylmethyl-1-piperazinyl)carbonylmethyl-6-[(S)-phenylsulfinylmethyl]-1,4-dihydropyridine-3,5-dicarboxylate, Monohydrochloride This was prepared by a procedure similar to that described in Example 1-E, as a pale yellow solid.

mp 165.1–166.5° C. (decomposed) $[\alpha]_D^{25}$–170.2 (c=0.49, MeOH) $^1$H-NMR (DMSO-d6, HCl salt): δ7.82–7.54 (m, 6H), 7.38 (d, J=8.1 Hz, 2H), 7.19 (t, J=8.1 Hz, 1H), 5.93 (s, 1H), 4.50–2.72 (m, 14H), 3.46 (s, 3H), 3.40 (s, 3H), 1.90–0.85 (m, 11H). IR (KBr): 3440, 2935, 1691, 1642, 1633 cm$^{-1}$.

$^1$H-NMR (CDCl$_3$, free base): δ8.19 (br.s, 1H), 7.82–7.71 (m, 2H), 7.60–7.46 (m, 3H), 7.27 (d, J=8.1 Hz, 2H), 7.02 (t, J=8.1 Hz, 1H), 5.98 (s, 1H), 4.53 (d, J=12.8 Hz, 1H), 4.01–3.75 (m, 3H), 3.68–3.42 (m, 4H), 3.53 (s, 6H), 2.44–2.31 (m, 4H), 2.10 (t, J=7.5 Hz, 2H), 1.83–0.76 (m, 11H).

Example 10

(4S)-Dimethyl 4-(2,6-Dichlorophenyl)-2-[(R,S)-3-(dimethylamino)pyrrolidino]carbonylmethyl-6-[(S)-phenylsulfinylmethyl]-1,4-dihydropyridine-3,5-dicarboxylate, Monohydrochloride This was prepared by a procedure similar to that described in Example 1-E, as a pale yellow solid.

mp 165.0–168.0° C. (decomposed) $[\alpha]_D^{24}$ –176.3 (c=0.27, MeOH) $^1$H-NMR (DMSO-d6, HCl salt): δ9.44–9.28 (m, 1H), 7.81–7.53 (m, 5H), 7.38 (d, J=8.1 Hz, 2H), 7.19 (t, J=8.1 Hz, 1H), 5.93 (s, 1H), 4.48–4.33 (m, 1H), 4.09–3.16 (m, 8H), 3.46 (s, 3H), 3.39 (s, 3H), 2.77 (br.s, 6H), 2.50–2.00 (m, 2H) IR (KBr): 3435, 2955, 1691, 1625 cm$^{-1}$.

$^1$H-NMR (CDCl$_3$, free base): δ8.63–8.37 (m, 1H), 7.82–7.70 (m, 2H), 7.68–7.42 (m, 3H), 7.30–7.17 (m, 2H), 7.06–6.92 (m, 1H), 6.00–5.87 (m, 1H), 4.66–4.22 (m, 1H), 4.22–3.02 (m, 13H), 2.88–1.66 (m, 9H).

Example 11

(4S)-Dimethyl 4-(2,6-Dichlorophenyl)-2-[4-(4-aminocyclohexyl)-1-piperazinyl]carbonylmethyl-6-[(S)-phenylsulfinylmethyl]-1,4-dihydropyridine-3,5-dicarboxylate, Dihydrochloride A. (4S)-Dimethyl 4-(2,6-Dichlorophenyl)-2-[4-(t-butoxycarbonylamino)-1-cyclohexyl-1-piperazinyl] carbonylmethyl-6-[(S)-phenylsulfinylmethyl]-1,4-dihydropyridine-3,5-dicarboxylate Dihydrochloride This was prepared by a procedure similar to that described in Example 1-E, as a pale yellow solid.

$^1$H-NMR (CDCl$_3$): δ8.18 (br.s, 1H), 7.81–7.70 (m, 2H), 7.60–7.45 (m, 3H), 7.27 (d, J=8.1Hz, 2H), 7.02 (t, J=8.1 Hz, 1H), 5.98 (s, 1H), 4.71–4.40 (m, 1H), 4.54 (d, J=12.8 Hz, 2H), 3.97–3.45 (m, 7H), 3.54 (s, 3H), 3.53 (s, 3H), 2.60–2.16 (m, 5H), 1.91–1.42 (m, 8H), 1.44 (s, 9H).

B. (4S)-Dimethyl 4-(2,6-Dichlorophenyl)-2-[4-(4-aminocyclohexyl)-1-piperazinyl]carbonylmethyl-6-[(S)-phenylsulfinylmethyl]-1,4-dihydropyridine-3,5-dicarboxylate, Dihydrochloride This was prepared by a procedure similar to that described in Preparation 2-B, as a pale yellow solid.

mp: 212.0–213.5° C. (decomposed) $[\alpha]_D^{24}$ –153.7 (c=0.285, MeOH) mp: 212.0–213.5° C. (decomposed). $^1$H-NMR (DMSO-d6, HCl salt): δ8.27–8.10 (m, 3H), 7.80–7.72 (m, 2H), 7.68–7.56 (m, 3H), 7.43–7.13 (m, 3H), 5.93 (s, 1H), 4.58–2.86 (m, 14H), 3.46 (s, 3H), 3.40 (s, 3H), 2.09–1.62 (m, 8H) IR (KBr): 3430, 2950, 1692, 1625 cm$^{-1}$.

hu 1H-NMR (CDCl$_3$, free base): δ7.82–7.70 (m, 2H), 7.59–7.44 (m, 3H), 7.26 (d, J=8.1 Hz, 2H), 7.01 (t, J=8.1 Hz, 1H), 5.97 (s, 1H), 4.55 (d,J=12.8 Hz, 2H), 4.03–3.76 (m, 3H), 3.71–3.44 (m, 5H), 3.53 (s, 3H), 3.52 (s, 3H), 3.05–2.92 (m, 1H), 2.72–2.41 (m, 4H), 2.21–2.15 (m, 1H), 1.97–1.41 (m, 8H).

Example 12

(4S)-Dimethyl 4-(2,6-Dichlorophenyl)-2-{4-[(2R,S)-1-methyl-2-pyrrolidinyl]methyl-1-piperazinyl}carbonylmethyl-6-[(S)-phenylsulfinylmethyl]-1,4-dihydropyridine-3,5-dicarboxylate, Dihydrochloride This was prepared by a procedure similar to that described in Example 1-E, as a pale yellow solid.

mp: 186.0–188.0° C. (decomposed) $[\alpha]_D^{24}$ –174.3 (c=0.28, MeOH) $^1$H-NMR (CDCl$_3$, free base): δ8.13–8.01 (m, 1H), 7.81–7.69 (m, 2H), 7.61–7.47 (m, 3H), 7.27 (d, J=7.8 Hz, 2H), 7.02 (t, J=7.8 Hz, 1H), 5.97 (s, 1H), 4.55 (d, J=12.8 Hz, 1H), 3.99–3.42 (m, 7H), 3.53 (s, 3H), 3.52 (s, 3H), 3.22–2.31 (m, 12H), 2.23–1.53 (m, 4H).

$^1$H-NMR (DMSO-d6, HCl salt): δ9.47–9.30 (m, 1H), 7.82–7.72 (m, 2H), 7.68–7.58 (m, 3H), 7.38 (d, J=8.1 Hz, 2H), 7.19 (dd, J=7.5, 8.1 Hz, 1H), 5.93 (s, 1H), 4.41 (d, J=12.8 Hz, 1H), 3.46 (s, 3H), 3.40 (s, 3H), 2.90 (s, 3H), 4.18–2.63 (m, 16H), 2.12–1.73 (m, 4H). IR (KBr): 3430, 2950, 1692, 1628 cm$^{-1}$.

Example 13

(4S)-Dimethyl 4-(2,6-Dichlorophenyl)-2-{4-[(2S)-1-methyl-2-pyrrolidino]-1-piperazinyl}carbonylmethyl-6-[(S)-phenylsulfinylmethyl]-1,4-dihydropyridine-3,5-dicarboxylate, Dihydrochloride This was prepared by a procedure similar to that described in Example 1-E, as a pale yellow solid.

mp 177.3–179.8° C. (decomposed) $[\alpha]_D^{25}$ –177.1 (c=0.315, MeOH) $^1$H-NMR (DMSO-d6, HCl salt): δ9.52–9.32 (m, 1H), 7.82–7.72 (m, 2H), 7.69–7.54 (m, 3H), 7.38 (d, J=8.1 Hz, 2H), 7.19 (dd, J=7.8, 8.4 Hz, 1H), 5.93 (s, 1H), 4.42 (d, J=12.6 Hz, 1H), 4.34–2.65 (m, 16H), 3.47 (s, 3H), 3.41 (s, 3H), 2.91 (s, 3H), 2.11–1.65 (m, 4H). IR(KBr): 3430, 3005, 2955, 1691, 1644, 1635, 1629 cm$^{-1}$.

$^1$H-NMR (CDCl$_3$, free base): δ8.29 (br.s, 1H), 7.82–7.72 (m, 2H), 7.59–7.45 (m, 3H), 7.26 (d, J=8.1 Hz, 2H), 7.02 (dd, J=7.8, 8.4 Hz, 1H), 5.96 (s, 1H), 4.58 (d, J=12.6 Hz, 1H), 4.05 (d, J=15.3 Hz, 1H), 3.84 (d, J=12.6 Hz, 1H), 3.73 (d, J=15.3 Hz, 1H), 3.82–3.23 (m, 5H), 3.53 (s, 3H), 3.51 (s, 3H), 2.89–2.25 (m, 8H), 2.59 (s, 3H), 2.13–1.54 (m, 4H).

Example 14

(4S)-Dimethyl 4-(2,6-Dichlorophenyl)-2-{4-[(2R)-1-methyl-2-pyrrolidino]-1-piperazinyl}carbonylmethyl-6-[(S)-phenylsulfinylmethyl]-1,4-dihydropyridine-3,5-dicarboxylate, dihydrochloride This was prepared by a procedure similar to that described in Example 1-E, as a pale yellow solid.

mp 181.0–182.5° C. (decomposed) $[\alpha]_D^{23}$ –192.1 (c=0.280, MeOH) mp: 181.0–182.5° C. (decomposed). $^1$H-NMR (DMSO-d6, HCl salt): δ9.50–9.30 (m, 1H), 7.83–7.72 (m, 2H), 7.69–7.56 (m, 3H), 7.38 (d, J=8.1 Hz, 2H), 7.19 (dd, J=7.8, 8.4 Hz, 1H), 5.93 (s, 1H), 4.42 (d, J=12.6 Hz, 1H), 4.69–2.23 (m, 16H), 3.47 (s, 3H), 3.40 (s, 3H), 2.91 (s, 3H), 2.12–1.62 (m, 4H). IR (KBr): 3425, 2955, 1692, 1646, 1628 cm$^{-1}$.

$^1$H-NMR (CDCl$_3$, free base): δ8.22–8.09 (m, 1H), 7.81–7.71 (m, 2H), 7.59–7.47 (m, 3H), 7.26 (d, J=8.1 Hz, 2H), 7.02 (t, J=8.1 Hz, 1H), 5.95 (s, 1H), 4.55 (d, J=12.9 Hz, 1H), 4.04–3.43 (m, 7H), 3.52 (s, 3H), 3.52 (s, 3H), 3.12–2.33 (m, 12H), 2.19–1.62 (m, 4H).

Example 15

(4S)-Dimethyl 4-(2,6-Dichlorophenyl)-2-[(R,S)-2-(dimethylamino)methylpyrrolidino]carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp 172.0–173.2° C. (decomposed) $[\alpha]_D^{24}$ –180.9 (c=0.345, MeOH) $^1$H-NMR (DMSO-d6, HCl salt): δ9.82–9.43 (m, 2H), 7.83–7.50 (m, 5H), 7.38 (d, J=8.1 Hz, 2H), 7.19 (dd, J=7.8, 8.4 Hz, 1H), 5.94, 5.92 (s×2, 1H), 4.49–4.22 (m, 3H), 3.97–3.72 (m, 2H), 3.61–2.64 (m, 10H), 3.463, 3.457, 3.41 (s×3, 6H), 2.10–1.72 (m, 4H). IR (KBr): 3435, 1693, 1644, 1621 cm$^{-1}$.

$^1$H-NMR (CDCl$_3$, free base): δ8.75–8.50 (m, 1H), 7.86–7.70 (m, 2H), 7.59–7.41 (m, 3H), 7.32–7.21(m, 2H), 7.07–6.96 (m, 1H), 6.07–5.96 (m, 1H), 4.74–3.38 (m, 13H), 2.64–1.79 (m, 12H).

Example 16

(4S)-Dimethyl 4-(2,6-Dichlorophenyl)-2-[4-(1-piperidino)piperidino]carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp 171.6–173.0° C. (decomposed) $[\alpha]_D^{24}$ –180.6 (c=0.32, MeOH) $^1$H-NMR (DMSO-d6, HCl salt): δ10.41–10.03 (m, 1H), 9.42–9.28 (m, 1H), 7.82–7.51 (m, 5H), 7.38 (d, J=8.1 Hz, 2H), 7.19 (t, J=8.1 Hz, 1H), 5.93 (s, 1H), 4.59–4.33 (m, 2H), 4.20–2.40 (m, 11H), 3.46 (s, 3H), 3.39 (s, 3H), 2.21–1.28 (m, 10H). IR (KBr): 3435, 2955, 1691, 1627 cm$^{-1}$.

$^1$H-NMR (CDCl$_3$, free base): δ8.26, 8.12 (br.s×2, 1H), 7.81–7.70 (m, 2H), 7.60–7.45 (m, 3H), 7.27, 7.26 (d×2, J=8.1 Hz, 2H), 7.02 (t, J=8.1 Hz, 1H), 5.99, 5.98 (s×2, 1H), 4.73–4.50 (m, 2H), 4.20–3.72 (m, 5H), 3.53 (s, 6H), 3.60–3.41 (m, 1H), 2.67–2.40 (m, 5H), 2.15–1.38 (m, 10H).

Example 17

(4S)-Dimethyl 4-(2,6-Dichlorophenyl)-2-{4-[(2R,S)-1-methyl-2-piperidinyl]methyl-1-piperazinyl}carbonylmethyl-6-[(S)-phenylsulfinylmethyl]-1,4-dihydropyridine-3,5-dicarboxylate, dihydrochloride This was prepared by a procedure similar to that described in Example 1-E, as a pale yellow solid.

mp 187.0–189.0° C. (decomposed) $[\alpha]_D^{23}$ –176.0 (c=0.25, MeOH) $^1$H-NMR(DMSO-d6, HCl salt): δ9.45–9.28 (m, 1H), 7.81–7.53 (m, 5H), 7.38 (d, J=8.1 Hz, 2H), 7.19 (t, J=8.1 Hz, 1H), 5.93 (s, 1H), 4.42 (d,J=12.5 Hz, 1H), 4.39–2.20 (m, 15H), 1.95–1.30 (m, 6H). IR (KBr): 3420, 2960, 1692, 1627 cm$^{-1}$.

$^1$H-NMR (CDCl$_3$, free base): δ8.17 (br.s, 1H), 7.81–7.70 (m, 2H), 7.59–7.47 (m, 3H), 7.27 (d,J=8.1 Hz, 2H), 7.02 (t, J=8.1 Hz, 1H), 5.97 (s, 1H), 4.54 (d,J=12.8 Hz, 1H), 4.02–3.78 (m, 3H), 3.70–3.45 (m, 4H), 3.53 (s, 6H), 2.94–2.01 (m, 10H), 2.36 (s, 3H), 1.89–1.17 (m, 5H).

Example 18

(4S)-Dimethyl 4-(2,6-Dichlorophenyl)-2-(4-cyclopentyl-1-piperazinyl]carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp 198.0–200.2° C. (decomposed) $[\alpha]_D^{24}$ –184.6 (c=0.26, MeOH) $^1$H-NMR (DMSO-d6, HCl salt): δ9.49–9.28 (m, 1H), 7.82–7.72 (m, 2H), 7.68–7.52 (m, 3H), 7.38 (d, J=8.1 Hz, 2H), 7.19 (t, J=8.1 Hz, 1H), 5.93 (s, 1H), 4.52–2.70 (m, 13H), 3.47 (s, 3H), 3.40 (s, 3H), 2.08–1.41 (m, 8H). IR Kr): 3430, 2955, 1692, 1649, 1633, 1629 cm$^{-1}$.

$^1$H-NMR (CDCl$_3$, free base): δ8.27 (br.s, 1H), 7.82–7.71 (m, 2H), 7.59–7.47 (m, 3H), 7.26 (d, J=8.1 Hz, 2H), 7.02 (t, J=8.1 Hz, 1H), 5.97 (s, 1H), 4.56 (d, J=12.9 Hz, 1H), 4.00 (d, J=15.5 Hz, 1H), 3.85 (d, J=12.9 Hz, 1H), 3.80 (d, J=15.5 Hz, 1H), 3.71–3.53 (m, 4H), 3.53 (s, 3H), 3.52 (s, 3H), 2.68–2.18 (m, 5H), 1.92–1.29 (m, 8H).

Example 19

(4S)-Dimethyl 4-(2,6-Dichlorophenyl)-2-{4-[2-(1-pyrrolidion)-acetyl]-1-piperazinyl}carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp 183.6–186.2° C. (decomposed) $[\alpha]_D^{25}$ –171.6 (c=0.275, MeOH) $^1$H-NMR (DMSO-d6, HCl salt): δ10.12–9.84 (m, 1H), 9.47–9.36 (m, 1H), 7.82–7.52 (m, 5H), 7.38 (d, J=8.1 Hz, 2H), 7.19 (t, J=8.1 Hz, 1H), 5.93 (s, 1H), 4.50–4.30 (m, 3H), 4.19–3.97 (m, 1H), 3.46 (s, 3H), 3.39 (s, 3H), 3.81–3.07 (m, 14H), 2.07–1.83 (m, 4H). IR(KBr): 3440, 3095, 3000, 2950, 1692, 1651(br) cm$^{-1}$.

$^1$H-NMR (CDCl$_3$, free base): δ8.32–8.09 (m, 1H), 7.85–7.69 (m, 2H), 7.60–7.43 (m, 3H), 7.26 (d, J=8.1 Hz, 2H), 7.02 (t, J=8.1 Hz, 1H), 5.98 (s, 1H), 4.61 (d, J=12.8 Hz, 1H), 4.10–3.30 (m, 13H), 3.52 (s, 6H), 3.40 (s, 2H), 2.76–2.53 (m, 4H), 1.90–1.71 (m, 4H).

Example 20

(4S)-Dimethyl 4-(2,6-Dichlorophenyl)-2-(4-cyclohexylmethylamino piperidino)carbonylmethyl-6-[(S)-phenylsulfinylmethyl]-1,4-dihydropyridine-3,5-dicarboxylate monohydrochloride A. (4S)-Dimethyl 4-(2,6-Dichlorophenyl)-2-[4-[N-(t-butoxycarbonyl)-N-cyclohexylmethylamino]piperidino]carbonylmethyl-6-[(S)-phenylsulfinylmethyl]-1,4-dihydropyridine-3,5-dicarboxylate This was prepared by a procedure similar to that described in Example 1-E, as a pale yellow solid.

$^1$H-NMR (CDCl$_3$): δ8.23–8.16 (m, 0.5H), 8.03–7.98 (m, 0.5H), 7.81–7.71 (m, 2H), 7.60–7.47 (m, 3H), 7.27 (d, J=8.1 Hz, 2H), 7.02 (t, J=8.1 Hz, 1H), 5.99, 5.98 (s×2, 1H), 4.80–4.65 (m, 1H), 4.57 (d, J=12.8 Hz, 1H), 4.19–2.43 (m, 9H), 3.53 (s, 3H), 3.52 (s, 3H), 1.95–0.74 (m, 15H), 1.45, 1.44 (s×2, 9H).

B. (4S)-Dimethyl 4-(2,6-Dichlorophenyl)-2-(4-cyclohexylmethylamino piperidino)carbonylmethyl-6-[(S)-phenylsulfinylmethyl]-1,4-dihydropyridine-3,5-dicarboxylate, monohydrochloride This was prepared by a procedure similar to that described in Preparation 2-B, as a pale yellow solid.

mp: 204.0–207.2° C. (decomposed) $[\alpha]_D$23–184.7 (c=0.30, MeOH) $^1$H-NMR (DMSO-d6, HCl salt): δ9.45–9.27 (m, 1H), 8.87–8.59 (m, 2H), 7.80–7.54 (m, 5H), 7.38 (d, J=8.1 Hz, 2H), 7.19 (t, J=8.1 Hz, 1H), 5.93 (s, 1H), 4.52–4.32 (m, 2H), 4.19–3.73 (m, 3H), 3.46 (s, 3H), 3.41, 3.39 (s×2, 3H), 3.58–2.41 (m, 6H), 2.18–0.83 (m, 15H). IR(KBr): 3430, 2935, 1691, 1625 cm$^{-1}$.

Example 21

(4S)-Dimethyl 4-(2,6-Dichlorophenyl)-2-[(3S)-3-(N-methyl-8-azabicyclo[3.2.1]oct-7-yl)amino-1-pyrrolidino]carbonylmethyl-6-[(S)-phenylsulfinylmethyl]-1,4-dihydropyridine-3,5-dicarboxylate, dihydrochloride A. (4S)-Dimethyl 4-(2,6-Dichlorophenyl)-2-[(3S)-3-[N-(t-butoxycarbonyl)-N-(N-methyl-8-azabicyclo[3.2.1]oct-7-yl)]amino-1-pyrrolidino]carbonylmethyl-6-[(S)-phenylsulfinylmethyl]-1,4-dihydropyridine-3,5-dicarboxylate This was prepared by a procedure similar to that described in Example 1-E, as a pale yellow solid.

$^1$H-NMR (CDCl$_3$): δ7.85–7.70 (m, 2H), 7.57–7.40 (m, 3H), 7.27 (d, J=8.1 Hz, 2H), 7.00, 6.99 (t×2, J=8.1 Hz, 1H), 6.05 (s, 1H), 4.81–3.15 (m, 18H), 2.92–1.70 (m, 13H), 1.48, 1.47 (s×2, 9H).

B. (4S)-Dimethyl 4-(2,6-Dichlorophenyl)-2-[(3S)-3-(N-methyl-8-azabicyclo[3.2.1]oct-7-yl)amino-1-pyrrolidino]carbonylmethyl-6-[(S)-phenylsulfinylmethyl]-1,4-dihydropyridine-3,5-dicarboxylate, Dihydrochloride This was prepared by a procedure similar to that described in Preparation 2-B, as a pale yellow solid.

mp: 200.0–201.8° C. (decomposed) $[\alpha]_D^{22}$ –157.9 (c=0.285, MeOH) $^1$H-NMR (DMSO-d6, HCl salt): δ9.58–9.30 (m, 2H), 7.81–7.70 (m, 2H), 7.68–7.52 (m, 3H), 7.37 (d, J=8.1 Hz, 2H), 7.18 (t, J=8.1 Hz, 1H), 5.93 (s, 1H), 4.48–4.30 (m, 1H), 4.14–3.08 (m, 14H), 3.46 (s, 3H), 3.40 (s, 3H), 2.80–1.80 (m, 10H). IR (KBr): 3435, 2950, 1692, 1628 cm$^{-1}$.

Example 22

(4S)-Dimethyl 4-(2,6-Dichlorophenyl)-2-[4-(8-methyl-8-azabicyclo[3.2.1]oct-3-yl-2,3,4,5,6,7-hexahydro-1H-1,4-diazepin-1-yl]carbonylmethyl-6-[(S)-phenylsulfinylmethyl]-1,4-dihydropyridine-3,5-dicarboxylate, monohydrochloride This was prepared by a procedure similar to that described in Preparation 1-E, as a pale yellow solid.

mp: 107–108° C. (decomposed) 2HCl salt $[\alpha]_D^{25}$ –150 (c=1.15, MeOH) IR(KBr) 3410, 1691, 1660, 1645, 1631, 1103. $^1$H NMR (DMSO) δ11.50–10.50 (m), 9.68–9.20 (m), 7.83–7.69 (m, 2H), 7.69–7.50 (m, 3H), 7.46–7.27 (m, 2H), 7.27–7.21 (m, 1H), 5.94 (s, 1H), 4.50–1.70 (m), 3.47 (s, 3H), 3.40 (s, 3H).

free base $^1$HNMR (CDCl$_3$) δ8.37 (br.s, 1H), 7.88–7.62 (m, 2H), 7.60–7.36 (m, 3H), 7.26 (d,J=7.7 Hz, 2H), 7.01 (dd, J=8.4, 7.7 Hz, 1H), 5.98 (s, 1H), 4.53 (d, J=12.8 Hz, 1H), 4.09 (d, J=10.3 Hz, 0.5H), 4.03 (d, J=10.3 Hz, 0.5H), 3.83 (d, J=12.8 Hz, 1H), 3.80–3.35 (m), 3.53 (s, 3H), 3.52 (s, 1.5H), 3,51(s, 1.5H), 3.29–3.01 (m, 2H), 2.90–2.50 (m, 5H), 2.26 (s, 1.5H), 2.25 (s, 1.5H), 2.10–1.30 (m).

Example 23

(4S)-Dimethyl 4-(2,6-Dichlorophenyl)-2-[4-(2-amino-2-methyl)propionyl-1-piperazinyl)carbonylmethyl-6-[(S)-phenylsulfinylmethyl]-1,4-dihydropyridine-3,5-dicarboxylate, monohydrochloride A. (4S)-Dimethyl 4-(2,6-Dichlorophenyl)-2-[4-[2-(t-butoxycarbonyl)amino-2-methyl]propionyl-1-piperazinyl]carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

$^1$H-NMR (CDCl$_3$): δ8.11–7.99 (m, 1H), 7.79–7.68 (m, 2H), 7.60–7.46 (m, 3H), 7.26 (d, J=8.1 Hz, 2H), 7.02 (dd, J=7.8, 8.4 Hz, 1H), 5.92 (s, 1H), 4.88–4.72 (m, 1H), 4.57 (d, J=12.8 Hz, 1H), 4.04–3.42 (m, 11H), 3.53 (s, 3H), 3.52 (s, 3H), 1.48 (s, 6H), 1.42 (s, 9H).

B. (4S)-Dimethyl 4-(2,6-Dichlorophenyl)-2-[4-(2-amino-2-methyl)propionyl-1-piperazinyl)carbonylmethyl-6-[(S)-phenylsulfinylmethyl]-1,4-dihydropyridine-3,5-dicarboxylate monohydrochloride This was prepared by a procedure similar to that described in Preparation 2-B, as a pale yellow solid.

mp: 200.1–201.1° C. (decomposed) $[\alpha]_D^{24}$ –197.7 (c=0.265, MeOH) $^1$H-NMR (DMSO-d6, HCl salt): δ9.38 (br.s, 1H), 8.37–7.90 (m, 2H), 7.80–7.70 (m, 2H), 7.67–7.53 (m, 3H), 7.38 (d, J=8.1 Hz, 2H), 7.18 (t, J=8.1 Hz, 1H), 5.93 (s, 1H), 4.42 (d, J=12.1 Hz, 1H), 4.04 (d, J=15.8 Hz, 1H), 3.72 (d, J=12.1 Hz, 1H), 3.71–3.34 (m, 9H), 3.46 (s, 3H), 3.39 (s, 3H), 1.56 (s, 6H). IR (KBr): 3435, 2950, 1692, 1630 cm$^{-1}$.

Example 24

(4S)-Dimethyl 4-(2,6-Dichlorophenyl)-2-[4-(2-acetylamino-2-methyl)propionyl-1-piperazinyl)carbonylmethyl-6-[(S)-phenylsulfinylmethyl]-1,4-dihydropyridine-3,5-dicarboxylate This was prepared by a procedure similar to that described in Example 1-E, as a pale yellow solid. mp: 157.6–159.5° C. (decomposed) $[\alpha]_D^{23}$ –193.2 (c=0.235, MeOH) $^1$H-NMR (CDCl$_3$): δ7.96 (br.s, 1H), 7.79–7.69 (m, 2H), 7.61–7.48 (m, 3H), 7.28 (d,J=8.1 Hz, 2H), 7.03 (dd, J=7.8, 8.4 Hz, 1H), 6.29 (br.s, 1H), 5.97 (s, 1H), 4.57 (d, J=12.9 Hz, 1H), 3.92 (s, 2H), 3.86 (d, J=12.9 Hz, 1H), 3.82–3.48 (m, 8H), 3.54 (s, 3H), 3.52 (s, 3H), 1.98 (s, 3H), 1.60 (s, 6H). IR (KBr): 3440, 3000, 2950, 1694, 1630 (br) cm$^{-1}$.

Example 25

(–)-4S)-4-(2,6-Dichlorophenyl)-6-(S)-phenylsulfinylmethyl-3,5-dimethoxycarbonyl-1,4-dihydropyridin-2-ylacetyl-1-piperazin-4-ylacetic acid This was prepared by hydrolysis of the product in example 8 in usual manner as a yellow soid.

mp 226–228° C. (decomposed). IR( KBr) 3400, 3325, 1690, 1632, 1580, 1150 cm$^{-1}$. $^1$HNMR (DMSO) δ9.30 (br.s, 1H), 7.89–7.50 (m, 5H), 7.37 (d, J=7.7 Hz, 2H), 7.18 (t, J=7.7 Hz, 1H), 5.92 (s, 1H), 4.41 (d, J=12.1 Hz, 1H), 4.00 (d, J=15.8 Hz, 1H), 3.39 (s, 3H), 3.89–2.20 (m, 15H).

Example 26

(4S)-Dimethyl 4-(2,6-Dichlorophenyl)-2- [4-(2-amino-2-methyl)propyl-1-piperazinyl]carbonylmethyl-6-[(S-phenylsulfinylmethyl]-1,4-dihydropyridine-3,5-dicarboxylate, dihydrochloride This was prepared by a procedure similar to that described in Preparation 2-B, as a pale yellow solid.

mp: 203.5–205.1° C. (decomposed). $[\alpha]_D^{25}$ –197.1 (c=0.280, MeOH) $^1$H-NMR (DMSO-d6, HCl salt): δ9.45–9.26 (m, 1H), 7.80–7.70 (m, 2H), 7.68–7.53 (m, 3H), 7.38 (d, J=8.1 Hz, 2H), 7.19 (dd, J=7.8, 8.4 Hz, 1H), 5.93 (s, 1H), 4.42 (d, J=12.6 Hz, 1H), 4.21–3.22 (m, 13H), 3.46 (s, 3H), 3.40 (s, 3H), 1.57–1.10 (m, 6H). IR (KBr): 3425, 2955, 1692, 1626 (br) cm$^{-1}$.

Example 27

(4S)-Dimethyl 4-(2,6-Dichlorophenyl)-2-[4-(2-acetylamino-2-methyl)propyl-1-piperazinyl]carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp: 162.4–164.8° C. (decomposed). $[\alpha]_D^{25}$ –176.1 (c=0.310, MeOH) $^1$H-NMR (DMSO-d6, HCl salt): δ10.53–10.26 (m, 1H), 9.48–9.27 (m, 1H), 8.06–7.90 (m, 1H), 7.82–7.71 (m, 2H), 7.68–7.54 (m, 3H), 7.38 (d, J=8.1 Hz, 2H), 7.19 (t, J=8.1 Hz), 5.93 (s, 1H), 4.43 (d, J=12.3 Hz, 1H), 4.28–2.87 (m, 11H), 3.47 (s, 3H), 3.41 (s, 3H), 3.17 (s, 2H), 1.87 (s, 3H), 1.37 (s, 6H). IR (KBr): 3445, 3305, 3005, 3000, 2955, 1691, 1645, 1639 cm$^{-1}$.

$^1$H-NMR (CDCl$_3$, free base): δ8.07 (br.s, 1H), 7.80–7.71 (m, 2H), 7.59–7.48 (m, 3H), 7.27 (d, J=8.1 Hz, 2H), 7.02 (dd, J=7.7, 8.4 Hz, 1H), 5.97 (s, 1H), 5.63 (br.s, 1H), 4.52 (d, J=12.8 Hz, 1H), 3.95 (d, J=15.4 Hz, 1H), 3.88 (d, J=12.8 Hz, 1H), 3.84 (d, J=15.4 Hz, 1H), 3.72–3.48 (m, 4H), 3.53 (s, 3H), 3.52 (s, 3H), 2.63–2.48 (m, 6H), 1.92 (s, 3H), 1.31 (s, 6H).

Example 28

(4S)-Dimethyl 4-(2,6-Dichlorophenyl)-2-(4-methyl-1-piperazinyl)carbonylmethyl-6-[(S)-phenylsulfinylmethyl]-1,4-dihydropyridine-3,5-dicarboxylate, monohydrochloride This was prepared by a procedure similar to that described in Example 1-E, as a pale yellow solid.

mp 194.5–196.4° C. (decomposed). $[\alpha]_D^{24}$-203.5 (c=0.290, MeOH) $^1$H-NMR (DMSO-d6, HCl salt): δ11.19–10.70 (m, 1H), 9.39 (br.s, 1H), 7.82–7.51 (m, 5H), 7.38 (d, J=8.1 Hz, 2H), 7.19 (t, J=8.1 Hz, 1H), 5.93 (s, 1H), 4.43 (d, J=12.6 Hz, 11H), 4.50–2.60 (m, 11H), 3.47 (s, 3H), 3.40 (s, 3H), 2.76 (s, 3H). IR (KBr): 3435, 3005, 2955, 1692, 1647 (br) cm$^{-1}$.

$^1$H-NMR (CDCl$_3$, free base): δ8.19 (br.s, 1H), 7.81–7.70 (m, 2H), 7.60–7.46 (m, 3H), 7.27 (d, J=7.7 Hz, 2H), 7.02 (dd, J=7.3, 8.1 Hz, 1H), 5.97 (s, 1H), 4.55 (d, J=12.8 Hz, 1H), 4.00 (d, J=15.6 Hz, 1H), 3.86 (d, J=12.8 Hz, 1H), 3.82 (d, J=15.6 Hz, 1H), 3.76–3.45 (m, 4H), 3.53 (s, 6H), 2.50–2.30 (m, 4H), 2.29 (s, 3H).

Example 29

(4S)-Dimethyl 4-(2,6-Dichlorophenyl)-2-[4-(3-oxo-bicyclo[3.3.0]oct-7-yl)-1-piperazinyl] carbonylmethyl-6-[(S)-phenylsulfinylmethyl]-1,4-dihydropyridine-3,5-dicarboxylate, monocitrate This was prepared by a procedure similar to that described in Example 1-E, as a pale yellow solid.

mp 131.9–135.7° C.

$[\alpha]_D^{23}$-129.4 (c=0.255, MeOH) $^1$H-NMR (DMSO-d6, citric acid salt): δ9.27 (br.s, 1H), 7.81–7.71 (m, 2H), 7.68–7.53 (m, 3H), 7.38 (d, J=8.1 Hz, 2H), 7.18 (dd, J=7.8, 8.4 Hz, 1H), 5.92 (s, 1H), 4.42 (d, J=12.6 Hz, 1H), 3.99 (d, J=16.2 Hz, 1H), 3.69 (d, J=12.6 Hz, 1H), 3.68 1.94 (m, 22H), 3.47 (s, 3H), 3.39 (s, 3H), 1.47–1.25 (m, 2H). IR (KBr): 3435, 2955, 1732, 1693, 1627 cm$^{-1}$.

$^1$H-NMR (CDCl$_3$, free base): δ8.14 (br.s, 1H), 7.80–7.70 (m, 2H), 7.60–7.46 (m, 3H), 7.27 (d, J=8.1 Hz, 2H), 7.02 (dd, J=7.8, 8.4 Hz, 1H), 5.98 (s, 1H), 4.53 (d, J=12.6 Hz, 1H), 4.01–3.80 (m, 3H), 3.75–3.43 (m, 4H), 3.54 (s, 3H), 3.53 (s, 3H), 2.80–2.39 (m, 9H), 2.32–2.03 (m, 4H), 1.45–1.23 (m, 2H).

Monohydrochloride salt;

mp 179.8–182.5° C. (decomposed). $[\alpha]_D^{24}$-160.7 (c=0.285, MeOH) $^1$H-NMR (DMSO-d6, HCl salt): δ11.63–11.30 (m, 1H), 9.48–9.30 (m, 1H), 7.82–7.71 (m, 2H), 7.69–7.54 (m, 3H), 7.38 (d, J=8.1 Hz, 2H), 7.19 (t, J=8.1 Hz, 1H), 5.93 (s, 1H), 4.53–2.12 (m, 21H), 3.47 (s, 3H), 3.41 (s, 3H), 1.90–1.68 (m, 2H). IR (KBr): 3445, 2955, 1734, 1692, 1648, 1644 cm$^{-1}$.

Example 30

(4S)-Dimethyl 4-(2,6-Dichlorophenyl)-2-[4-[1-(methoxycarbonylmethyl)cyclopent-1-ylacetyl] piperazin-1-yl]carbonylmethyl-6-[(S)-phenylsulfinylmethyl]-1,4-dihydropyridine-3,5-dicarboxylate This was prepared by a procedure similar to that described in Example 1-E, as a pale yellow solid.

mp 100–104° C. $^1$H-NMR (CDCl$_3$): δ8.00 (br.s, 1H), 7.78–7.71 (m, 2H), 7.58–7.49 (m, 3H), 7.27 (d, J=8.1 Hz, 2H), 7.03 (t, J=5.3 Hz, 1H), 5.97 (s, 1H), 4.65–4.54 (m, 1H), 4.01–3.82 (m, 3H), 3.72–3.47 (m, 17H), 2.63 (s, 2H), 2.60 (s, 2H), 1.75–1.57 (m, 8H). IR (KBr): 2980, 1728, 1692, 1631, 1508, 1430, 1290, 1219, 1193, 1157, 1102, 1085, 1046, 1021.

Example 31

(4S)-Dimethyl 4-(2,6-Dichlorophenyl)-2-[4-[2-amino-2-methylpropionylamino]-1-piperidinyl] carbonylmethyl-6-[(S)-phenylsulfinylmethyl]-1,4-dihydropyridine-3,5-dicarboxylate, monocitrate A. (4S)-Dimethyl 4-(2,6-Dichlorophenyl)-2-[4-[2-(Boc-amino)-2-methylpropionylamino]-1-piperidinyl] carbonylmethyl-6-[(S)-phenylsulfinylmethyl]-1,4-dihydropyridine-3,5-dicarboxylate This was prepared by a procedure similar to that described in Example 1-E, as a pale yellow solid.

mp 194.5–196.4° C. (decomposed). $^1$H-NMR (CDCl$_3$): δ8.07–7.97 (m, 0.5H), 7.97–7.88 (m, 0.5H), 7.81–7.70 (m, 2H), 7.61–7.47 (m, 3H), 7.27 (d, J=8.1 Hz, 2H), 7.03 (t, J=8.1 Hz, 1H), 6.84–6.51 (m, 1H), 6.00, 5.97 (s×2, 1H), 5.02–4.80 (m, 1H), 4.70–4.32 (m, 2H), 4.17–3.63 (m, 5H), 3.534, 3.528, 3.51 (s×3, 6H), 3.32–3.12 (m, 1H), 2.97–2.77 (m, 1H), 1.45 (s, 6H), 1.42 (s, 9H), 2.04–1.27 (m, 4H).

B. (4S)-Dimethyl 4-(2,6-Dichlorophenyl)-2-[4-[2-amino-2-methylpropionylamino]-1-piperidinyl]carbonylmethyl-6-[(S)-phenylsulfinylmethyl]-1,4-dihydropyridine-3,5-dicarboxylate, monocitrate This was prepared by a procedure similar to that described in Example 1-E, as a yellow solid.

mp: 187.7–191.0° C. (decomposed). $[\alpha]_D^{24}$-194.6 (c=0.330, MeOH) $^1$H-NMR (DMSO-d6, citric acid salt): δ9.40–9.27 (m, 1H), 8.23–7.53 (m, 8H), 7.37 (d, J=8.1 Hz, 2H), 7.18 (dd, J=7.8, 8.4 Hz, 1H), 5.93 (s, 1H), 4.48–2.65 (m, 15H), 1.88–1.21 (m, 4H), 1.43 (s, 6H). IR (KBr): 3435, 2955, 1693, 1653, 1624 cm$^{-1}$.

Example 32

(4S)-Dimethyl 4-(2,6-Dichlorophenyl)-2-[4-(2,2-dimethyl)propionyl-1-piperazinylcarbonylmethyl-6-[(S)-phenylsulfinylmethyl]-1,4-dihydropyridine-3,5-dicarboxylate This was prepared by a procedure similar to that described in Example 1-E, as a yellow solid.

mp: 134.1–135.7° C. $[\alpha]_D^{24}$-212.6 (c=0.270, MeOH) $^1$H-NMR (CDCl$_3$): δ8.03 (br.s, 1H), 7.79–7.70 (m, 2H), 7.60–7.49 (m, 3H), 7.27 (d, J=8.1 Hz, 2H), 7.03 (dd, J=7.8, 8.4 Hz, 1H), 5.98 (s, 1H), 4.59 (d, J=12.9 Hz, 1H), 3.99 (d, J=15.3 Hz, 1H), 3.88 (d, J=15.3 Hz, 1H), 3.86 (d, J=12.9 Hz, 1H), 3.77–3.52 (m, 8H), 3.54 (s, 3H), 3.52 (s, 3H), 1.28 (s, 9H). IR (KBr): 3440, 3305, 2985, 2955, 1694, 1628 cm$^{-1}$.

Example 33

(4S)-Dimethyl 4-(2,6-Dichlorophenyl)-2-{4-[2-(N-carbamoyl)amino-2-methyl]propionyl-1-piperazinyl}carbonylmethyl-6-[(S)-phenylsulfinylmethyl]-1,4-dihydropyridine-3,5-dicarboxylate This was prepared by a procedure similar to that described in Example 1-E, as yellow solid.

mp: 173.5–175.8° C. (decomposed). $[\alpha]_D^{23}$-190.2 (c=0.225, MeOH). $^1$H-NMR (DMSO-d6): δ9.27 (br.s, 1H), 7.80–7.70 (m, 2H), 7.68–7.56 (m, 3H), 7.37 (d, J=8.1 Hz, 2H), 7.18 (t, J=8.1 Hz, 1H), 6.45 (br.s, 1H), 5.93 (s, 1H), 5.43 br.s, 2H), 4.42 (d, J=12.3 Hz, 1H), 4.02 (d, J=15.9 Hz, 1H), 3.68 (d, J=12.3 Hz, 1H), 3.75–3.26 (m, 9H), 3.47 (s, 3H), 3.38 (s, 3H), 1.31 (s, 6H). IR (KBr): 3450, 2950, 1692, 1628 (br) cm$^{-1}$.

Example 34

(4S)-Dimethyl 4-(2,6-Dichlorophenyl)-2-[4-(2,2-dimethyl-3-hydroxy)propionyl-1-piperazinyl) carbonylmethyl-6-[(S)-phenylsulfinylmethyl]-1,4-dihydropyridine-3,5-dicarboxylate This was prepared by a procedure similar to that described in Example 1-E, as a yellow solid.

mp: 135.6–137.0° C.

[α]$_D^{24}$–196.0 (c=0.250, MeOH) $^1$H-NMR (CDCl$_3$): δ7.98 (br.s, 1H), 7.79–7.69 (m, 2H), 7.60–7.48 (m, 3H), 7.27 (d, J=8.1 Hz, 2H), 7.03 (dd, J=7.8, 8.4 Hz, 1H), 5.97 (s, 1H), 4.59 (d, J=12.6 Hz, 1H), 3.98–3.90 (m, 2H), 3.86 (d, J=12.6 Hz, 1H), 3.77–3.43 (m, 10H), 3.54 (s, 3H), 3.51 (s, 3H), 1.28, 1.27 (s×2, 6H). IR (KBr): 3450, 2950, 1693, 1625 cm$^{-1}$.

Example 35

(4S)-Dimethyl 4-(2,6-Dichlorophenyl)-2-[4-(2,2-dimethyl-3-hydroxy)propyl-1-piperazinyl] carbonylmethyl-6-[(S)-phenylsulfinylmethyl]-1,4-dihydropyridine-3,5-dicarboxylate, monohydrochloride This was prepared by a procedure similar to that described in Example 1-E, as a yellow solid.

mp: 150.7–153.4° C. (decomposed). [α]$_D^{26}$–185.4 (c=0.260, MeOH) $^1$H-NMR (DMSO-d6, HCl salt): δ9.47–9.33 (m, 1H), 7.81–7.71 (m, 2H), 7.68–7.53 (m, 3H), 7.38 (d, J=8.1 Hz, 2H), 7.19 (dd, J=7.8, 8.4 Hz, 1H), 5.93 (s, 1H), 4.41 (d, J=12.6 Hz, 1H), 4.24–2.85 (m, 15H), 3.46 (s, 3H), 3.40 (s, 3H), 1.00 (br.s, 6H). IR (KBr): 3420, 2950, 1693, 1647 (br) cm$^{-1}$.

$^1$H-NMR (CDCl$_3$, free base): δ8.11 (br.s, 1H), 7.79–7.70 (m, 2H), 7.59–7.48 (m, 3H, 7.27 (d, J=8.1 Hz, 2H), 7.02 (dd, J=7.8, 8.4 Hz, 1H), 5.97 (s, 1H), 4.52 (d, J=12.9 Hz, 1H), 4.01–3.42 (m, 7H), 3.53 (s, 3H), 3.52 (s, 3H), 3.49 (s, 2H), 2.69–2.50 (m, 4H), 2.39 (s, 2H), 0.93 (s, 6H).

Example 36

(4S)-Dimethyl 4-(2,6-Dichlorophenyl)-2-[4-(3-hydroxy-3-methyl)butyl-1-piperazinyl] carbonylmethyl-6-[(S)-phenylsulfinylmethyl]-1,4-dihydropyridine-3,5-dicarboxylate This was prepared by a procedure similar to that described in Example 1-E, as a yellow solid.

mp: 118.5–120.2° C. [α]$_D^{24}$–197.6 (c≦0.330, MeOH) $^1$H-NMR (CDCl$_3$): δ8.06 (br.s, 1H), 7.79–7.71 (m, 2H), 7.62–7.46 (m, 3H), 7.27 (d, J=8.0 Hz, 2H), 7.02 (dd, J=7.6, 8.4 Hz, 1H), 5.97 (s, 1H), 4.52 (d, J=12.6 Hz, 1H), 3.97–3.82 (m, 3H), 3.75–3.45 (m, 4H), 3.53 (s, 3H), 3.52 (s, 3H), 2.70–2.44 (m, 6H), 1.70–1.59 (m, 2H), 1.23 (s, 6H). IR (KBr): 3440, 2970, 1693, 1627 cm$^{-1}$.

Example 37

(–)-(4S)-Dimethyl 4-(2,6-Dichlorophenyl)-2-(4-carbamoylmethyl piperazinylcarbonylmethyl)-6-(S)-phenylsulfinylmethyl-1,4-dihydropyridine-3,5-dicarboxylate monohydrochloride This was prepared by a procedure similar to that described in Example 1-E, as a yellow solid.

mp 181.0–182.5° C. (decomposed). [α]$_D^{26}$–193 (c=0.82, MeOH) IR(KBr) 3330, 3285, 3190, 1692, 1660, 1636, 1195 cm$^{-1}$ $^1$H-NMR (DMSO-d6) δ10.61–10.20 (m), 9.62–9.30 (m), 8.17–7.85 (m, 1H), 7.83–7.50 (m, 6H), 5.93 (s, 1H), 4.41 (d, J=12.1 Hz, 1H), 3.46 (s, 3H), 3.41 (s, 3H), 4.50–2.70 (m, 15H).

free base $^1$H-NMR (CDCl$_3$) δ8.20 (br.s, 1H), 7.82–7.70 (m,2H), 7.62–7.44 (m, 3H), 7.28 (d, J=8.1 Hz, 2H), 7.03 (dd J=8.4, 7.3 Hz, 1H), 6.98–6.84 (m, 1H), 5.99 (s, 1H), 5.94–5.78 (m, 1H), 4.60 (d, J=12.8 Hz, 1H), 3.99 (d, J=15.4 Hz, 1H), 3.90–3.46 (m, 6H), 3.53 (s, 6H), 3.07 (d, J=16.5 Hz, 1H), 3.00 (d, J=16.2 Hz, 1H), 2.70–2.42 (m, 4H).

Example 38

(–)-(4S)-Dimethyl 4-(2,6-Dichlorophenyl)-2-(4-(3-(4-methyl piperazinyl)propyl) piperazinylcarbonylmethyl)-6-(S)-phenylsulfinylmethyl-1,4-dihydropyridine-3,5-dicarboxylate trihydrochloride This was prepared by a procedure similar to that described in Example 1-E, as a yellow solid.

mp 193.0–195.0° C. (decomposed). [α]$_D^{25}$–160 (c=0.90, MeOH) IR(KBr) 3330, 3285, 3190, 1692, 1660, 1636, 1195 cm$^{-1}$ $^1$H-NMR (DMSO-d6) δ11.62–11.22 (m), 9.48 (br.s, 1H), 7.85–7.70 (m, 2H), 7.70–7.50 (m, 3H), 7.38 (d, J=7.7 Hz, 2H), 7.19 (dd, J=8.8, 7.3 Hz, 1H), 5.93 (s, 1H), 4.42 (d, J=12.1 Hz, 1H), 3.46 (s, 3H), 3.41 (s, 3H), 2.77 (br.s, 3H), 4.30–1.75 (m, 25H).

free base $^1$H-NMR (CDCl$_3$) δ8.19 (br.s, 1H), 7.82–7.70 (m, 2H), 7.60–7.45 (m, 3H), 7.27 (d, J=7.7 Hz, 2H), 7.02 (dd, J=8.4, 7.7 Hz, 1H), 5.97 (s, 1H), 4.54 (d, J=12.8 Hz, 1H), 3.98 (d, J=15.4 Hz, 1H), 3.87 (d, J=11.4 Hz, 1H), 3.82 (d,J=15.4 Hz, 1H), 3.53 (s, 6H), 3.73–3.47 (m, 4H), 2.70–2.05 (m, 16H), 2.28 (s, 3H), 1.79–1.58 (m, 2H).

Example 39

(–)-(4S)-Dimethyl 4-(2,6-Dichlorophenyl)-2-[4-[3-(4-methylpiperazinyl-3-oxopropyl) piperazinylcarbonylmethyl]-6-(S)-phenylsulfinylmethyl-1,4-dihydropyridine-3,5-dicarboxylate dihydrochloride This was prepared by a procedure similar to that described in Example 1-E, as a yellow solid.

mp 198–200° C. (decomposed). [α]$_D^{24}$–166.6 (c=0.885, MeOH) IR(KBr) 3425, 3225, 3075, 1691, 1646, 1541, 1194, 1155 cm$^{-1}$ $^1$H-NMR (DMSO-d6) δ11.67–11.12 (m), 9.70–9.30 (m), 7.83–7.70 (m, 2H), 7.70–7.50 (m, 3H), 7.38 (d, J=7.7 Hz, 2H), 7.19 (dd, J=8.8, 7.3 Hz, 1H), 5.94 (s, 1H), 4.67–2.61 (m, 24H), 3.46 (s, 3H), 3.40 (s, 3H), 2.74 (s, 3H).

free base $^1$H-NMR (CDCl$_3$) δ8.12 (br.s, 1H), 7.82–7.69 (m, 2H), 7.61–7.46 (m, 3H), 7.27 (d, J=8.1 Hz, 2H), 7.02 (J=8.4 Hz, 1H), 5.97 (s, 1H), 4.53 (d, J=12.8 Hz, 1H), 3.94 (d, J=15.6 Hz, 1H), 3.87 (d, J=11.0 Hz, 1H), 3.86 (d, J=17.2 Hz, 1H), 3.75–3.38 (m, 8H), 3.53 (s, 6H), 2.85–2.65 (m, 2H), 2.60–2.22 (m, 10H), 2.30 (s, 3H).

Example 40

(–)-(4S)-Dimethyl 4-(2,6-Dichlorophenyl)-2-[4-(ethoxy-3-oxopropionyl) piperazinylcarbonylmethyl]-6-(S)-phenylsulfinylmethyl-1,4-dihydropyridine-3,5-dicarboxylate This was prepared by a procedure similar to that described in Example 1-E, as a yellow solid.

mp 116–117° C. (decomposed). [α]$_D^{25}$–172.11 (c=0.76, MeOH) IR(KBr) 3395, 3325, 1733, 1692, 1646, 1578, 1193, 1155 cm$^{-1}$ $^1$H-NMR (CDCl$_3$) δ8.60 (br.s, 1H), 7.86–7.64 (m, 2H), 7.64–7.40 (m, 3H), 7.28 (d, J=6.6 Hz, 2H), 7.03 (t, J=8.0 Hz, 1H), 5.97 (s, 1H), 4.69-4.49 (m, 1H), 4.21–4.10

(m, 2H), 4.03–3.30 (m, 13H), 3.53 (s, 3H), 3.52 (s, 3H), 1.42–1.12 (m, 3H).

Example 41

(−)-(4S)-Dimethyl 4-(2,6-Dichlorophenyl)-2-(4-(2-methoxycarbonyl)-2-methylpropyl) piperazinylcarbonylmethyl)-6-(S)-phenylsulfinylmethyl-1,4-dihydropyridine-3,5-dicarboxylate monohydrochloride This was prepared by a procedure similar to that described in Example 1-E, as a yellow solid.

mp 138–140° C. (decomposed). $[\alpha]_D^{25}$−184 (c=0.76, MeOH) IR(KBr) 3300, 1724, 1691, 1646, 1633, 1179, 1155 cm$^1$ $^1$H-NMR(DMSO-d6) δ9.52–9.15 (m), 7.85–7.70 (m, 2H), 7.70–7.50 (m, 3H), 7.38 (d, J=8.1 Hz, 2H), 7.18 (t, J=8.4 Hz, 1H), 5.93 (s, 1H), 4.42 (bd, J=12.0 Hz, 1H), 4.31–2.70 (m, 9H), 3.39 (s, 6H), 3.35 (s, 3H), 2.60–2.20 (m, 4H), 1.31 (br.s, 3H), 1.21 (br.s, 3H).

free base $^1$H-NMR (CDCl$_3$) δ8.14 (br.s, 1H), 7.82–7.07 (m, 2H), 7.60–7.43 (m, 3H), 7.27 (d, J=8.0 Hz, 2H), 7.02 (t J=8.0 Hz, 1H), 5.97 (s, 1H), 4.52 (d, J=12.8 Hz, 1H), 4.00–3.72 (m, 3H), 3.66 (s, 3H), 3.53 (s, 6H), 3.70–3.40 (m, 4H), 2.50 (s, 2H), 2.61–2.38 (m, 4H), 1.16 (s, 6H).

Example 42

(−)-(4S)-Dimethyl 4-(2,6-Dichlorophenyl)-2-[4-[3-(4-methylpiperazinyl)-1-oxopropyl) piperazinylcarbonylmethyl]-6-(S)-phenylsulfinylmethyl-1,4-dihydropyridine-3,5-dicarboxylate monohydrochloride This was prepared by a procedure similar to that described in Example 1-E, as a yellow solid.

mp 183–185° C. (decomposed). $[\alpha]_D^{22}$−176 (c=0.895, MeOH) IR(KBr) 3420, 3235, 1694, 1648, 1636, 1631, 1195, 1155 cm$^{-1}$ $^1$H-NMR (DMSO-d6) δ12.20–11.20 (m), 9.38 (br.s, 1H), 7.82–7.70 (m, 2H), 7.70–7.50 (m, 3H), 7.38 (d, J=7.7 Hz, 2H), 7.19 (t, J=8.4 Hz, 1H), 5.93 (s, 1H), 4.42 (d, J=12.1 Hz, 1H), 4.18–3.92 (m, 1H), 3.90–2.60 (m, 22H), 3.47 (s, 3H), 3.39 (s, 3H), 2.50 (s, 3H).

free base $^1$H-NMR (CDCl$_3$) δ8.09 (br.s, 1H), 7.82–7.68 (m, 2H), 7.62–7.42 (m, 3H), 7.27 (d, J=8.1 Hz, 2H), 7.03 (J=8.4 Hz, 1H), 5.98 (s, 1H), 4.71–4.51 (m, 1H), 4.10–3.30 (m, 10H), 3.52 (s, 6H), 3.31–3.08 (m, 1H), 2.81–2.65 (m, 2H), 2.65–2.20 (m, 10H), 2.28 (s, 3H).

Example 43

(−)-(4S)-Dimethyl 4-(2,6-Dichlorophenyl)-2-[4-[3-(4-acetylpiperazinyl)-1-propyl) piperazinylcarbonylmethyl]-6-(S)-phenylsulfinylmethyl-1,4-dihydropyridine-3,5-dicarboxylate monohydrochloride This was prepared by a procedure similar to that described in Example 1-E, as a yellow solid.

mp 205–209° C. (decomposed). $[\alpha]_D^{25}$−159 (C=0.945, MeOH) IR(KBr) 3405, 1691, 1647, 1578, 1568, 1512, 1194, 1158 cm$^{-1}$ $^1$H-NMR (DMSO-d6) δ11.70–11.10 (m), 9.70–9.30 (br.s, 1H), 7.82–7.70 (m, 2H), 7.68–7.50 (m, 3H), 7.38 (d, J=8.1 Hz, 2H), 7.19 (dd, J=8.4, 7.3 Hz, 1H), 5.93 (s, 1H), 4.50–2.50 (m, 24H), 3.47 (s, 3H), 3.46 (s, 3H), 2.39–2.10 (m, 2H), 2.05 (s, 3H).

free base $^1$H-NMR (CDCl$_3$) δ8.14 (br.s, 1H), 7.82–7.68 (m, 2H), 7.60–7.44 (m, 3H), 7.27 (d, J=7.7 Hz, 2H), 7.02 (dd J=8.4, 7.3 Hz, 1H), 5.98 (s, 1H), 4.53 (d, J=12.8 Hz, 1H), 4.02–3.37 (m, 11H), 3.53 (s, 3H), 3.52 (s, 3H), 2.50–2.30 (m, 12H), 2.05 (s, 3H), 2.05 (s, 3H), 1.85–1.58 (m, 2H).

Example 44

(−)-(4S)-Dimethyl 4-(2,6-Dichlorophenyl)-2-{4-(3-pyrrolidino-3-oxo-1-propyl)-1-piperazinyl] carbonylmethyl-6-(S)-phenylsulfinylmethyl-1,4-dihydropyridine-3,5-dicarboxylate monohydrochloride This was prepared by a procedure similar to that described in Example 1-E, as a yellow solid.

mp 168–170° C. (decomposed). $[\alpha]_D^{25}$−174.8 (c=0.945, MeOH) IR(KBr) 3410, 3300, 3225, 1690, 1635, 1577, 1560, 1193, 1155 cm$^{-1}$ $^1$H-NMR(DMSO-d6) δ11.20–10.60 (m), 9.60–9.21 (m, 1H), 7.39–7.50 (m, 5H), 7.38 (d, J=8.1 Hz, 2H), 7.19 (t J=7.7 Hz, 1H), 5.93 (s, 1H), 4.60–2.40 (m, 20H), 3.46 (s, 3H), 3.40 (s, 3H), 2.10–1.64 (m, 4H).

free base $^1$H-NMR (CDCl$_3$) δ8.20 (br.s, 1H), 7.83–7.68 (m, 2H), 7.62–7.43 (m, 3H), 7.26 (d, J=7.3 Hz, 2H), 7.02 (t J=8.1 Hz, 1H), 5.97 (s, 1H), 4.54 (d, J=12.8 Hz, 1H), 4.08–3.30 (m, 11H), 3.53 (s, 3H), 3.52 (s, 3H), 2.83–2.66 (m, 2H), 2.59–2.32 (m, 6H), 2.05–1.07 (m 4H).

Example 45

(−)(4S)-Dimethyl 4-(2,6-Dichlorophenyl)-2-[4-[3-(4-acetylpiperazinyl)-1,3-dioxopropyl] piperazinylcarbonylmethyl]-6-(S)-phenylsulfinylmethyl-1,4-dihydropyridine-3,5-dicarboxylate This was prepared by a procedure similar to that described in Example 1-E, as a yellow solid.

mp 130–133° C. (decomposed). $[\alpha]_D^{25}$−169 (c=0.80; MeOH) IR(KBr) 3465, 3396, 3330, 1698, 1656, 1645, 1618, 1134 cm$^{-1}$ $^1$H-NMR (CDCl$_3$) δ8.01 (br.s, 1H), 7.80–7.68 (m, 2H), 7.62–7.42 (m, 3H), 7.37–7.17 (m, 2H), 7.03 (t J=8.4 Hz, 1H), 5.97 (s, 1H), 4.61 (d, J=12.8 Hz, 0.5H), 4.59 (d, J=13.2, 0.5H), 4.08–3.30 (m, 21H), 3.52 (s, 6H), 2.12 (s, 1.5H), 2.11 (s, 1.5H).

Example 46

(−)-(4S)-Dimethyl 4-(2,6-Dichlorophenyl)-2-[4-[3-(2-oxopyrrolidino)prop-1-yl]piperazinyl] carbonylmethyl-6-(S)-phenylsulfinylmethyl-1,4-dihydropyridine-3,5-dicarboxylate monohydrochloride This was prepared by a procedure similar to that described in Example 1-E, as a yellow solid.

mp160–165° C. (decomposed). $[\alpha]_D^{25}$−173.6 (c=0.675, MeOH) IR(KBr) 3430, 3330, 1687, 1662, 1652, 1155 cm$^{-1}$ $^1$H-NMR (DMSO-d6) δ11.20–10.90 (m), 9.51–9.29 (m), 7.82–7.69 (m, 2H), 7.69–7.50 (m, 3H), 7.38 (d, J=8.1 Hz, 2H), 7.19 (t J=7.7 Hz, 1H), 5.93 (s, 1H), 4.53–2.63 (m, 18H), 3.40 (s, 6H), 2.30–2.12 (m, 2H), 2.06–1.80 (m, 4H).

free base $^1$H-NMR (CDCl$_3$) δ8.11 (br.s, 1H), 7.81–7.70 (m, 2H), 7.62–7.46 (m, 3H), 7.27 (d, J=7.7H, 2H), 7.02 (dd J=8.4, 7.7 Hz, 1H), 5.97 (s, 1H), 4.51 (d, J=12.8 Hz, 1H), 4.00–3.20

(m, 11H), 3.53 (s, 3H), 3.52 (s, 3H), 2.50–2.27 (m), 2.10–1.92 (m, 2H), 1.81–1.60 (m, 4H).

Example 47

(−)-(4S)-Dimethyl 4-(2,6-Dichlorophenyl)-2-[7-(4-benzylpiperazinyl-3azabicyclo[3.3.0]oct-3-ylcarbonylmethyl]-6-(S)-phenylsulfinylmethyl-1,4-dihydropyridine-3,5-dicarboxylate dihydrochloride This was prepared by a procedure similar to that described in Example 1-E, as a yellow solid.

mp 178–180° C. (decomposed). $[\alpha]_D^{25}$ −158.6 (c=0.565, MeOH) IR(KBr) 3425, 3290, 3225, 3065, 1691, 1638, 1509, 1153, 1100 cm$^{-1}$ $^1$H-NMR (DMSO-d6) δ9.39 (br.s, 0.5H), 9.33 (br.s, 0.5H), 7.84–7.70 (m, 2H). 7.70–7.26 (m, 8H), 7.37 (d, J=8.1 Hz, 2H), 7.18 (dd J=8.8, 7.3 Hz, 1H), 5.93 (s, 1H), 4.37 (s, J=12.1 Hz, 0.5H), 4.34 (d, J=12.1 Hz, 0.5H), 4.10–2.40 (m, 20H) 3.40 (s, 3H), 3.38 (s, 3H), 2.40–2.02 (m, 2H), 1.92–1.53 (m, 2H).

free base $^1$H-NMR (CDCl$_3$) δ8.51 (br.s, 1H), 7.80–7.71 (m, 2H), 7.60–7.42 (m, 3H), 7.37–7.16 (m, 7H), 7.00 (dd, J=8.4, 7.7 Hz, 0.5H), 6.99 (dd, J=8.4, 7.7 Hz, 0.5H), 5.97 (s, 1H), 4.52 (d, J=12.8 Hz, 0.5H), 4.51 (d, J=12.8 Hz, 0.5H), 4.15 (d, J=16.1 Hz, 0.5H), 4.00–3.20 (m, 13.5H), 2.90–2.30 (m, 10H), 2.27–2.00 (m, 2H), 1.50–1.22 (m, 2H).

Example 48

(−)-(4S)-Dimethyl 4-(2,6-Dichlorophenyl)-2-[4-(3-acetyl-3-azabicyclo [3.3.0]oct-7-yl) piperazinylcarbonylmethyl]-6-(S)-phenylsulfinylmethyl-1,4-dihydropyridine-3,5-dicarboxylate monohydrochloride This was prepared by a procedure similar to that described in Example 1-E, as a yellow solid.

mp 205–208° C. (decomposed).

$[\alpha]_D^{25}$ −154 (c=0.53, MeOH) IR(KBr) 3485, 3295, 1691, 1623, 1578, 1559, 1568, 1154 cm$^{-1}$ $^1$H-NMR (DMSO-d6) δ11.80–11.30 (m), 9.54–9.25 (m), 7.86–7.50 (m, 5H). 7.38 (d, J=7.7 Hz, 2H), 7.19 (t J=8.0 Hz, 1H), 5.93 (s, 1H), 4.65–1.50 (m, 23H) 3.46 (s, 3H), 3.40 (s, 3H), 1.93 (m, 3H).

free base $^1$H-NMR (CDCl$_3$) δ8.18 (br.s, 1H), 7.84–7.68 (m, 2H), 7.61–7.42 (m, 3H), 7.26(d, J=7.3 Hz, 2H), 7.02 (t J=7.7 Hz, 1H), 5.97 (s, 1H), 4.53 (d, J=12.8 Hz, 1H), 4.10–3.20 (m, 14H), 3.53 (s, 6H), 2.90–2.33 (m, 4H), 2.30–2.06 (m, 2H), 2.03 (s, 3H), 1.45–1.23 (m, 2H).

Example 49

(−)-(4S)-Dimethyl 4-(2,6-Dichlorophenyl)-2-[4-(3-benzoyl-3-azabicyclo[3.3.0]oct-7-yl) piperazinylcarbonylmethyl]-6-(S)-phenylsulfinylmethyl-1,4-dihydropyridine-3,5-dicarboxylate monohydrochloride This was prepared by a procedure similar to that described in Example 1-E, as a yellow solid.

mp 178–180° C. (decomposed). $[\alpha]_D^{25}$ −159.6 (c=0.51, MeOH) IR(KBr) 3486, 3386, 1698, 1646, 1624, 1617, 1575, 1556, 1507, 1154 cm$^{-1}$ $^1$H-NMR (DMSO-d6) δ11.60–11.00 (m), 9.55–9.20 (m, 1H), 7.90–7.30 (m, 12H). 7.19 (t, J=8.0 Hz, 1H), 5.93 (s, 1H), 4.55–1.50 (m, 23H), 3.40 (s, 3H), 3.33 (s, 3H).

free base $^1$H-NMR (CDCl$_3$) δ8.11 (br.s, 1H), 7.83–7.69 (m, 2H), 7.60–7.32 (m, 8H), 7.27 (d, J=8.1 Hz, 2H), 7.02 (t, J=7.3 Hz, 1H), 5.98 (s, 1H), 4.51 (d, J=12.8 Hz, 1H), 4.02–3.20 (m), 3.53 (s, 3H), 3.52 (s, 3H), 2.90–1.10 (m).

Example 50

(−)-(4S)-Dimethyl 4-(2,6-Dichlorophenyl)-2-[4-(1-azabicyclo[2.2.2]oct-3-yl-1-piperazinyl] carbonylmethyl-6-(S)-phenylsulfinylmethyl-1,4-dihydropyridine-3,5-dicarboxylate dihydrochloride This was prepared by a procedure similar to that described in Example 1-E as a yellow solid: mp 203–205° C. (decomposed).

$[\alpha]_D^{-165}$ (c=1.13, MeOH, 27° C.) IR (KBr) 3400, 3379, 3307, 3235, 2949, 1691, 1628, 1514, 1435, 1235, 1294, 1232, 1193, 1105, 1085, 1039. $^1$HNMR (DMSO) δ12.30–12.25 (m), 11.25–11.15 (m), 9.50–9.35 (m), 7.80–7.70 (m, 2H), 7.68–7.56 (m, 3H), 7.38 (d, J=8.2 Hz, 2H), 7.19 (t, J=7.4 Hz, 1H), 5.94 (s, 1H), 4.41 (d, J=12.2 Hz, 1H), 3.85–3.00 (m), 3.47 (s, 3H), 3.41 (s, 3H), 2.64–2.28 (m), 2.04–1.89 (m), 1.86–1.68 (m).

free base $^1$HNMR (CDCl3) δ8.22 (bs, 1H), 7.80–7.70 (m, 2H), 7.60–7.42 (m, 3H), 7.31–7.20 (m, 2H), 7.08–6.95 (m, 1H), 5.97 (s, 1H), 4.54 (dd, J=12.7, 1.6 Hz, 1H), 4.22–3.48 (m, 7H), 3.56 (s, 3H), 3.20–2.57 (m, 5H), 2.47–2.15 (m, 5H), 2.67–1.87 (m, 2H), 1.85–1.68 (m, 2H), 1.50–1.18 (m, 2H).

Preparation 1

1-(N-Methyl-8-azabicyclo[3.2.1]oct-3-yl)-piperazine
A. 1-Benzyl-4-(N-methyl-8-azabicyclo[3.2.1]oct-3-yl)-piperazine hydrochloride To a stirred solution of tropinone (10.2 g, 73.3 mmol) in dry methanol (244 ml) were added 1-benzylpiperazine (12.7 g, 73.3 mmol), activated powdered 3 Å molecular sieves (14 g) and sodium cyanoborohydride (9.7 g, 147 mmol). The reaction mixture was stirred at reflux under nitrogen atmosphere for 50 h. The reaction mixture was then filtered through a pad of celite. The filtrate was concentrated in vacuo. The resulting residue was then treated with 6 N aq. hydrochloric acid, and 2 N aq. hydrochloric acid to pH ~1 under ice-bath cooling, The aqueous solution was concentrated in vacuo and was dissolved in MeOH (100 ml) and EtOH (300 ml). The mixture was filtrated and the insoluble material was washed with EtOH (200 ml) The insoluble material was about 6 g. The filtrate and the washings were combined and concentrated in vacuo to give an oil. This oil was dissolved in IPA (100 ml). After cooling in ice bath, precipitate was collected by suction filtration and washed with IPA (30 ml). The solid was dried in vacuo at 40° C. to give the title compound (15 g). This compound contained a small amount of unreacted benzyl piperazine.

$^1$H-NMR (D$_2$O) δ7.60 (m, 5H), 4.53 (m, 2H), 4.24–4.06 (s, 2H), 3.97–3.40 (m, 9H), 2.85 (s, 3H), 2.60–2.00 (m, 8H).
B. 1-(N-Methyl-8-azabicyclo[3.2.1]oct-3-yl)-piperazine A solution of 1-benzyl-4-(N-methyl-8-azabicyclo[3,2,1] oct-3-yl)-piperazine hydrochloride (14.8 g, 36.4 mmol) in methanol (150 ml) and 6N HCl (32 ml) was hydrogenated at a pressure of 2.0 atm (30 psi) in the presence of 20% palladium hydroxide on carbon (1.5 g) for 12 h. The mixture was then filtered through a pad of celite. The celite pad was washed with MeOH (50 ml) The filtrate and the washings were combined and concentrated to afford a yellow viscous oil. This oil was dissolved in 2N NaOH (150 ml) and to the solution was dropwise added CBZCl (10.4 g, 72.8 mmol)

under ice bath cooling. The mixture was stirred at 0° C. for 5 h. To the mixture was dropwise added 2N HCl at 0° C. to pH 1. The aqueous solution was washed with EtOAc (50 ml×2) to remove bis-(benzyloxycarbonyl)piperazine. The aqueous layer was concentrated in vacuo to give a Z-protected compound. This was dissolved in MeOH (150 ml) and 6N HCl (32 ml) was hydrogenated in the presence of 20% palladium hydroxide on carbon (1.5 g) for 12 h. The mixture was basified with 6N NaOH to pH10. The mixture was filtered through a celite pad and the pad was washed with MeOH (50 ml). The filtrate and the washings were combined and concentrated. The residue was dried azeotropically with EtOH and then toluene. The residue was dissolved in EtOH (150 ml) and insoluble inorganic material was filtered off. The filtrate was concentrated in vacuo to give a white solid and the solid was washed with EtOH-Et$_2$O (1:50) to give the title compound as a white solid (6.4 g, 84%).

$^1$H-NMR (CDCl$_3$): δ3.51–3.80 (m, 2H), 2.80–3.20 (m, 5H), 2.60–2.86 (m, 4H), 2.57 (s, 3H), 2.01–2.32 (m, 4H), 1.58–1.89 (m, 4H).

Preparation 2

1-Methylpyrrolidin-2-ylpiperazine

A. N-(4-Benzylpiperazine) (N-Boc-proline)amide

To a stirred solution of 1-benzylpiperazine (818 mg, 4.65 mmol) and proline (1.00 g, 4.65 mmol) in CH$_2$Cl$_2$ (40 ml) was added WSC (1.07 g, 5.58 mmol) at room temperature. After stirring at room temperature for 3 h, the reaction mixture was then washed with water (15 ml×2), aq. Na$_2$CO$_3$ (10 ml) and brine, then dried (MgSO$_4$) and concentrated in vacuo to afford a yellow oil (1.23 g) in 71% yield. This crude product was pure enough and was used for the following reaction without further purification.

$^1$H-NMR (CDCl$_3$): δ7.38–7.20 (m, 5H), 4.82–4.46 (m, 1H), 3.74–3.21 (m, 8H), 2.63–2.23 (m, 4H), 2.20–1.72 (m, 4H), 1.46, 1.40 (s×2, 9H).

B. N-(4-Benzylpiperazine) proline amide

To a stirred solution of N-(4-benzylpiperazine) (N-Boc-proline)amide (1.22 g, 3.27 mmol) in CH$_2$Cl$_2$ (10 ml) was added TFA (5 ml) slowly at ice-bath cooling. The reaction mixture was stirred at room temperature for 1.5 h. The reaction mixture was then concentrated in vacuo and diluted with aq. 2N HCl (20 ml), and concentrated again. The resulting residue was dried azeotropically with IPA and crystallized in IPA-EtOH-IPE to afford a white crystalline solid (1.04 g). The solid was dissolved in MeOH (5 ml) and basified with 2N NaOH (3 ml). The mixture was then concentrated and dried azeotropically with IPA, The residue was dissolved in hot IPA and filtered to remove insoluble impurities. The filtrate was concentrated to afford a colorless oil (0.82 g, 92% yield).

$^1$H-NMR (CDCl$_3$): δ7.39–7.20 (m, 5H), 3.92–3.79 (m, 1H), 3.71–3.58 (m, 2H), 3.53–3.40 (m, 2H), 3.52 (s, 2H), 3.23–3.10 (m, 1H), 2.88–2.72 (m, 1H), 2.51–2.33 (m, 4H), 2.15–1.55 (m, 4H).

C. N-(4-Benzylpiperazine) (N-formylproline)amide

To a stirred solution of N-(4-benzylpiperazine) proline amide (0.82 g, 3.00 ml) in 15 ml CH$_2$Cl$_2$ was added DCC (1.24 g, 6.00 mmol) and formic acid (276 mg, 6.00 mmol) at room temperature. The reaction mixture was stirred at room temperature for 1.5 h. The mixture was diluted with CH$_2$Cl$_2$ (40 ml) and sat. aq. Na$_2$CO$_3$ (10 ml), water (20 ml), and stirred at room temperature for 16 h. The mixture was then filtered. The water phase was separated and extracted with CH$_2$Cl$_2$ (20 ml×3). The combined extracts were washed with brine, then dried and concentrated in vacuo.

The resulting residue was dissolved in CH$_2$Cl$_2$ (1 ml) and diluted with IPE (15 ml), then filtered to remove the solid. The filtrate was concentrated to afford a colorless oil (0.84 g, 93% yield).

$^1$H-NMR (CDCl$_3$): δ8.27, 8.10 (s×2, 1H), 7.40–7.20 (m, 5H), 4.89–4.56 (m, 1H), 3.78–3.43 (m, 6H), 3.54, 3.52 (s×2, 2H), 2.64–1.80 (m, 8H).

D. 4-Benzyl-1-(1-methylpyrrolidin-2-yl)methylpiperazine

To a stirred solution of N-(4-benzylpiperazine) (N-formylproline)amide (0.844 g, 2.79 mol) in TBF (6 ml) was added BH$_3$.THF (1.0 M in THF, 14 ml) at room temperature. The reaction mixture was stirred at reflux for 19 h. The mixture was then concentrated in vacuo. The residue was acidified with 6N HCl to pH ~1. MeOH was added into the mixture to dissolve the resulting white solid. After stirred at room temperature for 2 h, the mixture was then basified with aq. Na$_2$CO$_3$ to pH ~10. The residual MeOH was removed by evaporation. The resulting residue was extracted with AcOEt (50 ml×3). The combined extracts were washed with brine, dried and concentrated in vacuo. The resulting residue was dissolved in 10% HCl in MeOH solution (10 ml) and was concentrated again. Crystallization of the residue in IPA-AcOEt gave a white solid (727 mg, 68% yield). $^1$H-NMR (D$_2$O, 3HCl salt): δ7.64–7.50 (m, 5H), 4.40 (s, 2H), 3.82–2.68 (m, 13H), 3.02 (s. 3H), 2.45–1.71 (m, 4H).

E. (1-Methylpyrrolidin-2-yl)piperazine Trihydrochloride

This was prepared by a procedure similar to that described in Preparation 1-B, as a white amorphous solid.

$^1$H-NMR (D$_2$O, 3HCl salt): δ3.99–3.18 (m, 13H), 3.06, 3.00 (s×2. 3H), 2.60–1.83 (m, 4H).

Preparation 3

2-(N,N-Dimethylaminomethyl)pyrrolidine dihydrochloride

A. N,N-Dimethylamino N-Boc-proline amide

This was prepared by a procedure similar to that described in Preparation 2-A, as a white solid.

$^1$H-NMR (CDCl$_3$): δ4.82–4.51 (m, 1H), 3.68–3.37 (m, 2H), 3.09, 3.06, 2.97, 2.96 (s×4, 6H), 2.15–1.77 (m, 4H), 1.46, 1.40 (s×2, 9H).

B. 2-(N,N-Dimethylaminomethyl)-pyrrolidine Dihydrochloride

This was converted from a procedure similar to that described in Preparation 2-D and then 2-B, as a colorless amorphous solid $^1$H-NMR (D$_2$O, 2HCl salt): δ4.20–4.05 (m, 1H), 3.76–3.08 (m, 5H), 3.04 (s, 6H), 2.30–1.79 (m, 4H).

Preparation 4

3-Dimethylaminopyrrolidine Dihydrochloride

This was prepared by a procedure similar to that described in Preparation 1-A and then 1-B, as a white solid.

$^1$H-NMR (D$_2$O, 2HCl salt): δ4.31–4.13 (m, 1H), 4.02–3.88 (m, 1H), 3.77–3.41 (m, 3H), 3.03 (s, 6H), 2.80–2.62 (m, 1H), 2.42–2.21 (m, 1H).

Preparation 5

1-Cyclopentylpiperazine Dihydrochloride

This was prepared by a procedure similar to that described in Preparation 1-A, as a white solid $^1$H-NMR (D$_2$O, 2HCl salt): δ12.28–11.70 (m, 1H), 10.08–9.45 (m, 2H), 3.87–3.01 (m, 9H), 2.14–1.35 (m, 8H).

Preparation 6

1-Cyclohexylmethylpiperazine Dihydrochloride

A. 1-Cyclohexylmethyl-4-benzylpiperazine

This was prepared by a procedure similar to that described in Preparation 2-A and then 2-D, as a colorless oil $^1$H-NMR (CDCl$_3$): δ7.41–7.17 (m, 5H), 3.50 (s, 2H), 2.68–2.25 (m, 8H), 2.11 (d, J=7.2 Hz, 2H), 1.83–1.05 (m, 9H), 0.98–0.76 (m, 2H).

B. 1-Cyclohexylmethylpiperazine Dihydrochloride

This was prepared by a procedure similar to that described in Preparation 1-B, as a white solid.

$^1$H-NMR (D$_2$O, 2HCl salt): δ3.81–3.48 (m, 8H), 3.16 (d, J=7.3 Hz, 2H), 2.02–1.61 (m, 7H), 1.42–0.97 (m, 4H).

Preparation 7

2-Pyrrolidino-1-oxoethylpiperazine

A. 4-Benzyl-1-(2-pyrrolidino-1-oxoethyl)piperazine

To a stirred solution of 1-benzylpiperazine (500 mg, 2.84 mmol) and Et$_3$N (1.2 ml, 8.52 mmol) in CH$_2$Cl$_2$ (15 ml) was dropwise added 2-chloroacetyl chloride via syringe at −78° C. After stirred at −78° C. for 1 h, pyrrolidine (0.24 ml, 2.84 mmol) was then added into the stirred reaction mixture at −78° C. The reaction mixture was then stirred at room temperature for 22 h, then diluted with CH$_2$Cl$_2$ (100 ml), the reaction mixture was washed with aq. Na$_2$CO$_3$ (15 ml), brine, then dried (MgSO$_4$) and concentrated in vacuo. Flash chromatography of the residue (Fuji NH-silica gel 200–300 mesh 20 g, eluent solvents: hexane:AcOEt=1:1, 1:2, 1:5, to CH$_2$Cl$_2$:MeOH=200:1, 100:1, 10:1) gave a yellow oil (651 mg, 20% yield).

$^1$H-NMR (CDCl$_3$): δ7.40–7.20 (m, 5H), 3.68–3.52 (m, 4H), 3.51 (s, 2H), 3.29 (s, 2H), 2.63–2.36 (m; 8H), 1.98–1.69 (m, 4H).

B. 2-Pyrrolidino-1-oxoethylpiperazine dihydrochloride

This was prepared by a procedure similar to that described in Preparation 1-B, as a pale yellow solid.

$^1$H-NMR (D$_2$O, 2HCl salt): δ4.47 (s, 2H), 3.98–3.67 (m, 6H), 3.50–3.32 (m. 4H), 3.28–3.13 (m, 2H), 2.31–1.98 (m, 4H).

Preparation 8

N-Methylpiperidin-2-ylmethylpiperazine

A. 4-Benzyl-1-(N-methylpiperidin-2-ylcarbonyl)piperazine

This was prepared by a procedure similar to that described in Preparation 2-A, as a yellow amorphous solid.

$^1$H-NMR (CDCl$_3$): δ7.43–7.21 (m, 5H), 3.86–3.55 (m, 4H), 3.51 (s, 2H), 3.00–2.83 (m, 3H), 2.53–2.36 (m, 4H), 2.23, 2.20 (s×2, 3H), 2.20–1.50 (m, 6H).

B. 4-Benzyl-1-(N-methylpiperidin-2-ylmethyl)piperazine

This was prepared by a procedure similar to that described in Preparation 2-D, as a colorless oil.

$^1$H-NMR (CDCl$_3$): δ7.40–7.15 (m, 5H), 3.49 (s, 2H), 2.94–1.93 (m, 13H), 2.30 (s, 3H), 1.93–1.00 (m, 6H).

C. N-Methylpiperidin-2-ylmethylpiperazine

This was prepared by a procedure similar to that described in Preparation 1-B, as a pale yellow oil.

$^1$H-NMR (CDCl$_3$): δ2.94–2.68 (m, 4H), 2.60–2.00 (m, 9H), 2.31 (s, 3H), 1.92–1.02 (m, 6H).

Preparation 9

4-(N-Boc-amino)-1-cyclohexylpiperazine

A. 4-(N-Boc-amino)-1-cyclohexanol

To a stirred solution of 4-aminocyclohexan-1-ol (5.00 g, 43.4 mmol) in sat. aq. NaHCO$_3$ (40 ml) was added (Boc)$_2$O (9.47 g, 43.4 mmol) in CH$_3$CN (20 ml) at ice-bath cooling. The reaction mixture was stirred at room temperature for 24 h. Diluted with water (100 ml), the mixture was extracted with AcOEt (100 ml×4). The combined extracts were washed with brine, dried and concentrated in vacuo to afford a white crystalline solid (8.46 g, 91% yield).

$^1$H-NMR (CDCl$_3$): δ4.44–4.22 (m, 1H), 3.68–3.52 (m, 1H), 3.51–3.31 (m, 1H), 2.08–1.89 (m, 4H), 1.44 (s, 9H), 1.50–1.07 (m, 4H).

B. 4-(N-Boc-amino)-1-cyclohexanone

To a stirred mixture of the alcohol (8.46 g, 39.3 mmol) in CH$_2$Cl$_2$ (250 ml) was added PCC (30.3 g, 137 mmol) at room temperature. The reaction mixture was heated at reflux for 8 h. The mixture was the cooled to room temperature. Chromatography on silica gel (500 g) eluted with CH$_2$Cl$_2$:MeOH=100:1, 50:1 to 20:1 gave a white solid (7.60 g, 91% yield).

$^1$H-NMR (CDCl$_3$): δ2.47–2.16 (m, 5H), 1.76–1.57 (m, 4H), 1.46 (s, 9H).

C. 4-(N-Boc-amino)-1-cyclohexylpiperazine

This was prepared by a procedure similar to that described in Preparation 1-A, as a white amorphous solid $^1$H-NMR (CDCl$_3$): δ2.87–1.48 (m, 18H), 1.44 (s, 9H).

Preparation 10

4-(N-Boc-N-cyclohexylmethylamino)piperidine

A. 4-(Cyclohexylmethylamino)-1-benzylpiperidine

To a stirred solution of N-(1-benzylpiperidine-4-amino)-4-cyclohexanecarboxamide (784 mg, 2.61 mmol) in THF (10 ml) was added LAH (248 mg, 6.53 mmol) slowly at room temperature. The mixture was stirred at room temperature for 15 h and heated at reflux for 6 h. The mixture was then cooled to room temperature and diluted with Et$_2$O (40 ml), quenched with suitable amount of water very slowly untill a white precipitate appeared. Filtration of the mixture followed by concentration of the filtrate afforded a colorless oil (810 mg), which was pure enough for the following reaction.

$^1$H-NMR (CDCl$_3$): δ7.37–7.18 (m, 5H), 3.49 (s, 2H), 2.90–2.75 (m, 2H), 2.49–2.32 (m, 3H), 2.10–0.77 (m, 17H).

B. 4-(N-Boc-N-cyclohexylmethylamino)-1-benzylpiperidine

This was prepared by a procedure similar to that described in Preparation 9-A, as a colorless oil.

$^1$H-NMR (CDCl$_3$): δ7.38–7.18 (m, 5H), 4.00–3.71 (m, 1H), 3.48 (s, 2H), 3.08–2.85 (m, 4H), 2.11–1.93 (m, 2H), 1.86–0.77 (m, 15H), 1.45 (s, 9H).

C. 4-(N-Boc-N-cyclohexylmethylamino)piperidine

This was prepared by a procedure similar to that described in Preparation 1-B, as a colorless oil.

$^1$H-NMR (CDCl$_3$): δ4.00–3.73 (m, 1H), 3.19–2.89 (m, 4H), 2.73–2.55 (m, 2H), 1.81–0.78 (m, 15H).

Preparation 11

3-[N-Boc-N-(8-Methyl-8-azabicyclo[3.2.1]oct-3-yl)]aminopyrrolidine

A. 3-(8-Methyl-8-azabicyclo[3.2.1]oct-3-yl)amino-1-benzylpyrrolidine

This was prepared by a procedure similar to that described in Preparation 1-A, as a dark brown amorphous solid.

$^1$H-NMR (CDCl$_3$): δ7.37–7.18 (m, 5H), 3.58 (s, 2H), 3.45–3.26 (m, 1H), 3.10–2.98 (m, 2H), 2.89–2.43 (m, 5H), 2.24 (s, 3H), 2.32–1.85 (m, 6H), 1.58–1.37 (m, 4H).

B. 3-[N-Boc-N-(8-Methyl-8-azabicyclo[3.2.1]oct-3-yl)]amino-1-benzylpyrrolidine

This was prepared by a procedure similar to that described in Preparation 9-A; as a yellow oil.

¹H-NMR (CDCl₃): δ7.42–7.19 (m, 5H), 4.67–4.37 (m, 1H), 4.04–3.82 (m, 1H), 3.70 (d, J=12.8 Hz, 1H), 3.51 (d, J=12.8 Hz, 1H), 3.22–3.08 (m, 2H), 2.88–1.97 (m, 10H), 2.18 (s, 3H), 1.85–1.38 (m, 4H), 1.45 (s, 9H).

C. 3-[N-Boc-N-(8-Methyl-8-azabicyclo[3.2.1]oct-3-yl)] aminopyrrolidine

This was prepared by a procedure similar to that described in Preparation 1-B, as a yellow oil.

¹H-NMR (CDCl₃): δ4.42–4.25 (m, 1H), 4.12–3.90 (m, 1H), 3.52–2.98 (m, 6H), 2.41–1.18 (m, 10H), 2.28 (s, 3H), 1.46 (s, 9H).

Preparation 12

Piperazine N-Boc-dimethylglycine amide

A. 4-Benzylpiperazine N-Boc-dimethylglycine amide

This was prepared by a procedure similar to that described in Preparation 2-A, as a white solid.

¹H-NMR (CDCl₃): δ7.37–7.20 (m, 5H), 3.82–3.65 (m, 4H), 3.50 (s, 2H), 2.48–2.38 (m, 4H), 1.49 (br.s, 6H), 1.43 (s, 9H).

B. Piperazine N-Boc-dimethylglycine amide

This was prepared by a procedure similar to that described in Preparation 1-B, as a colorless amorphous solid.

¹H-NMR (CDCl₃): δ5.45–5.11 (m, 1H), 3.88–3.60 (m, 4H), 2.95–2.78 (m, 4H), 1.49 (s, 6H), 1.44 (s, 9H).

Preparation 13

12-(N-Boc-amino)-2-methylprop-1-yl]piperazine

A. 4-Benzyl-[2-(N-Boc-amino)-2-methylprop-1-yl]piperazine

This was prepared by a procedure similar to that described in Preparation 2-D, as a colorless oil.

¹H-NMR (CDCl₃): δ7.35–7.21 (m, 5H), 4.99–4.81 (m, 1H), 3.49 (s, 2H), 2.66–2.34 (m, 8H), 2.41 (s, 2H), 1.43 (s, 9H), 1.24 (s, 6H).

B. [2-(N-Boc-amino)-2-methylprop-1-yl)]piperazine

This was prepared by a procedure similar to that described in Preparation 1-B, as a pale yellow oil.

¹H-NMR (CDCl₃): δ4.98–4.82 (m, 1H), 2.94–2.80 (m, 4H), 2.63–2.45 (m, 4H), 2.41 (s, 2H), 1.46 (s, 9H), 1.43 (s, 6H).

Preparation 14

(S)-2-(Piperazinylmethyl)-1-methylpyrrolidine

A. (S)-2-[(4-Benzylpiperazinylmethyl)]-1-methylpyrrolidine

This was prepared by a procedure similar to that described in Preparation 10-A, as a colorless oil.

¹H-NMR (CDCl₃): δ7.35–7.18 (m, 5H), 3.50 (s, 2H), 3.13–2.97 (m, 1H), 2.39 (s, 3H), 2.60–1.43 (m, 16H). [α]$_D^{24}$ −44.0° (c=0.595, MeOH)

B. (S)-2-(piperazinylmethyl)-1-methylpyrrolidine

This was prepared by a procedure similar to that described in Preparation 1-B, as a colorless oil.

[α]$_D^{24}$ −75.0° (c=0.520, MeOH) ¹H-NMR (CDCl₃): δ3.13–2.10 (m, 13H), 2.41 (s. 3H), 2.06–1.47 (m, 4H).

Preparation 15

(R)-2-(Piperazinylmethyl)-1-methylpyrrolidine

A. (R)-2-[(4-Benzylpiperazinylmethyl)]-1-methylpyrrolidine

This was prepared by a procedure similar to that described in Preparation 10-A, as a colorless oil.

¹H-NMR (CDCl₃): δ7.35–7.19 (m, 5H), 3.50 (s, 2H), 3.09–2.98 (m, 1H), 2.62–2.09 (m, 12H), 2.39 (s, 3H), 2.06–1.43 (m, 4H).

[α]$_D^{25}$ +42.7° (c=0.525, MeOH)

B. (R)-2-(piperazinylmethyl)-1-methylpyrrolidine

This was prepared by a procedure similar to that described in Preparation 1-B, as a colorless oil.

[α]$_D^{23}$ +68.2° (c=0.660, MeOH)

¹H-NMR (CDCl₃): δ3.11–2.10 (m, 13H), 2.41 (s. 3H), 2.04–1.46 (m, 4H).

Preparation 16

1-[2-(1-Pyrrolidino)eth-1-yl]piperazine

This was prepared by a procedure similar to that described in Preparation 10-A, as a colorless oil.

¹H-NMR (CDCl₃) δ2.98–2.72 (m, 4H), 2.72–2.30 (m, 12H), 2.09–1.58 (m, 5H).

Preparation 17

1-(8-Acetyl-8-azabicyclo[3.2.1]oct-3-yl) piperazine Dihydrochloride

This was prepared by a procedure similar to that described in Preparation 1, as a colorless oil.

¹H-NMR (DMSO-d₆) δ5.98–5.00 (m), 4.62–4.48 (m, 1H), 4.42–4.27 (m, 1H), 3.92–3.11 (m), 2.22–1.50 (m), 1.97 (m, 3H).

Preparation 18

1-(8-Ethyl-8-azabicyclo[3.2.1]oct-3-yl) piperazine

This was prepared by a procedure similar to that described in Preparation 10-A, as a colorless oil.

¹H-NMR (CDCl₃) δ3.41–3.19 (m, 2H), 2.99–2.68 (m, 4H), 2.65–2.30 (m, 6H), 2.12–1.38 (m, 10H), 1.07 (t, J=7.3 Hz, 3H).

Preparation 19

1-(8-Isopropyl-8-azabicyclo[3.2.1]oct-3-yl) piperazine

This was prepared by a procedure similar to that described in Preparation 1, as a pale yellow solid ¹H-NMR (CDCl₃) δ3.55–3.38 (m, 2H), 2.95–2.70 (m, 4H), 2.58–2.28 (m, 4H), 2.21–1.29 (m, 10H), 1.00 (t, J=5.8 Hz, 6H).

Preparation 20

1-[3-(4-Methylpiperazin-1-yl))-3-oxoprop-1-yl]-piperazine

A. 4-Methylpiperazin-1-yl 3-(1-benzylpiperazin-4-yl) propionyl amide

A mixture of 85% pure 4-methylpiperazin-1-yl acrylamide (2.23 g, 12.3 mmol) and benzylpiperazine (2.6 ml, 14.8 mmol) in benzene (20 ml) was heated at 80° C. for 20 h. After cooling down, the solvent was evapolated and the resulting residue was purified by a silica gel column chromatography (NH gel 200–300 mesh (100 g), CH₂Cl₂:MeOH=100:0.5–100:1) to give 4-benzylpiperazin-1-yl 3-(1-tert-butoxycarbonylpiperazin-4-yl)propionyl amide (4.2 g, quant.) as a pale yellow oil.

¹H-NMR (CDCl₃) δ7.38–7.19 (m, 5H), 3.51 (s, 2H), 3.69–3.58 (m, 2H), 3.55–3.40 (m, 2H), 2.93–2.21 (m, 16H), 2.29 (s, 3H)

B. 1-[3-(4-Methylpiperazin-1-yl)-3-oxoprop-1-yl]piperazine

This was prepared by a procedure similar to that described in Preparation 1-B, as a colorless oil.

¹H-NMR (CDCl₃) δ3.69–3.56 (m, 2H), 3.53–3.41 (m, 2H), 2.95–2.80 (m, 4H), 2.76–2.61 (m, 2H), 2.58–2.20 (m, 13H), 1.83–1.64 (m, 1H).

Preparation 21

1-[3-(4-Methylpiperazin-1-yl)prop-1-yl]piperazine

This was prepared by a procedure similar to that described in Preparation 10-A, as a pale yellow oil.

¹H-NMR (CDCl₃) δ3.78–3.61 (m, 1H), 2.98–2.80 (m, 4H), 2.80–2.20 (m, 16H), 2.28 (s, 3H), 1.80–1.59 (m, 2H).

Preparation 22

1-[3-(1-Pyrrolidino)propyl]piperazine

This was prepared by a procedure similar to that described in Preparation 10-A, as pale yellow oil.

¹H-NMR (CDCl₃) δ2.98–2.73 (m, 4H), 2.62–2.20 (m, 12H), 1.88–1.45 (m, 7H).

Preparation 23

Ethyl (1-Piperazinyl)acetate

This was prepared by a procedure similar to that described in Preparation 10-A, as a colorless oil.

¹H-NMR (CDCl₃) δ4.19 (q, J=7.3 Hz, 1H), 3.19 (s, 2H), 3.01–2.84 (m, 4H), 2.64–2.42 (m, 4H), 1.65 (br.s, 1H), 1.28 (t, J=7.3 Hz, 3H).

Preparation 24

1-(8-Methyl-8-azabicyclo[3.2.1]oct-3-yl) homopiperazine Trihydrochloride

This was prepared by a procedure similar to that described in Preparation 1, as a colorless powder.

¹H-NMR (CDCl₃) δ3.41–3.19 (m, 2H), 2.99–2.68 (m, 4H), 2.65–2.30 (m, 6H), 2.12–1.38 (m, 10H), 1.07 (t, J=7.3 Hz, 3H).

¹H-NMR (DMSO-d₆) δ12.00–10.90 (m), 10.29–9.20 (m), 5.04–4.18 (m), 4.18–3.02 (m), 3.02–1.70 (m).

Preparation 25

Ethyl 3-(1-piperazinyl)-3-oxopropionate

This was prepared by a procedure similar to that described in Preparation 2-A, as a colorless oil.

¹H-NMR (CDCl₃) δ4.21 (q, J=7.3 Hz, 2H), 3.70–3.56 (m, 2H), 3.46 (s, 2H), 3.53–3.36 (m, 2H), 2.96–2.79 (m, 4H), 1.77 (s, 1H), 1.29 (t, J=7.3 Hz, 3H).

Preparation 26

Methyl 3-(1-Piperazinyl)-2,2-dimethylpropionate
A. Methyl 3-(4-benzylpiperazin-1-yl)-2,2-dimethyl-3-oxo-propionate To a solution of Methyl 3-(4-benzylpiperazin-1-yl)-3-oxo-propionate (1.02 g, 3.517 mmol) at THF (35 ml) was added NaH (352 mg, 8.79 mmol) at ice-cooling bath temp. After 5 min, MeI (0.48 mmol) was added at 0° C. The mixture was stirred for 3 h. After quenching with H₂O (10 ml), the mixture was extracted with EtOAc (30 ml×2), AcOEt layer was washed with brine (5 ml), dried over Na2SO4, filtered and evaporated. The residue was purified by a silica gel column (30 g) eluted with CH₂Cl₂-MeOH= 100:3) to give the corresponding dimethyl derivative (879 mg, 78.6%) as a colorless viscous oil.

NMR (CDCl₃) δ7.40–7.18 (m, 5H), 4.16 (q, 7.3 Hz, 2H), 3.80–3.10 (m, 4H), 3.50 (s, 2H), 2.50–2.30 (m, 4H), 1.42 (s, 6H), 1.25(t, J=7.4 Hz, 3H).

B. 3-(4-Benzylpiperazin-1-yl)-2,2-dimethylpropan-1-al

Methyl 3-(4-benzylpiperazin-1-yl)-2,2-dimethyl-3-oxo-propionate was reduced to the corresponding 3-(4-benzylpiperazin-1-yl)-2,2-dimethylpropan-1-ol by a procedure similar to that described in Preparation 10-A. Without purification, the product (290 mg, 1.11 mmol) was dissolved in DMSO (3.3 ml) and Et₃N (1.3 ml) followed by SO₃.pyridine (883 mg, 5.55 mmol) were added at room temperature and the mixture was stirred for 1 hr. After diluted with (50 ml), the mixture was washed with H₂O (5 ml×4) and brine (5 ml). Organic layer was dried over Na₂SO₄, filtered and evaporated. The residue was purified by a column chromatography on silica gel (15 g) eluted with CH₂Cl₂-MeOH (20:1) to give an aldehyde (252 mg, 97.7%) as a yellow oil.

NMR (CDCl₃) δ9.54 (s, 1H), 7.36–7.15 (m, 5H), 3.47 (s, 2H), 2.47 (s, 2H), 2.59–2.28 (m, 8H), 1.09 (s, 6H).

C. Methyl 3-(4-benzylpiperazin-1-yl)-2,2-dimethylpropionate

To a solution of I2 (413 mg, 1.63 mmol) in MeOH (3 ml) was added finely powdered KOH (215 mg, 3.255 mmol) at room temperature, followed by a solution of amino aldehyde (282 mg, 1.085 mmol) in MeOH (3 ml). The mixture was stirred for 1 h after addition of 5% Na₂S₂O₃, The mixture was extracted with CH₂Cl₂ (30 ml×2). Organic layer was washed with brine (5 ml), dried over MgSO₄, filtered and evaporated. The residue was purified by a silica gel column chromatography (20 g), eluted with CH₂Cl₂-MeOH=100:3) to give the corresponding ester (256 mg, 81.4%) as a white solid.

NMR (CDCl3) δ7.34 (m, 5H), 3.64 (s, 3H), 3.47 (s, 2H), 2.48 (s, 2H), 2.58–2.30 (m, 8H)

D. Methyl 3-(1-piperazinyl)-2,2-dimethylpropionate

This was prepared by a procedure similar to that described in Preparation 1-B, as a colorless solid.

¹H-NMR (CDCl₃) δ3.66 (s, 3H), 3.38–3.01 (m, 1H), 2.96–2.82 (m, 4H), 2.65–2.41 (m, 4H), 2.48 (s, 2H), 1.16 (s, 6H).

Preparation 27

1-[3-(4-Methylpiperazinyl)-1-oxoprop-1-yl] piperazine

This was prepared by a procedure similar to that described in Preparation 1-B, as a pale yellow oil.

¹H-NMR (CDCl₃) δ3.72–3.52 (m, 2H), 3.52–3.30 (m, 2H), 3.00–2.65 (m, 6H), 2.65–2.20 (m, 10H), 2.28 (s, 3H), 2.00–1.62 (m, 1H).

Preparation 28

1-[3-(1-Pyrrolidino)-3-oxoprop-1-yl]piperazine

This was prepared by a procedure similar to that described in Preparation 1-B, as a pale brown oil.

¹H-NMR (CDCl₃) δ3.58–3.30 (m, 4H), 2.98–2.82 (m, 4H), 2.80–2.66 (m, 2H), 2.60–2.30 (m, 8H), 2.08–1.60 (m, 7H).

Preparation 29

1-[3-(4-Acetylpiperazin-1-yl)prop-1-yl]piperazine

This was prepared by a procedure similar to that described in Preparation 1-B, as a pale yellow oil.

$^1$H-NMR (CDCl$_3$) δ3.68–3.56 (m, 2H), 3.52–3.40 (m, 2H), 2.98–2.81 (m, 4H), 2.55–2.25 (m, 12H), 2.08 (s, 3H), 1.80–1.60 (m, 3H).

Preparation 30

1-Benzylpiperidin-4-ylamino N-Boc-glycine amide

This was prepared by a procedure similar to that described in Preparation 2-A, as a white solid.

$^1$H-NMR (CDCl$_3$): δ7.38–7.20 (m, 5H), 6.58–6.27 (m, 1H), 4.95–4.68 (m, 1H), 3.88–3.68 (m, 1H), 3.49 (s, 2H), 2.87–2.68 (m, 2H), 2.24–2.07 (m, 2H), 1.97–1.82 (m, 2H), 1.72–1.40 (m, 2H), 1.46 (s, 6H), 1.44 (s, 9H).

Preparation 31

Piperidin-4-ylamino N-Boc-glycine amide

This was prepared by a procedure similar to that described in Preparation 1-B, as a white solid $^1$H-NMR (CDCl$_3$): δ6.63–6.23 (m, 1H), 5.01–4.73 (m, 1H), 3.96–3.73 (m, 1H), 3.16–2.98 (m, 2H), 2.81–2.64 (m, 2H), 2.06–1.81 (m, 2H), 1.47 (s, 6H), 1.44 (s, 9H), 1.56–1.20 (m, 2H).

Preparation 32

1-Benzyl-4-pivaloylpiperazine

This was prepared by a procedure similar to that described in Preparation 2-A, as a white solid.

$^1$H-NMR (CDCl$_3$): δ7.38–7.21 (m, 5H), 3.70–3.58 (m, 4H), 3.51 (s, 2H), 2.48–2.37 (m, 4H), 1.28 (s, 9H).

Preparation 33

1-Pivaloylpiperazine

This was prepared by a procedure similar to that described in Preparation 1-B, as a pale yellow amorphous solid.

$^1$H-NMR (CDCl$_3$): δ3.68–3.58 (m, 4H), 2.91–2.82 (m, 4H), 1.28 (s, 9H).

Preparation 34

1-Benzylpiperazine N-carbamoylglycine amide

This was prepared by a procedure similar to that described in Preparation 2-A, as a white solid.

$^1$H-NMR (DMSO-d$_6$): δ7.39–7.19 (m, 5H), 6.50 (br.s, 1H), 5.40 (s, 2H), 3.75–3.34 (m, 4H), 3.44 (s, 2H), 2.38–2.22 (m, 4H), 1.29 (s, 6H).

Preparation 35

Piperazine N-carbamoylglycine amide

This was prepared by a procedure similar to that described in Preparation 1-B, as a white solid.

$^1$H-NMR (DMSO-d$_6$): δ6.49 (br.s, 1H), 5.38 (s, 2H), 3.59–3.3 (m, 4H), 2.66–2.54 (m, 4H), 1.29 (s, 6H).

Preparation 36

4-(2,2-Dimethyl-3-hydroxypropionyl) 1-benzylpiperazine

This was prepared by a procedure similar to that described in Preparation 2-A, as a white solid.

$^1$H-NMR (CDCl$_3$): δ7.39–7.22 (m, 5H), 3.78–3.58 (m, 5H), 3.51 (s, 2H), 3.47 (d, J=6.6 Hz, 2H), 2.50–2.38 (m, 4H), 1.26 (s, 6H).

Preparation 37

4-(2,2-Dimethyl-3-hydroxypropionyl)piperazine

This was prepared by a procedure similar to that described in Preparation 1-B, as a white solid.

$^1$H-NMR (CDCl$_3$): δ3.67–3.57 (m, 4H), 3.49 (s, 2H), 2.91–2.82 (m, 4H), 1.27 (s, 6H).

Preparation 38

4-(2,2-Dimethyl-3-hydroxyprop-1-yl)piperazine

This was prepared by a procedure similar to that described in Preparation 2-D, as a color less oil.

$^1$H-NMR (CDCl$_3$): δ3.49 (s, 2H), 2.96–2.80 (m, 4H), 2.69–2.36 (m, 4H), 2.38 (s, 2H), 0.93 (s, 6H).

Preparation 39

1-Benzyl-4-(3-oxobut-1-yl)piperazine

This was prepared by a procedure similar to that described in Preparation 23-A, as a yellow oil.

$^1$H-NMR (CDCl$_3$): δ7.37–7.19 (m, 5H), 3.50 (s, 2H), 2.72–2.57 (m, 4H), 2.57–2.32 (m, 8H), 2.16 (s, 3H).

Preparation 40

1-Benzyl-4-(3-hydroxy-3-methylbut-1-yl)piperazine

To a stirred solution of 1-benzyl-4-(3-oxo-but-4-yl) piperazine (500 mg, 2.03 mmol) in THF (10 ml) was slowly added MeMgCl (3.0 M in THE, 1.4 ml, 4.06 mmol) at room temperature. The reaction mixture was stirred at room temperature for 24 h. The mixture was diluted with CH$_2$Cl$_2$ (30 ml), and then acidified with 2N HCl (5 ml) to pH ~2. The pH value was then adjusted to ~10 by aq Na$_2$CO$_3$ solution. The water phase was extracted with CH$_2$Cl$_2$ (20 ml×3). The combined CH$_2$Cl$_2$ extracts were washed with brine, then dried over MgSO$_4$ and concentrated in vacuo to afford a brown oil (494 mg, 93% yield). This product was used for the following reaction without further purification.

$^1$H-NMR (CDCl$_3$): δ7.36–7.18 (m, 5H), 3.49 (s, 2H), 2.75–2.23 (m, 10H), 1.65–1.57 (m, 2H), 1.21 (s, 6H).

Preparation 41

4-(3-Hydroxy-3-methylbut-1-yl)piperazine Dihydrochloride

This was prepared by a procedure similar to that described in Preparation 1-B, as a yellow amorphous solid.

$^1$H-NMR (D$_2$O, 2HCl salt): δ3.86–3.54 (m, 8H), 3.51–3.38 (m, 2H), 2.06–1.93 (m, 2H), 1.31 (s, 6H).

Preparation 42

Synthesis of azabicyclo[3.2.1]octane derivatives
A. N-t-Butoxycarbonyl-N-propargylallylamine In a 100 ml round bottom flask, KH (1.09 g, 9.55 mmol) was placed and it was washed with hexane (2 ml×3). DMF (20 ml) was added and the resulting suspension was cooled in ice-bath. A solution of N-t-Butoxycarbonylallylamine (1.0 g, 6.37 mmol) in DMF (5 ml) was added dropwise to the stirred KH suspension during a period of 15 min. at the same temperature, then for 15 min. at room temperature. The mixture was cooled in ice bath and propargyl bromide (1.1 ml, 12.74 mmol) was added dropwise to the mixture. The resulting mixture turned to black and the mixture was stirred for 20 min. at the same temperature. The excess reagent was quenched by MeOH and the mixture was diluted with AcOEt (200 ml). The mixture was washed with H$_2$O (20 ml×5) and brine (20 ml). The organic layer was dried over MgSO$_4$, filtered and evaporated. The residue was purified by a silica gel column (230–400 mesh, 50 g, hexane:AcOEt= 9:1) to give N-t-Butoxycarbonyl-N-propargylallylamine (1.12 g, 90% yield) as a yellow oil.

$^1$H-NMR (CDCl$_3$) δ5.76 (ddt, J=16.9, 14.0, 4.0 Hz, 1H), 5.31–5.08 (m, 2H), 4.17–3.80 (m, 4H), 2.19 (t, J=2.6 Hz, 1H), 1.49 (s,9H).

B. N-t-Butoxycarbonyl-5 azabicyclo[3.3.0]oct-2-en-1-one

In a 1 l round bottom flask, Co$_2$(CO)$_8$ (9.3 g, 27.08 mmol) was placed and CH$_2$Cl$_2$ (200 ml) was added. To this solution, a solution of N-t-Butoxycarbonyl-N-propargylallylamine (4.8 g, 24.6 mmol) in CH$_2$Cl$_2$ (200 ml) was added and the resulting mixture was stirred for 1 h. NMO (20 g, 172.2 mmol) was portionwise added to the mixture during a period of 1 h. Then, the mixture was stirred for 2 h. The excess reagent was removed by a short silica gel column (400 g, AcOEt as eluent) and the solvent of eluent was evaporated. The residue was purified by a silica gel column (150 g, hexane:AcOEt=3:1) to give N-1-Butoxycarbonyl-5 azabicyclo[3.3.0]oct-2-ene-1-one (3.5 g, 64% yield) as a pale brown solid.

$^1$H-NMR (CDCl$_3$) δ6.15–6.00 (m, 1H), 4.40–3.92 (m, 3H), 3.40–3.10 (m, 1H), 3.00–2.55 (m, 2H), 2.29–2.10 (m, 1H), 1.49 (s, 9H).

C. N-t-Butoxycarbonyl-5 azabicyclo[3.3.0]octanone

A mixture of the enone (3.5 g, 15.69 mmol) and Pd-C (350 mg) in AcOEt (50 ml) was stirred under H$_2$ for 6 h. After the mixture was filtered through a celite pad, the filtrate was concentrated in vacuo. The residue was purified by a silica gel column (230–400 mesh, 40 g, hexane:AcOEt=2:1–1:1) to give N-t-Butoxycarbonyl-5 azabicyclo[3.3.0]octanone (3.6 g, quant.) as a colorless crystal.

$^1$H-NMR (CDCl$_3$) δ3.83–3.53 (m, 2H), 3.35–3.01 (m, 2H), 3.04–2.82 (m, 2H), 2.60–2.39 (m, 2H), 2.16 (dd, J=19.8, 5.1 Hz, 2H), 1.46 (s, 9H).

D. 1-Benzyl-4-(3-azabicyclo[3.3.0]oct-7-yl)piperazine

This was prepared by benzylation followed by a procedure similar to that described in Preparation 2-B, as a colorless solid. 7.40–7.16 (m, 5H), 3.50 (s, 2H), 2.96–2.00 (m, 18H), 1.20–0.92 (m, 2H).

E. 4-(3-Acetyl-3-azabicyclo[3.3.0]oct-7-yl)piperazine

This was prepared by acetylation followed by a procedure similar to that described in Preparation 1-B, as a colorless oil.

$^1$H-NMR (CDCl$_3$) δ3.73–3.41 (m, 4H), 3.33 (dd, J=10.6, 4.4 Hz, 1H), 3.00–2.80 (m, 4H), 2.80–2.30 (m, 6H), 2.30–2.08 (m, 2H), 2.02 (s, 3H), 1.70 (br.s, 1H), 1.48–1.21 (m, 2H).

Preparation 43

1-Benzyl-4-(3-benzoyl-3-azabicyclo[3.3.0]oct-7-yl) piperazine

This was prepared by benzylation followed by a procedure similar to that described in Preparation 1-B, as a colorless oil.

7.55–7.16 (m, 10H), 3.90–3.12 (m, 4H), 2.90–1.94 (m, 13H), 3.51 (s, 2H), 1.51–1.11 (m, 2H).

In addition, the chemical structure of the compounds prepared in the examples are summarized in the following Table.

TABLE

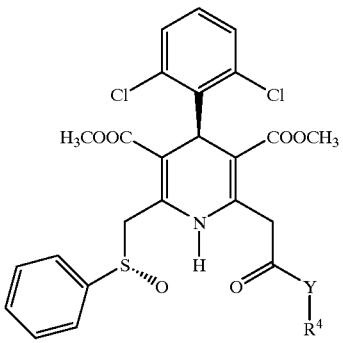

| Ex. # | R$^4$—Y— |
|---|---|
| 1 | 4-(8-methyl-8-azabicyclo[3.2.1]oct-3-yl)-1-piperazinyl |
| 2 | 4-(2-(1-pyrrolidinoethyl)-1-piperaziny |
| 3 | 4-(8-acetyl-8-azabicyclo[3.2.1]oct-3-yl)-1-piperazinyl |
| 4 | 4-(8-ethyl-8-azabicyclo[3.2.1]oct-3-yl)-1-piperazinyl |
| 5 | 4-(8-isopropyl-8-azabicyclo[3.2.1]oct-3-yl)-1-piperazinyl |
| 6 | 4-(3-(1-pyrrolidinopropyl)-1-piperazinyl |
| 7 | 4-(8-benzyl-8-azabicyclo[3.2.1]oct-3-yl)-1-piperazinyl |
| 8 | 4-ethoxycarbonylpiperazinyl |
| 9 | 4-cyclohexylmethyl-1-piperazinyl |
| 10 | (R,S)-3-(dimethylamino)pyrrolidino |
| 11 | 4-(4-aminocyclohexyl)-1-piperazinyl |
| 12 | 4-[(2R,S)-1-methyl-2-pyrrolidinyl]methyl-1-piperazinyl |
| 13 | 4-[(2S)-1-methyl-2-pyrrolidino]-1-piperazinyl |
| 14 | 4-[(2R)-1-methyl-2-pyrrolidino]-1-piperazinyl |
| 15 | (R,S)-2-(dimethylamino)methylpyrrolidino |
| 16 | 4-(1-piperidino)piperidino |
| 17 | 4-[(2R,S)-1-methyl-2-piperidinyl]methyl-1-piperazinyl |
| 18 | 4-cyclopentyl-1-piperazinyl |
| 19 | 4-[2-(1-pyrrolidino)-acetyl]-1-piperazinyl |
| 20 | 4-cyclohexylmethylamino piperidino |
| 21 | (3S)-3-(N-methyl-8-azabicyclo[3,2,1]oct-7-yl)amino-1-pyrrolidino |
| 22 | 4-(8-methyl-8-azabicyclo[3.2.1]oct-3-yl)-2,3,4,5,6,7-hexahydro-1H-1,4-diazepin-1-yl |
| 23 | 4-(2-amino-2-methyl)propionyl-1-piperazinyl |
| 24 | 4-(2-acetylamino-2-methyl)propionyl-1-piperazinyl |
| 25 | HOOC—CH$_2$-piperazinyl |
| 26 | 4-(2-amino-2-methyl)propyl-1-piperazinyl |
| 27 | 4-(2-acetylamino-2-methyl)propyl-1-piperazinyl |
| 28 | 4-methyl-1-piperazinyl |
| 29 | 4-(3-oxo-bicyclo[3,3,0]oct-7-yl)-1-piperazinyl |
| 30 | 4-[1-(methoxycarbonylmethyl)cyclopent-1-ylacetyl]piperazin-1-yl |
| 31 | 4-[2-amino-2-methylpropionylamino]-1-piperidinyl |
| 32 | 4-(2,2-dimethyl)propionyl-1-piperazinyl |
| 33 | 4-[2-(N-carbamoyl)amino-2-methyl]propionyl-1-piperazinyl |
| 34 | 4-(2,2-dimethyl-3-hydroxy)propionyl-1-piperazinyl |
| 35 | 4-(2,2-dimethyl-3-hydroxy)propyl-1-piperazinyl |
| 36 | 4-(3-hydroxy-3-methyl)butyl-1-piperazinyl |
| 37 | 4-carbamoylmethylpiperazinyl |
| 38 | 4-(3-(4-methylpiperazinyl)propyl)piperazinyl |
| 39 | 4-[3-(4-methylpiperazinyl)-3-oxopropyl)piperazinyl |
| 40 | 4-(ethoxy-3-oxopropionyl)piperazinyl |
| 41 | 4-(2-methoxycarbonyl)-2-methylpropyl)piperazinyl |
| 42 | 4-[3-(4-methylpiperazinyl)-1-oxopropyl)piperazinyl |
| 43 | 4-[3-(4-acetylpiperazinyl)-1-propyl)piperazinyl |
| 44 | 4-(3-pyrrolidino-3-oxo-1-propyl)-1-piperazinyl |
| 45 | 4-[3-(4-acetylpiperazinyl)-1,3-dioxopropyl]piperazinyl |
| 46 | 4-[3-(2-oxopyrrolidino)prop-1-yl]piperazinyl |
| 47 | 7-(4-benzylpiperazinyl)-3-azabicyclo[3.3.0]oct-3-yl |
| 48 | 4-(3-acetyl-3-azabicyclo[3.3.0]oct-7-yl)piperazinyl |
| 49 | 4-(3-benzoyl-3-azabicyclo[3.3.0]oct-7-yl)piperazinyl |
| 50 | 4-(1-azabicyclo[2.2.2]oct-3-yl)-1-piperazinyl |

What is claimed is:
1. A compound of the formula (I):

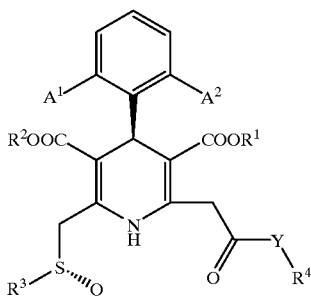

(I)

and its pharmaceutically acceptable salts, wherein
$A^1$ and $A^2$ are each halo;
$R^1$ and $R^2$ are independently $C_{1-4}$ alkyl;
$R^3$ is phenyl or naphthyl, optionally substituted with up to three substituents independently selected from halo, hydroxy, $C_{1-4}$ alkyl, halo $C_{1-4}$ alkyl and $C_{1-4}$ alkoxy;
Y is heterocyclic group selected from $C_{5-10}$ azacycloalkyl, $C_{6-10}$ diazacycloalkyl or $C_{7-10}$ azabicycloalkyl, the heterocyclic group being optionally substituted with up to two substituents independently selected from $C_{1-4}$ alkyl, halo $C_{1-4}$ alkyl and $C_{1-4}$ alkoxy; and
$R^4$ is selected from the following:
(a) $C_{1-8}$ alkyl optionally substituted with up to five substituents independently selected from halo, hydroxy, amino, mono- or di-$C_{1-4}$ alkylamino, carbamoyl, carboxy, oxo, $C_{1-4}$ alkyl, $C_{1-4}$ alkoxy, $C_{2-6}$ alkanoylamino, $C_{1-4}$ alkoxycarbonyl, $C_{3-8}$ cycloalkyl, $C_{5-10}$ azacycloalkyl, $C_{7-10}$ azabicycloalkyl and $C_{6-10}$ diazacycloalkyl, wherein the azacycloalkyl, azabicycloalkyl and diazacycloalkyl are optionally substituted with up to two substituents independently selected from halo, hydroxy, $C_{1-4}$ alkyl, amino, oxo and $C_{2-6}$ alkanoyl;
(b) amino optionally substituted with up to two substituents independently selected from $C_{1-4}$ alkyl, halo $C_{1-4}$ alkyl, amino-$C_{2-4}$ alkanoyl optionally substituted with $C_{1-3}$ alkyl, $C_{3-8}$ cycloalkyl-$C_{1-4}$ alkyl and $C_{5-14}$ azabicycloalkyl optionally substituted with up to two substituents independently selected from $C_{1-4}$ alkyl, $C_{2-6}$ alkanoyl and phenyl-$C_{1-4}$ alkyl and benzoyl;
(c) $C_{2-6}$ alkanoyl optionally substituted with up to two substituents independently selected from halo, hydroxy, amino, $C_{1-4}$ alkyl, halo $C_{1-4}$ alkyl, acetylamino, carbamoylamino, $C_{1-4}$ alkoxy, $C_{1-4}$ alkoxycarbony-$C_{1-4}$ alkyl, $C_{5-10}$ azacycloalkyl, $C_{6-10}$ diazacycloalkyl and $C_{3-8}$ cycloalkyl optionally substituted with $C_{1-4}$ alkoxycarbony-$C_{1-4}$ alkyl;
(d) $C_{3-8}$ cycloalkyl or $C_{7-14}$ bicycloalkyl, wherein the cycloalkyl and bicycloalkyl are optionally substituted with up to two substituents independently selected from halo, hydroxy, amino, oxo, $C_{1-4}$ alkyl, halo $C_{1-4}$ alkyl and $C_{1-4}$ alkoxy;
(e) $C_{5-10}$ azacycloalkyl or $C_{6-10}$ diazacycloalkyl, wherein the azacycloalkyl and the diazacycloalkyl are optionally substituted with up to two substituents independently selected from halo, hydroxy, amino, $C_{1-4}$ alkyl, $C_{2-6}$ alkanoyl, halo $C_{1-4}$ alkyl, $C_{1-4}$ alkylamino-$C_{1-4}$ alkyl and phenyl-$C_{1-4}$ alkyl wherein the phenyl moiety is optionally substituted with up to two substituents independently selected from halo, hydroxy and $C_{1-4}$ alkyl; and (f) $C_{7-14}$ mono- or di-azabicycloalkyl optionally substituted with up to two substituents independently selected from halo, hydroxy, amino, oxo, $C_{1-4}$ alkyl, halo $C_{1-4}$ alkyl, $C_{2-6}$ alkanoyl, phenyl-$C_{1-4}$ alkyl wherein the phenyl moiety is optionally substituted with up to two substituents independently selected from halo, hydroxy and $C_{1-4}$ alkyl, and phenylcarbonyl wherein the phenyl moiety is optionally substituted with up to two substituents independently selected from halo, hydroxy and $C_{1-4}$ alkyl.

2. A compound according to claim 1, wherein
$A^1$ and $A^2$ are each chloro or bromo;
$R^1$ and $R^2$ are independently $C_{1-3}$ alkyl;
$R^3$ is phenyl optionally substituted with up to three substituents independently selected from halo, hydroxy, $C_{1-4}$ alkyl, halo $C_{1-4}$ alkyl and $C_{1-4}$ alkoxy;
Y is heterocyclic group selected from piperazinyl, piperidinyl, pyrrolidinyl, 2,3,4,5,6,7-hexahydro-1H-1,4-diazepinyl, azabicyclo[3.3.0]octyl, quinuclidinyl, azabicyclo[3.2.1]octyl and azabicyclo[3.3.1]nonyl, the heterocyclic group being optionally substituted with, on the carbon atom, up to two substituents independently selected from $C_{1-4}$ alkyl, halo $C_{1-4}$ alkyl and $C_{1-4}$ alkoxy; and
$R^4$ is selected from the following:
(a) $C_{1-8}$ alkyl optionally substituted with up to three substituents independently selected from halo, hydroxy, amino, mono- or di-$C_{1-3}$ alkylamino, carbamoyl, carboxy, oxo, $C_{1-3}$ alkyl, $C_{1-3}$ alkoxy, $C_{2-4}$ alkanoylamino, $C_{1-3}$ alkoxycarbonyl, $C_{5-7}$ cycloalkyl, $C_{5-10}$ azacycloalkyl, $C_{7-10}$ azabicycloalkyl and $C_{6-10}$ diazacycloalkyl, wherein the azacycloalkyl, azabicycloalkyl and diazacycloalkyl are optionally substituted with up to two substituents independently selected from halo, hydroxy, $C_{1-4}$ alkyl, amino, oxo and $C_{2-6}$ alkanoyl;
(b) amino optionally substituted with up to two substituents independently selected from $C_{1-3}$ alkyl, halo-$C_{1-3}$ alkyl, amino-$C_{2-4}$ alkanoyl optionally substituted with $C_{1-3}$ alkyl $C_{5-7}$ cycloalkyl-$C_{1-3}$ alkyl and $C_{5-10}$ azabicycloalkyl optionally substituted with $C_{1-3}$ alkyl
(c) $C_{2-4}$ alkanoyl obtionally substituted with up to two substituents independently selected from halo, hydroxy, amino, $C_{1-3}$ alkyl, halo-$C_{1-3}$ alkyl, acetylamino, carbamoylamino, $C_{1-3}$ alkoxy, $C_{5-7}$ azacycloalkyl, $C_{1-3}$ alkoxycarbonyl-$C_{1-4}$ alkyl and $C_{5-7}$ cycloalkyl;
(d) $C_{5-7}$ cycloalkyl optionally substituted with up to two substituents selected from halo, hydroxy, amino, $C_{1-3}$ alkyl and halo-$C_{1-3}$ alkyl;
(e) $C_{5-7}$ azacycloalkyl optionally substituted with up to two substituents independently selected from halo, hydroxy, amino, $C_{1-3}$ alkyl, halo-$C_{1-3}$ alkyl, $C_{1-3}$ alkylamino-$C_{1-3}$ alkyl or benzyl; and
(f) $C_{7-14}$ azabicycloalkyl optionally substituted with up to two substituents independently selected from halo, hydroxy, amino, oxo, $C_{1-3}$ alkyl, halo-$C_{1-3}$ alkyl, $C_{2-4}$ alkanoyl, benzyl and benzoyl.

3. A compound according to claim 2, wherein
$A^1$ and $A^2$ are each chloro;
$R^1$ and $R^2$ are independently methyl or ethyl;
$R^3$ is phenyl optionally substituted with up to two substituents independently selected from halo, hydroxy, $C_{1-3}$ alkyl, $C_{1-4}$ alkoxy and halo $C_{1-3}$ alkyl;
Y is heterocyclic group selected from piperazinyl, piperidinyl, pyrrolidinyl, 2,3,4,5,6,7-hexahydro-1H-1, 4-diazepinyl and azabicyclo[3.3.0]octyl, the heterocyclic group being optionally substituted with, on the carbon atom, up to two substituents independently selected from $C_{1-3}$ alkyl, halo $C_{1-3}$ alkyl and $C_{1-3}$ alkoxy; and $R^4$ is selected from the following:

(a) $C_{1-6}$ alkyl optionally substituted with up to two substituents independently selected from hydroxy, amino, carbamoyl, carboxy, oxo, $C_{1-3}$ alkyl, $C_{2-4}$ alkanoylamino, $C_{1-3}$ alkoxycarbonyl, $C_{5-7}$ cycloalkyl, $C_{5-10}$ azacycloalkyl and $C_{6-10}$ diazacycloalkyl, wherein the azacycloalkyl and diazacycloalkyl are optionally substituted with up to two substituents independently selected from $C_{1-3}$ alkyl, amino, oxo and $C_{2-6}$ alkanoyl;

(b) amino optionally substituted with up to two substituents independently selected from $C_{1-3}$ alkyl, amino-$C_{2-4}$ alkanoyl optionally substituted with $C_{1-3}$ alkyl, $C_{5-7}$ cycloalkyl-$C_{1-3}$ alkyl and $C_{5-7}$ azabicycloalkyl optionally substituted with $C_{1-3}$ alkyl;

(c) $C_{2-4}$ alkanoyl optionally substituted with up to two substituents selected from $C_{1-3}$ alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-7}$ cycloalkyl optionally substituted with up to two substituents selected from halo, hydroxy and amino;

(e) $C_{5-7}$ azacycloalkyl optionally substituted with $C_{1-3}$ alkylamino-$C_{1-3}$ alkyl or benzyl; and (f) $C_{7-14}$ azabicycloalkyl optionally substituted with oxo, $C_{1-3}$ alkyl, $C_{2-4}$ alkanoyl, benzyl or benzoyl.

4. A compound according to claim 3, wherein $R^1$ and $R^2$ are independently methyl;

$R^3$ is phenyl optionally substituted with halo, hydroxy, methyl, methoxy or trifluoromethyl;

Y is piperazinyl, piperidinyl, pyrrolidinyl, 2,3,4,5,6,7-hexahydro-1H-1,4-diazepinyl or azabicyclo[3.3.0]octyl;

$R^4$ is selected from the following:

(a) $C_{1-5}$ alkyl optionally substituted with up to two substituents independently selected from hydroxy, amino, carbamoyl, carboxy, oxo, $C_{1-3}$ alkyl, $C_{2-4}$ alkanoylamino, $C_{1-3}$ alkoxycarbonyl, $C_{5-7}$ cycloalkyl, $C_{5-10}$ azacycloalkyl and $C_{6-10}$ diazacycloalkyl, wherein the azacycloalkyl and diazacycloalkyl are optionally substituted with methyl, amino, oxo or acetyl;

(b) amino optionally substituted with up to two substituents independently selected from $C_{1-3}$ alkyl, amino-$C_{2-4}$ alkanoyl substituted with methyl, $C_{5-7}$ cycloalkyl-$C_{1-3}$ alkyl and $C_{5-7}$ azabicycloalkyl optionally substituted with methyl;

(c) $C_{2-4}$ alkanoyl optionally substituted with up to two substituents selected from $C_{1-3}$ alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-7}$ cycloalkyl optionally substituted with up to two substituents selected from halo, hydroxy and amino;

(e) $C_{5-7}$ azacycloalkyl optionally substituted with $C_{1-3}$ alkylamino-$C_{1-3}$ alkyl or benzyl; and (f) $C_{7-10}$ azabicycloalkyl optionally substituted with oxo, $C_{1-3}$ alkyl, $C_{2-4}$ alkanoyl, benzyl or benzoyl.

5. A compound according to claim 4, wherein $R^3$ is phenyl optionally substituted with halo, hydroxy, methyl, methoxy or trifluoromethyl;

Y is piperazinyl, piperidinyl, pyrrolidinyl, 2,3,4,5,6,7-hexahydro-1H-1,4-diazepinyl or azabicyclo[3.3.0]octyl;

$R^4$ is selected from the following:

(a) $C_{1-3}$ alkyl optionally substituted with up to two substituents independently selected from hydroxy, amino, carbamoyl, carboxy, oxo, methyl, ethyl, acetylamino, methoxycarbonyl, $C_{5-6}$ cycloalkyl, $C_{5-10}$ azacycloalkyl and $C_{6-10}$ diazacycloalkyl, wherein the azacycloalkyl and diazacycloalkyl are optionally substituted with methyl, amino, oxo or acetyl;

(b) amino optionally substituted with up to two substituents independently selected from methyl, ethyl, 2-amino-2-methylpropionyl, $C_{5-6}$ cycloalkylmethyl and $C_{5-7}$ azabicycloalkyl optionally substituted with methyl;

(c) $C_{2-3}$ alkanoyl optionally substituted with up to two substituents selected from C1–3alkyl, amino, acetylamino, carbamoylamino, hydroxy, $C_{1-3}$ alkoxy, $C_{5-7}$ azacycloalkyl, $C_{1-3}$ alkoxycarbonylmethyl and $C_{5-7}$ cycloalkyl;

(d) $C_{5-6}$ cycloalkyl optionally substituted with up to two substituents selected from halo, hydroxy and amino;

(e) $C_{5-6}$ azacycloalkyl optionally substituted with $C_{1-3}$ alkylamino-$C_{1-3}$ alkyl or benzyl; and (f) $C_{7-10}$ azabicycloalkyl optionally substituted with oxo, $C_{1-3}$ alkyl, $C_{2-4}$ alkanoyl, benzyl or benzoyl.

6. A compound according to claim 5, wherein $R^3$ is phenyl; and $R^4$ is selected from the following:

(a) methyl, carbamoylmethyl, carboxymethyl, ethoxycarbonylmethyl, 2-(methoxycarbonyl)-2-methylpropyl, cyclohexylmethyl, 1-pyrrolidinoethyl, pyrrolidinopropyl, [(2R,S)-1-methyl-2-pyrrolidinyl]methyl, [(2S)-1-methyl-2-pyrrolidinyl]methyl, [(2R)-1-methyl-2-pyrrolidinyl]methyl, [(2R,S)-1-methyl-2-piperidinyl]methyl, 3-(4-acetylpiperazinyl)-1-propyl, 3-(2-oxopyrrolidino)-1-propyl, 3-(4-methylpiperazinyl)propyl, (2-amino-2-methyl)propyl, (2-acetylamino-2-methyl)propyl, (2,2-dimethyl-3-hydroxy)propyl, (3-hydroxy-3-methyl)butyl, (3-(4-methylpiperazinyl)-3-oxopropyl, 3-(4-methylpiperazinyl)-1-oxopropyl, 3-(4-acetylpiperazinyl)-1,3-dioxopropyl and 3-pyrrolidino-3-oxo-1-propyl;

(b) dimethylamino, 2-amino-2-methylpropionylamino, cyclohexylmethylamino and 8-methyl-8-azabicyclo[3.2.1]oct-7-ylamino;

(c) (2-amino-2-methyl)propinoyl, (2-acetylamino-2-methyl)propionyl, (2,2-dimethyl-3-hydroxy)propionyl, [2-(N-carbamoyl)amino-2-methyl]propionyl, (2,2-dimethyl)propionyl, 3-(ethoxycarbonyl)propionyl, 2-(1-pyrrolidino)acetyl and 1-(methoxycarbonylmethyl)cyclopent-1-yl-acetyl (d) cyclopentyl and 4-aminocyclohexyl;

(e) piperidino, (R,S)-2-(dimethylamino)methylpyrrolidino and 4-benzylpiperazinyl; and (f) 8-methyl-8-azabicyclo[3.2.1]oct-3-yl, 8-acetyl-8-azabicyclo[3.2.1]oct-3-yl, 8-ethyl-8-azabicyclo[3.2.1]oct-3-yl, 8-isopropyl-8-azabicyclo[3.2.1]oct-3-yl, 8-benzyl-8-azabicyclo[3.2.1]oct-3-yl, 3-acetyl-3-azabicyclo[3.3.0]oct-7-yl, 4-(3-benzoyl3-azabicyclo[3.3.0]oct-7-yl and 3-oxo-bicyclo[3.3.0]oct-7-yl.

7. A compound according to claim 1, being one of the following:

(−)-(4S)-dimethyl 4-(2,6-dichlorophenyl)-2-[4-(8-methyl-8-azabicyclo[3.2.1]oct-3-yl)-1-piperazinyl]carbonylmethyl-6-(S)-phenylsulfinylmethyl-1,4-dihydropyridine-3,5-dicarboxylate dicitrate;

(−)-(4S)-dimethyl 4-(2,6-dichlorophenyl)-2-[4-(8-acetyl-8-azabicyclo[3.2.1]oct-3-yl)-1-piperazinylcarbonylmethyl]-6-(S)-phenylsulfinylmethyl-1,4-dihydropyridine-3,5-dicarboxylate monohydrochloride;

(−)-(4S)-dimethyl 4-(2,6-dichlorophenyl)-2-[4-(8-ethyl-8-azabicyclo[3.2.1]oct-3-yl)-1-piperazinylcarbonylmethyl]-6-(S)-phenylsulfinylmethyl-1,4-dihydropyridine-3,5-dicarboxylate dihydrochloride;

(−)-(4S)-dimethyl 4-(2,6-dichlorophenyl)-2-[(3S)-3-(N-methyl-8-azabicyclo[3,2,1]oct-7-yl)amino-1-pyrrolidino]carbonylmethyl-6-[(S)-phenylsulfinylmethyl]-1,4-dihydropyridine-3,5-dicarboxylate, dihydrochloride;

(−)-(4S)-dimethyl 4-(2,6-dichlorophenyl)-2-[4-(3-oxo-bicyclo[3,3,0]oct-7-yl)-1-piperazinyl]carbonylmethyl-6-[(S)-phenylsulfinylmethyl-1,4-dihydropyridine-3,5-dicarboxylate, monocitrate;

(−)-(4S)-dimethyl 4-(2,6-dichlorophenyl)-2-{4-(3-pyrrolidino-3-oxo-1-propyl)-1-piperazinyl]carbonylmethyl-6-(S)-phenylsulfinylmethyl-1,4-dihydropyridine-3,5-dicarboxylate monohydrochloride;

(−)-(4S)-dimethyl 4-(2,6-dichlorophenyl)-2-[4-[3-(2-oxopyrrolidino)prop-1-yl]piperazinyl]carbonylmethyl-6-(S)-phenylsulfinylmethyl-1,4-dihydropyridine-3,5-dicarboxylate monohydrochloride; and (−)-(4S)-dimethyl 4-(2,6-dichlorophenyl)-2-[4-(3-acetyl-3-azabicyclo[3.3.0]oct-7-yl)piperazinylcarbonylmethyl]-6-(S)-phenylsulfinylmethyl-1,4-dihydropyridine-3,5-dicarboxylate monohydrochloride.

8. A pharmaceutical composition for the treatment of inflammation, cardiovascular disease, pain, common cold, allergies, asthma, pancreatitis, burns, virus infection, head injury, multiple trauma, which comprises a therapeutically effective amount of a compound of claim 1 or its pharmaceutically acceptable carrier.

\* \* \* \* \*